United States Patent [19]

Blankley et al.

[11] Patent Number: 5,952,342

[45] Date of Patent: Sep. 14, 1999

[54] 6-ARYL NAPHTHYRIDINES FOR INHIBITING PROTEIN TYROSINE KINASE MEDIATED CELLULAR PROLIFERATION

[75] Inventors: Clifton John Blankley; Annette Marian Doherty; James Marino Hamby, all of Ann Arbor; Robert Lee Panek, Canton; Mel Conrad Schroeder, Dexter; Howard Daniel Hollis Showalter, Ann Arbor; Cleo Connolly, Livonia, all of Mich.

[73] Assignee: Warner-Lambert Company, Morris Plains, N.J.

[21] Appl. No.: 09/040,792

[22] Filed: Mar. 18, 1998

Related U.S. Application Data

[60] Division of application No. 08/539,410, Nov. 6, 1995, Pat. No. 5,733,913, which is a continuation-in-part of application No. 08/339,051, Nov. 14, 1994, abandoned.

[51] Int. Cl.⁶ .......................... C07D 471/04; A61K 31/44

[52] U.S. Cl. .......................... 514/300; 544/279; 544/300; 544/333; 544/405; 546/122; 514/254; 514/256; 514/258

[58] Field of Search .................. 546/122; 514/300, 514/254, 256; 544/333, 405

[56] References Cited

U.S. PATENT DOCUMENTS 4,271,164    6/1981   Blankley et al. ....................... 424/251

*Primary Examiner*—Mukund J. Shah
*Assistant Examiner*—Ann M. Kessinger
*Attorney, Agent, or Firm*—Charles W. Ashbrook

[57] ABSTRACT

6-Aryl naphthyridines are inhibitors of protein tyrosine kinase, and are thus useful in treating cellular proliferation mediated thereby. The compounds are especially useful in treating atherosclerosis, restenosis, psoriasis, as well as bacterial infections.

16 Claims, No Drawings

6-ARYL NAPHTHYRIDINES FOR INHIBITING PROTEIN TYROSINE KINASE MEDIATED CELLULAR PROLIFERATION

This application is a divisional of application Ser. No.08/539,410 filed Nov. 6, 1995, now U.S. Pat. No. 5,733,913, which is a Continuation in Part of U.S. Ser. No. 08/339,051 filed Nov. 14, 1995, now abandoned.

FIELD OF THE INVENTION

This invention relates to inhibition of protein tyrosine kinase (PTK) mediated cellular proliferation. More specifically, this invention relates to the use of pyrido[2,3-d]pyrimidines and naphthyridine compounds in inhibiting cellular proliferation and protein tyrosine kinase enzymatic activity.

BACKGROUND OF THE INVENTION

Many disease states are characterized by the uncontrolled proliferation and differentiation of cells. These disease states encompass a variety of cell types and maladies such as, cancer, atherosclerosis, and restenosis. Growth factor stimulation, autophosphorylation, and the phosphorylation of intracellular protein substrates are important biological events in the pathomechanisms of proliferative diseases.

In normal cells, the phosphorylation of tyrosine residues on protein substrates serves a critical function in intracellular growth signaling pathways initiated by stimulated extracellular growth factor receptors. For example, the association of growth factors such as Platelet Derived Growth Factor (PDGF), Fibroblast Growth Factor (FGF), and Epidermal Growth Factor (EGF) with their respective extracellular receptors activates intracellular tyrosine kinase enzyme domains of these receptors, thereby catalyzing the phosphorylation of either intracellular substrates or the receptors themselves. The phosphorylation of growth factor receptors in response to ligand binding is known as autophosphorylation.

For example, the EGF receptor has as its two most important ligands EGF and Transforming Growth Factor α, (TGFα). The receptors appear to have only minor functions in normal adult humans, but are implicated in the disease processes of a large portion of all cancers, especially colon and breast cancer. The closely related Erb-B2 and Erb-B3 receptors have a family of Heregulins as their major ligands, and receptor overexpression and mutation have been unequivocally demonstrated as the major risk factor in poor prognosis breast cancer.

The proliferation and directed migration of vascular smooth muscle cells (VSMC) are important components in such processes as vascular remodeling, restenosis and atherosclerosis. Platelet-derived growth factor has been identified as one of the most potent endogenous VSMC mitogens and chemoattractants. Elevated vascular mRNA expression of PDGF-A and -B chains and PDGF receptors has been observed in balloon-injured rat carotid arteries (*J. Cell. Biol.,* 111:2149–2158 (1990)). In this injury model, infusion of PDGF also greatly increases intimal thickening and migration of VSMC (*J. Clin. Invest.,* 89:507–511 (1992)). Furthermore, PDGF-neutralizing antibodies significantly reduce intimal thickening following balloon injury (*Science,* 253:1129–1132 (1991)).

Both acidic fibroblast growth factor (aFGF) and basic fibroblast growth factor (bFGF) have many biological activities, including the ability to promote cellular proliferation and differentiation. Tyrphostin receptor tyrosine kinase inhibitors which block the PDGF signal transduction pathway have been shown to inhibit PDGF stimulated receptor tyrosine kinase phosphorylation in vivo in the rat model of balloon angioplasty (*Drug Develop. Res.,* 29:158–166 (1993)). Direct evidence in support of FGF involvement in VSMC has been reported by Lindner and Reidy (*Proc. Natl. Acad. Sci. USA,* 88:3739–3743 (1991)), who demonstrated that the systemic injection of a neutralizing antibody against bFGF prior to balloon angioplasty of rat carotid arteries inhibited injury-induced medial SMC proliferation by greater than 80% when measured 2 days after injury. It is likely that bFGF released from damaged cells is acting in a paracrine manner to induce VSMC growth. Recently, Lindner and Reidy (*Cir. Res.,* 73:589–595 (1993)) demonstrated an increased expression of both mRNA for bFGF and FGFR-1 in replicating VSMCs and endothelium in en face preparations of balloon-injured rat carotid arteries. The data provides evidence that in injured arteries the ligand/receptor system of bFGF and FGFR-1 may be involved in the continued proliferative response of VSMCs leading to neointima formation.

Thus, EGF, PDGF, FGF, and other growth factors play pivotal roles in the pathomechanisms of cellular proliferative diseases such as cancer, atherosclerosis, and restenosis. Upon association with their respective receptors, these growth factors stimulate tyrosine kinase activity as one of the initial biochemical events leading to DNA synthesis and cell division. It thereby follows that compounds which inhibit protein tyrosine kinases associated with intracellular growth factor signal transduction pathways are useful agents for the treatment of cellular proliferative diseases. We have now discovered that certain pyrido[2,3-d]-pyrimidines and naphthyridines inhibit protein tyrosine kinases, and are useful in treating and preventing atherosclerosis, restenosis, and cancer.

Several pyrido[2,3-d]pyrimidines and naphthyridines are known. For example, U.S. Pat. No. 3,534,039 discloses a series of 2,7-diamino-6-arylpyrido[2,3-d]pyrimidine compounds as diuretic agents; U.S. Pat. No. 3,639,401 discloses a series of 6-aryl-2,7-bis[(trialkylsilyl)amino]pyrido[2,3-d]-pyrimidine compounds as diuretic agents; U.S. Pat. No. 4,271,164 discloses a series of 6-substituted-arylpyrido[2,3-d]pyrimidin-7-amines and derivatives as antihypertensive agents; European Published Application Number 0 537 463 A2 discloses a series of substituted-pyrido[2,3-d] pyrimidines useful as herbicides; U.S. Pat. No. 4,771,054 discloses certain naphthyridines as antibiotics. None of the foregoing references teach the compounds of this invention or suggest such compounds are useful for treating atherosclerosis, restenosis, and cancer.

SUMMARY OF THE INVENTION

This invention provides new compounds characterized as pyrido[2,3-d]pyrimidines and 1,6-naphthyridines which are useful in inhibiting protein tyrosine kinase, and thus are effective in treating cellular proliferative diseases of atherosclerosis, restenosis, and cancer. The invention is more particularly directed to compounds defined by the Formula I

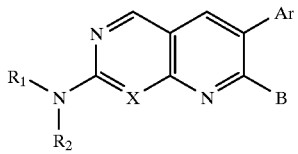

I wherein

X is CH or N;

B is halo, hydroxy, or $NR_3R_4$;

$R_1$, $R_2$, $R_3$, and $R_4$ independently are hydrogen, $C_1$–$C_8$ alkyl, $C_2$–$C_8$ alkenyl, $C_2$–$C_8$ alkynyl, Ar', amino, $C_1$–$C_8$ alkylamino or di-$C_1$–$C_8$ alkylamino; and wherein the alkyl, alkenyl, and alkynyl groups may be substituted by $NR_5R_6$, where $R_5$ and $R_6$ are independently hydrogen, $C_1$–$C_8$ alkyl, $C_2$–$C_8$ alkenyl, $C_2$–$C_8$ alkynyl, $C_3$–$C_{10}$ cycloalkyl or

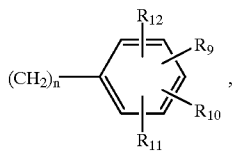

and wherein any of the foregoing alkyl, alkenyl, and alkynyl groups may be substituted with hydroxy or a 5- or 6-membered carbocyclic or heterocyclic ring containing 1 or 2 heteroatoms selected from nitrogen, oxygen, and sulfur, and $R_9$, $R_{10}$, $R_{11}$, and $R_{12}$ independently are hydrogen, nitro, trifluoromethyl, phenyl, substituted phenyl, —C≡N, —$COOR_8$, —$COR_8$,

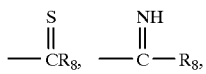

$SO_2R_8$, halo, $C_1$–$C_8$ alkyl, $C_1$–$C_8$ alkoxy, thio, —S—$C_1$–$C_8$ alkyl, hydroxy, $C_1$–$C_8$ alkanoyl, $C_1$–$C_8$ alkanoyloxy, or —$NR_5R_6$, or $R_9$ and $R_{10}$ taken together when adjacent can be methylenedioxy; n is 0, 1, 2, or 3; and wherein $R_5$ and $R_6$ together with the nitrogen to which they are attached can complete a ring having 3 to 6 carbon atoms and optionally containing a heteroatom selected from nitrogen, oxygen, and sulfur;

$R_1$ and $R_2$ together with the nitrogen to which they are attached, and $R_3$ and $R_4$ together with the nitrogen to which they are attached, can also be

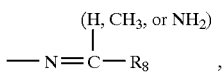

or can complete a ring having 3 to 6 carbon atoms and optionally containing 1 or 2 heteroatoms selected from nitrogen, oxygen, and sulfur, and $R_1$ and $R_3$ additionally can be an acyl analog selected from

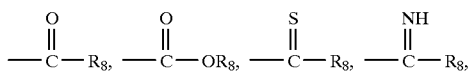

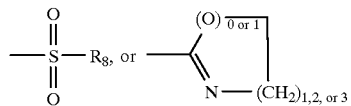

in which $R_8$ is hydrogen, $C_1$–$C_8$ alkyl, $C_2$–$C_8$ alkenyl, $C_2$–$C_8$ alkynyl, $C_3$–$C_{10}$ cycloalkyl, optionally containing an oxygen, nitrogen, or sulfur atom,

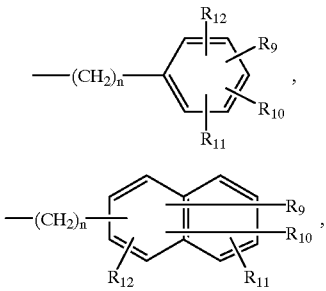

and —$NR_5R_6$, and wherein the $R_8$ alkyl, akenyl, and alkynyl groups can be substituted by $NR_5R_6$;

Ar and AR' are unsubstituted or substituted aromatic or heteroaromatic groups selected from phenyl, imidazolyl, pyrrolyl, pyridyl, pyrimidyl, benzimidazolyl, benzothienyl, benzofuranyl, indolyl, pyrazinyl, thiazolyl, oxazolyl, isoxazolyl, furanyl, thienyl, naphthyl, wherein the substituents are $R_9$, $R_{10}$, $R_{11}$, and $R_{12}$ as defined above;

and the pharmaceutically acceptable acid and base addition salts thereof; provided that when X is N and B is $NR_3R_4$, one of $R_3$ and $R_4$ is other than hydrogen.

Preferred compounds have Formula I wherein Ar is phenyl or substituted phenyl of the formula

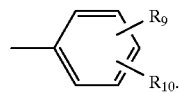

Additionally preferred are compounds wherein B is —$NR_3R_4$.

Further preferred compounds are those wherein one or both of $R_1$ and $R_3$ are

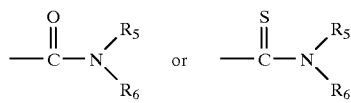

and $R_2$ and $R_4$ are hydrogen.

Still further preferred compounds have Formula I wherein B is $NR_3R_4$, $R_1$ and $R_3$ independently are hydrogen,

where $R_8$ is $C_1$–$C_8$ alkyl or $NR_5R_6$.

A particularly preferred group of compounds have the formula

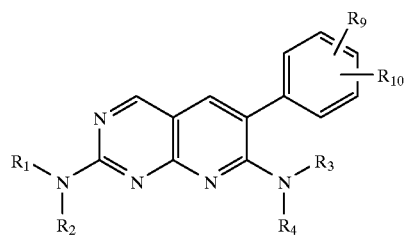

wherein $R_2$ and $R_4$ are hydrogen, $R_1$ and $R_3$ independently are hydrogen, $C_1-C_8$ alkyl,

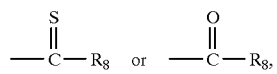

where $R_8$ is $C_1-C_8$ alkyl or $-NR_5R_6$, $R_5$ is hydrogen and $R_6$ is $C_1-C_8$ alkyl, and $R_9$ and $R_{10}$ independently are hydrogen, halo, $C_1-C_8$ alkyl, or $C_1-C_8$ alkoxy.

Another preferred group of compounds have the formulas

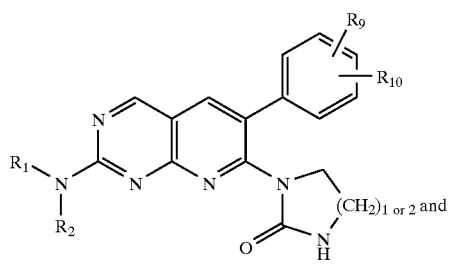

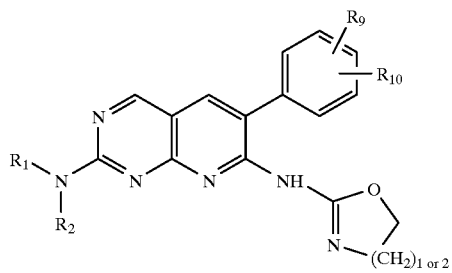

wherein $R_1$, $R_2$, $R_9$, and $R_{10}$ are as defined above.

Also preferred are compounds of the formula

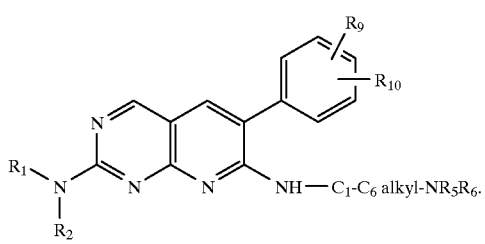

Also preferred are compounds of the formula

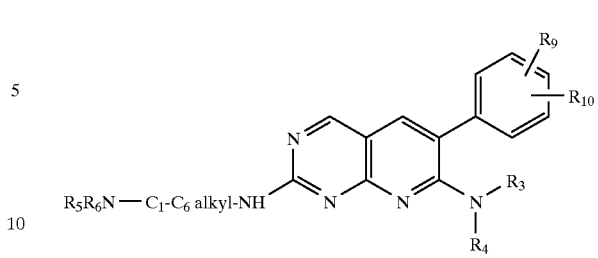

especially where $R_5$ and $R_6$ together with the nitrogen to which they are attached from a cyclic ring such as morpholino, piperazino, 4-alkylpiperazino, and the like.

Additionally preferred are compounds of the formula

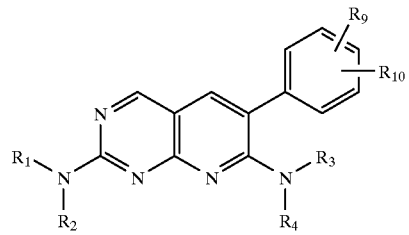

wherein $R_2$ and $R_4$ are hydrogen, $R_1$ and $R_3$ independently are hydrogen, $C_1-C6$ alkyl,

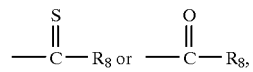

where $R_8$, $R_9$, and $R_{10}$ are as defined above.

Also preferred are compounds of the formula

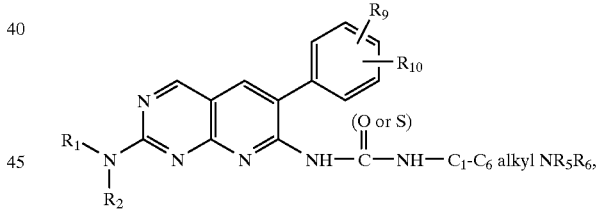

especially where $R_5$ and $R_6$ together with the nitrogen to which they are attached form a cyclic ring such as morpholino, piperazino, 4-alkylpiperazino, and the like.

The most preferred compounds of the invention include the following:

1-tert-butyl-3-[7-(3-tert-butylureido)-6-(2,6-dichlorophenyl)-pyrido[2,3-d]pyrimidin-2-yl]urea;

1-[2-amino-6-(2,6-dichlorophenyl)-pyrido[2,3-d]-pyrimidin-7-yl]-3-tert-butylurea;

1-tert-butyl-3-[7-(3-tert-butylureido)-6-o-tolyl-pyrido[2,3-d]pyrimidin-2-yl]urea;

1-[2-amino-6-o-tolyl-pyrido[2,3-d]pyrimidin-7-yl]-3-tert-butylurea;

1-[2-amino-6-(2,6-dimethylphenyl)-pyrido[2,3-d]-pyrimidin-7-yl]-3-tert-butylurea;

N-[2-acetylamino-6-(2,6-dichlorophenyl)-pyrido[2,3-d] pyrimidin-7-yl]-acetamide;

$N^7$-butyl-6-phenyl-pyrido[2,3-d]pyrimidine-2,7-diamine;

3-o-tolyl-[1,6]naphthyridine-2,7-diamine;
3-(2-chlorophenyl)-[1,6]naphthyridine-2,7-diamine;
$N^2,N^7$-dimethyl-6-phenyl-pyrido[2,3-d]pyrimidine-2,7-diamine;
7-amino-6-(2,6-dichlorophenyl)-2-(3-diethylaminopropylamino)-pyrido[2,3-d]pyrimidine;
1-tert-butyl-3-[6-(2,6-dichlorophenyl)-2-(3-diethylamino-propylamino)-pyrido[2,3-d]pyrimidin-7-yl]urea;
1-[2-amino-6-(2,6-dichlorophenyl)-pyrido[2,3-d]pyrimidin-7-yl]-3-ethylurea;
1-[2-amino-6-(2,6-dichlorophenyl)-pyrido[2,3-d]pyrimidin-7-yl]-3-(3-morpholino-4-yl-propyl)-thiourea;
1-(2-amino-6-(2,6-dichlorophenyl)-pyrido[2,3-d]pyrimidin-7-yl]-imidazolidin-2-one;
N'-[7-(3-tert-Butyl-ureido)-6-(2,6-dichlorophenyl)-pyrido[2,3-d]pyrimidin-2-yl]-N,N-dimethylformamidine;
N'-[6-(2,6-Dichloro-phenyl)-7-(dimethylamino-methyleneamino)-pyrido[2,3-d]pyrimidin-2-yl]-N,N-dimethyl-formamidine;
1-tert-Butyl-3-[2-(3-diethylamino-propylamino)-6-(2,6-dimethyl-phenyl)-pyrido[2,3-d]pyrimidin-7-yl]-urea;
1-tert-Butyl-3-[6-(2,6-dichloro-phenyl)-2-(4-diethylamino-butylamino)-pyrido[2,3-d]pyrimidin-7-yl]-urea;
1-[2-Amino-6-(2,3-dichloro-phenyl)-pyrido[2,3-d]pyrimidin-7-yl]-3-tert-butyl-urea;
1-[2-Amino-6-(3-methoxy-phenyl)-pyrido[2,3-d]pyrimidin-7-yl]-3-tert-butyl-urea;
1-[2-Amino-6-(2,3-dimethyl-phenyl)-pyrido[2,3-d]pyrimidin-7-yl]-3-tert-butyl-urea;
1-tert-Butyl-3-{6-(2,6-dichloro-phenyl)-2-[3-(4-methyl-piperazin-1-yl)-propylamino]-pyrido[2,3-d]pyrimidin-7-yl}-urea;
N'-[6-(2,6-Dichloro-phenyl)-2-(3-diethylamino-propylamino)-pyrido[2,3-d]pyrimidin-7-yl]-N,N-dimethyl-formamidine;
1-[2-Amino-6-(2,3,6-trichloro-phenyl)-pyrido[2,3-d]pyrimidin-7-yl]-3-tert-butyl-urea;
1-[2-Amino-6-(2-methoxy-phenyl)-pyrido[2,3-d]pyrimidin-7-yl]-3-tert-butyl-urea;
1-tert-Butyl-3-{6-(2,6-dichloro-phenyl)-2-[(3-dimethylamino-propyl)-methyl-amino]-pyrido[2,3-d]pyrimidin-7-yl}-urea;
1-(2-Amino-6-pyridin-3-yl-pyrido[2,3-d]pyrimidin-7-yl)-3-tert-butyl-urea;
1-{6-(2,6-Dichloro-phenyl)-2-[3-(4-methyl-piperazin-1-yl)-propylamino]-pyrido[2,3-d]pyrimidin-7-yl}-3-phenyl-urea;
1-[2-Amino-6-(2,3,5,6-tetramethyl-phenyl)-pyrido[2,3-d]pyrimidin-7-yl]-3-tert-butyl-urea;
1-[2-Amino-6-(2-bromo-6-chloro-phenyl)-pyrido[2,3-d]pyrimidin-7-yl]-3-tert-butyl-urea;
1-(2-Amino-6-pyridin-4-yl-pyrido[2,3-d]pyrimidin-7-yl)-3-tert-butyl-urea;
1-[2-Amino-6-(3,5-dimethyl-phenyl)-pyrido[2,3-d]pyrimidin-7-yl]-3-tert-butyl-urea;
1-[2-Amino-6-(2-bromo-6-chloro-phenyl)-pyrido[2,3-d]pyrimidin-7-yl]-3-tert-butyl-urea;
1-[6-(2,6-Dichloro-phenyl)-2-(4-diethylamino-butylamino)-pyrido[2,3-d]pyrimidin-7-yl]-3-ethyl-urea;
Propane-1-sulfonic acid [2-amino-6-(2,6-dichloro-phenyl)-pyrido[2,3-d]pyrimidin-7-yl]-amide;
1-[2-Amino-6-(2,6-difluoro-phenyl)-pyrido[2,3-d]pyrimidin-7-yl]-3-tert-butyl-urea;
1-tert-Butyl-3-[6-(2,6-dibromo-phenyl)-2-(3-diethylamino-propylamino)-pyrido[2,3-d]pyrimidin-7-yl]-urea;
1-tert-Butyl-3-[6-(2,6-dichloro-phenyl)-2-(3-dimethylamino-2,2-dimethyl-propylamino)-pyrido[2,3-d]pyrimidin-7-yl]-urea;
1-tert-Butyl-3-{6-(2,6-dichloro-phenyl)-2-[3-(2-methyl-piperidin-1-yl)-propylamino]-pyrido[2,3-d]pyrimidin-7-yl}-urea;
1-[2-Amino-6-(2,4,6-trimethyl-phenyl)-pyrido[2,3-d]pyrimidin-7-yl]-3-tert-butyl-urea;
1-Adamantan-1-yl-3-{6-(2,6-dichloro-phenyl)-2-[3-(4-methyl-piperazin-1-yl)-propylamino]-pyrido[2,3-d]pyrimidin-7-yl}-urea;
1-Cyclohexyl-3-{6-(2,6-dichloro-phenyl)-2-[3-(4-methyl-piperazin-1-yl)-propylamino]-pyrido[2,3-d]pyrimidin-7-yl}-urea;
1-{6-(2,6-Dichloro-phenyl)-2-[3-(4-methyl-piperazin-1-yl)-propylamino]-pyrido[2,3-d]pyrimidin-7-yl}-3-(3-methoxy-phenyl)-urea;
1-tert-Butyl-3-{6-(2,6-dichloro-phenyl)-2-[4-(4-methyl-piperazin-1-yl)-butylamino]-pyrido[2,3-d]pyrimidin-7-yl}-urea;
1-tert-Butyl-3-{6-(2,6-dichloro-phenyl)-2-[3-(4-methyl-piperazin-1-yl)-propylamino]-pyrido[2,3-d]pyrimidin-7-yl}-thiourea;
1-tert-Butyl-3-[2-[3-(4-methyl-piperazin-1-yl)-propylamino]-6-(2,3,5,6-tetramethyl-phenyl)-pyrido[2,3-d]pyrimidin-7-yl]-urea;
1-Allyl-3-{6-(2,6-dichloro-phenyl)-2-[3-(4-methyl-piperazin-1-yl)-propylamino]-pyrido[2,3-d]pyrimidin-7-yl}-urea;
6-(2, 6-Dichloro-phenyl)-$N^7$-(5, 6-dihydro-4H-[1,3] oxazin-2-yl)-$N^2$-[3-(4-methyl-piperazin-1-yl)-propyl]-pyrido[2,3-d]pyrimidine-2,7-diamine; and
3-{6-(2,6-Dichloro-phenyl)-2-[3-(4-methyl-piperazin-1-yl)-propylamino]-pyrido[2,3-d]pyrimidin-7-yl}-1,1-diethyl-urea.

Yet another preferred group of compounds are amidines of the formula

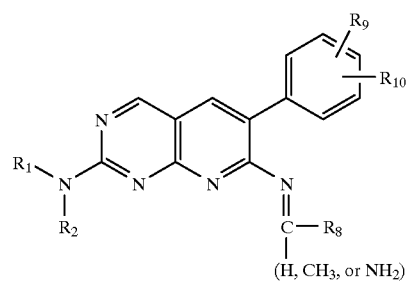

especially where $R_8$ is $-NR_5R_6$.

Another preferred group of compounds have Formula I wherein Ar is other than phenyl or substituted phenyl. Typical of such compounds are pyridines of the formula

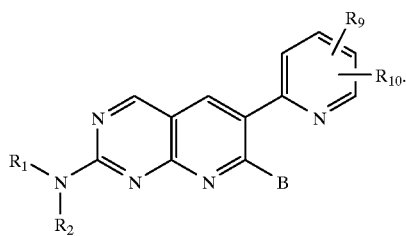

This invention also provides pharmaceutical formulations comprising a compound of Formula I together with a pharmaceutically acceptable carrier, diluent, or excipient therefor.

Compounds within the scope of the present invention have a specific affinity towards one or more of the substrate site of the tyrosine kinase domains of EGF, FGF, PDGF, V-src and C-src. Compounds within the scope of the present invention have effectively inhibited EGF and PDGF autophosphorylation of the receptor and inhibited vascular smooth muscle cell proliferation and migration.

As inhibitors of protein kinase, the compounds of the instant invention are useful in controlling proliferative disorders including leukemia, cancer, psoriasis, vascular smooth muscle proliferation associated with atherosclerosis, and postsurgical vascular stenosis and restenosis in mammals.

A further embodiment of this invention is a method of treating subjects suffering from diseases caused by vascular smooth muscle proliferation. The method entails inhibiting vascular smooth muscle proliferation and/or migration by administering an effective amount of a compound of Formula I to a subject in need of treatment.

Finally, the present invention is directed to methods for the preparation of a compound of Formula I and synthetic intermediates

DETAILED DESCRIPTION OF THE INVENTION

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

In the compounds of Formula I, the term "$C_1$–$C_8$ alkyl" means a straight or branched hydrocarbon radical having from 1 to 8 carbon atoms and includes, for example, methyl, ethyl, n-propyl, isopropyl, n-butyl, sec-butyl, isobutyl, tert-butyl, n-pentyl, 2,2-dimethylpropyl, n-hexyl, n-heptyl, n-octyl, and the like. Preferred are $C_1$–$C_6$ alkyl groups.

"Halo" includes fluoro, chloro, bromo, and iodo.

"$C_2$–$C_8$ Alkenyl" means straight and branched hydrocarbon radicals having from 2 to 8 carbon atoms and 1 double bond and includes ethenyl, 3-buten-1-yl, 2-ethenylbutyl, 3-octen-1-yl, and the like. Typical $C_2$–$C_8$ alkynyl groups include propynyl, 2-butyn-1-yl, 3-pentyn-1-yl, and the like. $C_2$–$C_6$ Alkenyl are preferred.

"$C_3$–$C_{10}$ Cycloalkyl" means a cyclic or bicyclic hydrocarbyl group such as cyclopropyl, cyclobutyl, cyclohexyl, cyclopentyl, adamantyl, bicyclo[3.2.1]octyl, bicyclo[2.2.1]heptyl, and the like, as well heterocyclics such as piperazinyl, tetrahydropyranyl, pyrrolidinyl, and the like.

"$C_1$–$C_8$ Alkoxy" refers to the alkyl groups mentioned above binding through oxygen, examples of which include methoxy, ethoxy, isopropoxy, tert-butoxy, n-octyloxy, and the like. $C_1$–$C_6$ Alkoxy groups are preferred.

Typical "$C_1$–$C_8$ alkanoyl" groups include formyl, acetyl, propionyl, butyryl, and isobutyryl. "$C_1$–$C_8$ alkanoyloxy" includes acetoxy, tert-butanoyloxy, pentanoyloxy, and the like.

The alkyl, alkenyl, and alkynyl groups may be substituted with $NR_5R_6$ and 5- or 6-membered carbocyclic and heterocyclic groups, containing 1 or 2 heteroatoms selected from nitrogen, oxygen, and sulfur. Such rings may be substituted, for example with one or two $C_1$–$C_6$ alkyl groups. Examples include dimethylaminomethyl, 4-diethylamino-3-buten-1-yl, 5-ethylmethylamino-3-pentyn-1-yl-4-morpholinobutyl, 4-(4-methylpiperazin-1-yl)butyl, 4-tetrahydropyridinylbutyl-, 2-methyltetrahydropyridinomethyl-, 3-imidazolidin-1-ylpropyl, 4-tetrahydrothiazol-3-yl-butyl, phenylmethyl, 3-chlorophenylmethyl, and the like.

The terms "Ar" and "Ar'" refer to unsubstituted and substituted aromatic and heteroaromatic groups such as phenyl, 3-chlorophenyl, 2,6-dibromophenyl, pyridyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, and the like.

Preferred Ar and Ar' groups are phenyl and phenyl substituted by 1, 2, or 3 groups independently selected from halo, alkyl, alkoxy, thio, thioalkyl, hydroxy, alkanoyl, —CN, —$NO_2$, —$COOR_8$, —$CF_3$ alkanoyloxy, or amino of the formula —$NR_5R_6$. Disubstituted phenyl is preferred, and 2,6-disubstituted phenyl is especially preferred. Other preferred Ar and Ar' groups include pyridyl, e.g., 2-pyridyl and 4-pyridyl.

Typical Ar and Ar' substituted phenyl groups thus include 2-aminophenyl, 3-chloro-4-methoxyphenyl, 2,6-diethylphenyl, 2-n-hexyl-3-fluorophenyl, 3-hydroxyphenyl, 3,4-dimethoxyphenyl, 2,6-dichlorophenyl, 2-chloro-6-methylphenyl, 2,4,6-trichlorophenyl, 2,6-dimethoxyphenyl, 2,6-dihydroxyphenyl, 2,6-dibromophenyl, 2,6-dinitrophenyl, 2,6-di-(trifluoromethyl)phenyl, 2,6-dimethylphenyl, 2,3,6-trimethylphenyl, 2,6-dibromo-4-methylphenyl, and the like.

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharmaceutical Science*, 66:1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge S. M., et al., "Pharmaceutical Salts," *J. of Pharmaceutical Science,* 66:1–19 (1977)).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

While the forms of the invention herein constitute presently preferred embodiments, many others are possible. It is not intended herein to mention all of the possible equivalent forms or ramifications of the invention. It is understood that the terms used herein are merely descriptive rather than limiting, and that various changes may be made without departing from the spirit or scope of the invention.

Compounds of Formula I may be prepared according to the syntheses outlined in Schemes I–VII. Although these schemes often indicate exact structures, the methods apply widely to analogous compounds of Formula I, given appropriate consideration to protection and deprotection of reactive functional groups by methods standard to the art of organic chemistry. For example, hydroxy groups, in order to prevent unwanted side reactions, generally need to be converted to ethers or esters during chemical reactions at other sites in the molecule. The hydroxy protecting group is readily removed to provide the free hydroxy group. Amino groups and carboxylic acid groups are similarly derivatized to protect them against unwanted side reactions. Typical protecting groups, and methods for attaching and cleaving them, are described fully by Greene and Wuts in *Protective Groups in Organic Synthesis,* John Wiley and Sons, New York, (2nd Ed, 1991), and McOmie, *Protective Groups in Organic Chemistry,* Plenum Press, New York, 1973.

Scheme I describes a typical method for the preparation of 1-tert-butyl-3-[7-(3-tert-butylureido)- 6-(aryl)-pyrido[2,3-d]pyrimidin-2-yl]ureas and 1-[2-Amino-6-(aryl)-pyrido[2,3-d]pyrimidin-7-yl]-3-tert-butylureas from the key intermediate 2,7-diamino-6-(aryl)-pyrido[2,3-d]pyrimidine, which can be prepared by the method of U.S. Pat. No. 3,534,039. Generally, the reaction can be accomplished by reacting 2,7-diamino-6-(aryl)-pyrido[2,3-d]pyrimidine compounds with one equivalent of an acylating agent, such as an alkyl isocyanate, isothiocyanate, carbamoyl chloride, carbamoyl bromide, sulfamoyl chloride, chloroformate, or other activated acid derivatives such as symmetrical anhydrides, mixed anhydride, and the like. The reaction is carried out in neat isocyanate, or in the presence of a base, preferably sodium hydride in a suitable unreactive solvent such as dimethylformamide, dioxane, or the like. The starting material, a 2,7-diamino-6-(aryl)-pyrido[2,3-d]pyrimidine, can be reacted in the same manner as described above using a two-fold excess or greater of acylating reagent to give primarily the diacylated compounds, for example a 1-tert-butyl-3-[7-(3-tert-butylureido)-6-(aryl)-pyrido-[2,3-d]pyrimidin-2-yl]urea.

The acylation generally is substantially complete when conducted for about 1 to 3 hours at a temperature of about 20° to about 80° C. The product is readily isolated by normal methods, for instance by filtering any solids and removing the reaction solvent by evaporation. The product can be purified if desired by routine methods, for instance crystallization from organic solvents such as ethyl acetate, dicholoromethane, hexane, and the like, as well as chromatography over solid supports such as silica gel. The compounds of the invention typically are solids which are readily crystallized.

Scheme II illustrates a typical acylation of a 2,7-diamino-6-(aryl)-pyrido[2,3-d]pyrimidine using a two-fold or larger excess of acetic anhydride with heating to prepare the diacylated product, for example an N-[2-acetylamino-6-(aryl)-pyrido[2,3-d]pyrimidin-7-yl]-acetamide. More generally, diacylated compounds of this type can be prepared by this method starting from the appropriate 2,7-diamino-6-(aryl)-pyrido-[2,3-d]pyrimidine compounds and treating them with excess acylating reagents such as acid anhydrides, mixed acid anhydrides, or activated acyl derivatives such as acid chlorides and sulfonyl chlorides. The reaction is generally carried out at a temperature between about 20° C. and 200° C. The addition of organic or inorganic bases such as triethylamine and sodium hydroxide may be desired to scavenger acid byproducts produced during the course of the reaction. The diacylated product is readily isolated and purified by chromatography or crystallization as described above.

Scheme III illustrates the preparation of a 6-(aryl)-$N^7$-alkyl-pyrido[2,3-d]pyrimidine-2,7-diamine in several steps starting with a 2,7-diamino-6-(aryl)-pyrido[2,3-d] pyrimidine which can be prepared by the method of U.S. Pat. No. 3,534,039. Treatment of the starting material with aqueous mineral acid under reflux conditions provides the hydrolysis product 2-amino-6-(aryl)-pyrido[2,3-d]pyrimidin-7-ol. Reaction of the 2-amino-6-(aryl)-pyrido[2,3-d]pyrimidin-7-ol with thionyl chloride under Vilsmeier-Haack conditions affords the chloro-formamidine product N'-(7-chloro-6-(aryl)-pyrido[2,3-d]pyrimidin-2-yl)-N,N-dimethyl-formamidine. This reactive intermediate can be directly reacted with nucleophilic reagents such as amines to give an $N^7$-alkyl-6-(aryl)-pyrido[2,3-d]-pyrimidine-2,7-diamine. Alternatively, the formamidine functionality can be removed by alcoholysis to provide the 7-chloro derivative, i.e., a 2-amino-7-chloro-6-(aryl)-pyrido[2,3-d]pyrimidine. Reaction of the 7-chloro intermediate with nucleophilic reagents such as an alkylamine provides the corresponding 6-(aryl)-$N^7$-alkyl-pyrido[2,3-d]pyrimidine-2,7-diamine.

Scheme IV describes the preparation of a 3-(aryl)-[1,6] naphthyridine-2,7-diamine and represents a general methodology for the preparation of these compounds. The hydrogenolysis of 6-bromo-2,4-diamino-5-cyanopyridine (*JACS,* 80:2838–2840 (1958)) affords the intermediate 2,4-diamino-5-cyanopyridine. The subsequent hydrogenation of the cyanopyridine compound, for example, in a mixture of formic acid-water employing Raney nickel catalyst, provides a key versatile intermediate 2,4-diamino-5-pyridine-carboxaldehyde. The aldehyde is then condensed with an aryl acetonitrile as described in Scheme IV to provide a 3-(aryl)-[1,6]naphthyridine-2,7-diamine. The condensation reaction is accomplished in the presence of an alkoxide base, for example, sodium ethoxide or sodium 2-ethoxyethoxide, which can be generated in situ by the addition of sodium metal or sodium hydride to ethanol or 2-ethoxyethanol. Scheme IV describes a general methodology for the preparation of the 3-(aryl)-[1,6]naphthyridine-2,7-diamines of this invention.

Scheme V illustrates the direct dialkylation of a 6-aryl-pyrido[2,3-d]pyrimidine-2,7-diamine (U.S. Pat. No. 3,534,039) with an alkylamine in a bomb at high temperature to afford an $N^2,N^7$-dialkyl-6-aryl-pyrido[2,3-d]pyrimidine-2,7-diamine. Generally, this reaction is carried out using neat amine reagents such as isobutylamine and n-hexylamine, at a temperature such as 150–300° C. in a bomb apparatus.

Scheme VI illustrates the synthesis of compounds of Formula I wherein $R_1$ can be an aminoalkyl group such as diethylaminopropyl. A 6-(aryl)-2,7-diamino-pyrido[2,3-d]pyrimidine can be reacted directly with an amine nucleophile such as an aminoalkylamine (e.g., $H_2N$ alkyl-$NR_5R_6$), generally in a bomb and in the presence of an acid such as sulfamic acid, to afford an aminoalkyl substituted compound of the invention. The compound can be further acylated, if desired, by routine methods. The compounds are readily isolated and purified by common methodologies such as crystallization and chromatography.

Scheme VII illustrates the synthesis of compounds of Formula I wherein $R_3$ and $R_4$ are taken together with the nitrogen to which they are attached to form a cyclic ring. The ring can include another heteroatom such as nitrogen, oxygen, or sulfur. In Scheme VII, a diaminopyridopyrimidine is reacted with a halo ethyl isocyanate to produce an imidazolidinone. The reaction generally is carried out in an organic solvent such as dimethylformamide, and normally in the presence of a base such as sodium hydride. The reaction typically is complete in about 8 to 16 hours when carried out at about 30° C. The product is readily isolated and purified by routine methods.

The above reaction also produces compounds of Formula I wherein $R_1$ or $R_3$ is an acyl analog of the formula

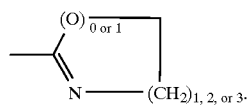

Scheme VIIa illustrates the reaction. The product can be isolated by routine methods such as chromatography, fractional crystallization, and the like.

Another group of compounds provided by the invention are amidines, compounds of Formula I wherein $R_1$ and $R_2$ together with the nitrogen to which they are attached, and $R_3$ and $R_4$ together with the nitrogen to which they are attached, can be a group having the formula

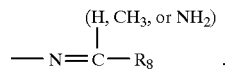

Scheme VIII illustrates the synthesis of typical pyridopyrimidine amidines which can be produced by reacting an amino pyridopyrimidine with an acetal of an amide or cyclic amide, for example, the dimethyl acetal of N,N-dimethylformamide, or the dimethylacetal of N-methylpyrrolidone. The reaction typically is carried out by mixing an amino pyridopyrimidine with about an equimolar quantity or excess of an acetal in a mutual solvent such as dimethylformamide, dimethylsulfoxide, tetrahydrofuran, or the like. The reaction generally is complete with about 3 to 6 hours when carried out at a temperature of about 5° C. to about 50° C. The product is readily isolated by routine procedures and can be purified, if desired, by normal techniques such as chromatography, crystallization, and the like.

The invention also provides amino pyrido-pyrimidines wherein the amino group is substituted with an aryl Ar', for example a phenyl, substituted phenyl, pyridyl, thiazolyl, pyrimidyl, and the like. Preferred N-aryl compounds have the formula

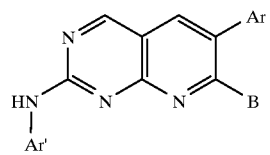

where Ar, Ar', and B are as defined above. Such compounds can be prepared by any of several methods, for example, as described in Schemes IX and X.

In Scheme IX, a pyridopyrimidine substituted with an alkylthio, alkyl sulfoxide or alkyl sulfone, for example at the 2-position, is reacted with an aryl amine (e.g., Ar'$NH_2$), to effect displacement of the thio- sulfoxide or sulfone substituent, to produce the corresponding N-aryl amino pyridopyrimidine. The displacement reaction generally is carried out in an organic solvent such as dimethylformamide, normally at a temperature of about 20° C. to about 80° C. The reaction generally is complete after about 3 to about 8 hours, and the product is readily isolated by adding the reaction mixture to water and extracting the product into a solvent such as methylene chloride, or the like.

Scheme X illustrates the synthesis of N-aryl amino pyridopyrimidines starting from a suitably substituted pyrimidine, e.g., 4-amino-2-chloropyrimidine-5-carbonitrile. The halo group is displaced by reaction with an aryl amine (Ar'$NH_2$) to give the corresponding 2-N-aryl aminopyrimidine, having a cyano group at the 5-position. The cyano group is converted to an aldehyde by reduction with Raney nickel in water and formic acid, and the resulting 2-arylamino-4-amino-pyrimidine-5-carboxaldehyde is reacted with an aryl acetonitrile (e.g., phenylacetonitrile, 2-pyridyl-acetonitrile, or the like) in the manner described in Scheme IV to provide the corresponding N-aryl-amino-pyridopyrimidine of the invention.

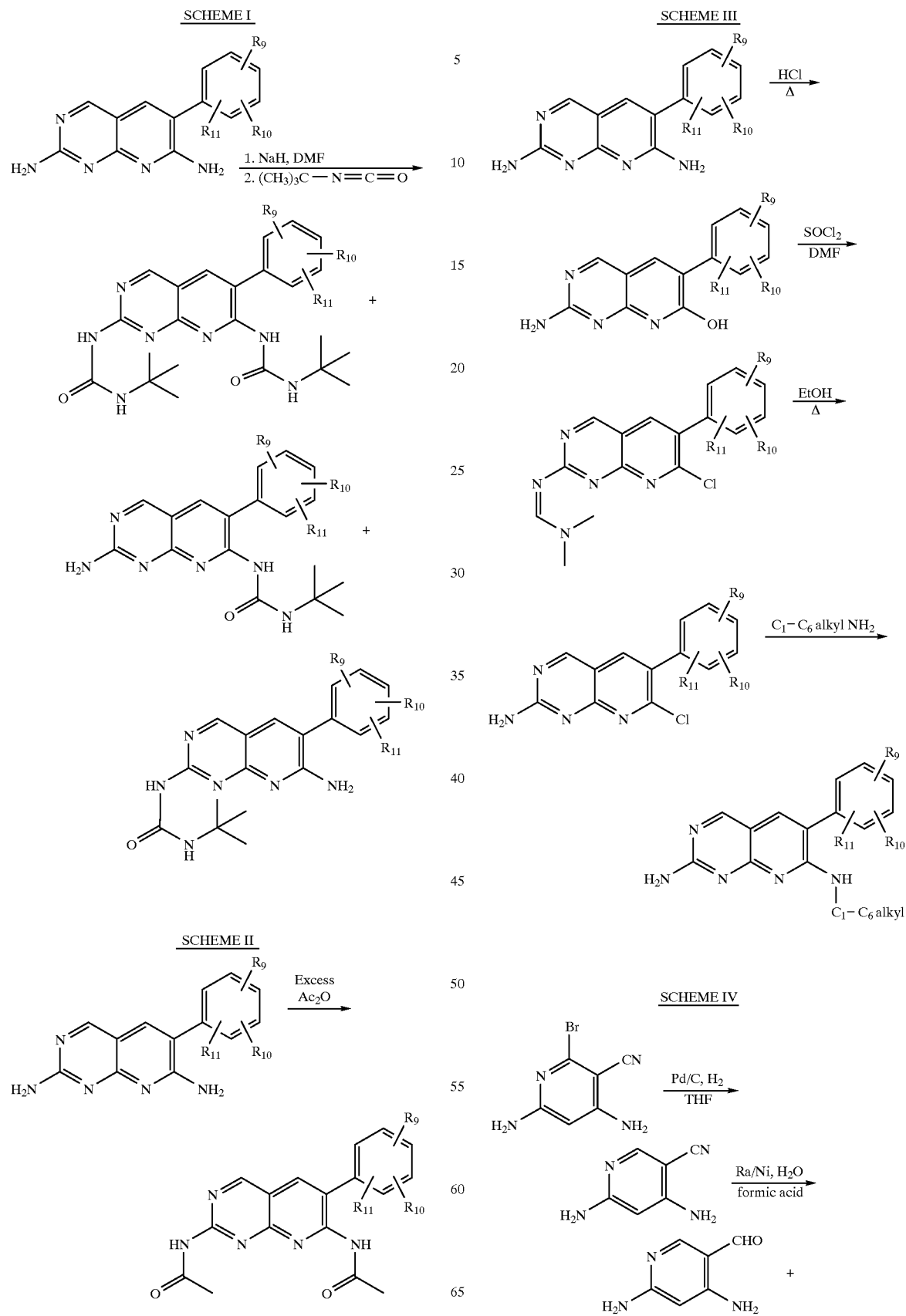

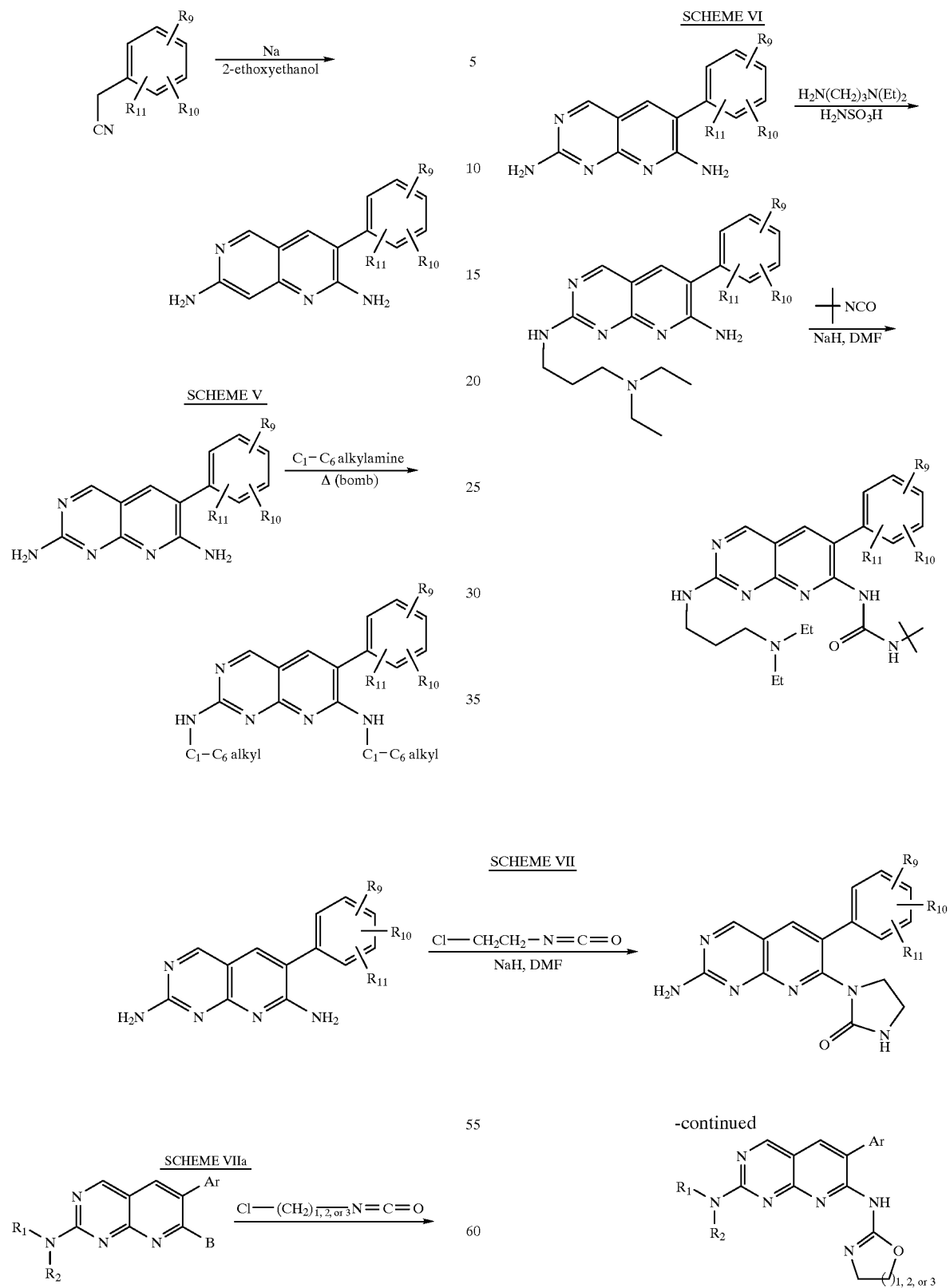

SCHEME VIII
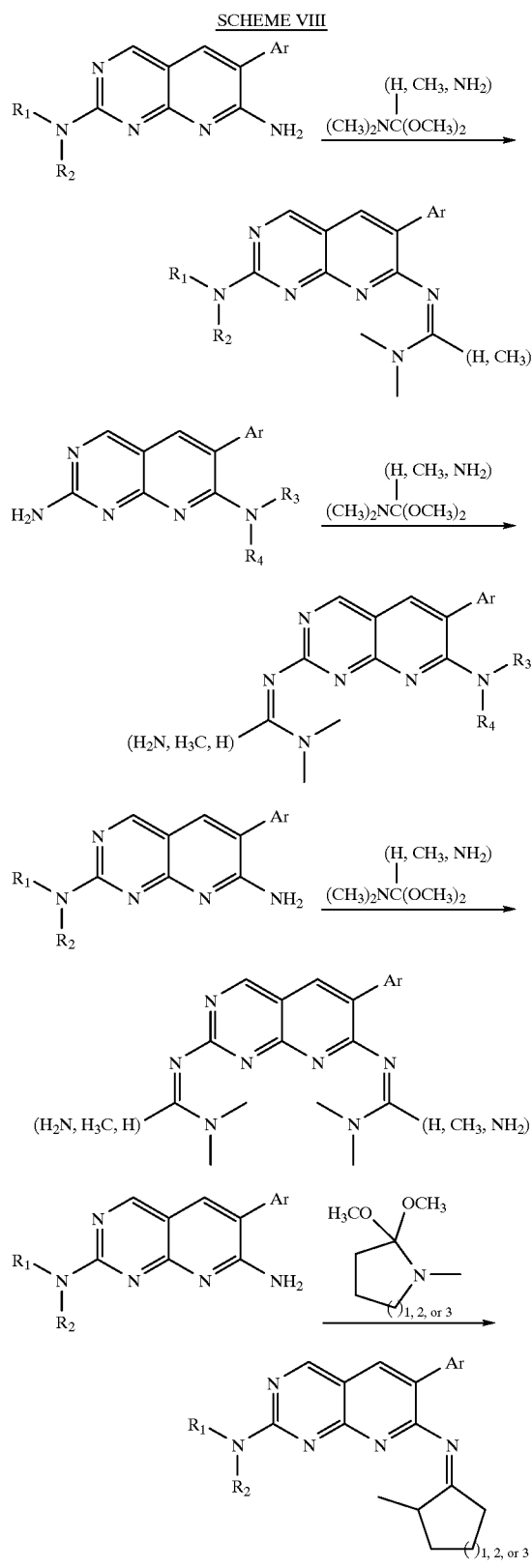
SCHEME IX
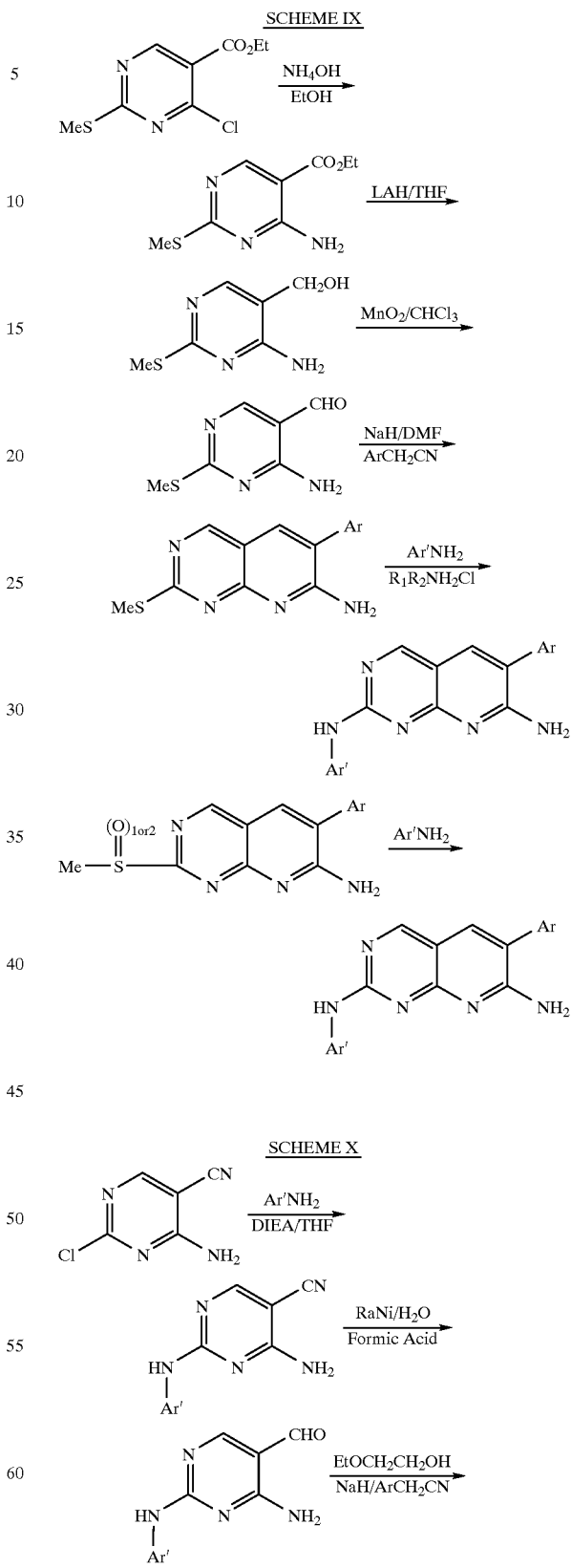
SCHEME X

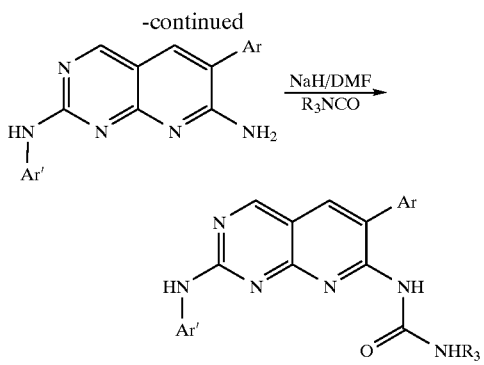

The compounds of Formula I are valuable inhibitors of protein tyrosine kinases and possess therapeutic value as cellular antiproliferative agents for the treatment of proliferative disorders. These compounds are potent inhibitors of one or more of the protein kinases, PDGF, FGF, EGF, V-src, and C-src. The invention compounds are thus useful in treating atherosclerosis, restenosis, and cancer. Specific tumors to be treated with the compounds include small-cell lung carcinoma such as that described in *An. Rev. Respir. Dis.*, 142:554–556 (1990); human breast cancer as described in *Cancer Research*, 52:4773–4778 (1992); low grade human bladder carcinomas of the type described in *Cancer Research*, 52:1457–1462 (1992); human colorectal cancer as discussed in *J. Clin. Invest.*, 91:53–60 (1993); and in *J. Surg. Res.*, 54:293–294 (1993). The compounds also are useful as antibiotics against bacteria such as *Streptococcus pneumoniae*. For instance, the compounds of Examples 9 and 18 exhibited activity against this Gram+bacterial strain when evaluated in standard in vitro assays. The compounds additionally are useful as herbicides against a wide variety of undesirable plants such as broad leaf weeds and grasses.

The compounds of the present invention can be formulated and administered in a wide variety of oral and parenteral dosage forms, including transdermal and rectal administration. It will be recognized to those skilled in the art that the following dosage forms may comprise as the active component, either a compound of Formula I or a corresponding pharmaceutically acceptable salt or solvate of a compound of Formula I.

A further embodiment of this invention is a pharmaceutical formulation comprising a compound of Formula I together with a pharmaceutically acceptable carrier, diluent, or excipient therefor. For preparing pharmaceutical compositions with the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid such as talc or starch which is in a mixture with the finely divided active component.

In tablets, the active component is mixed with the carrier having the necessary binding properties in suitable proportions and compacted in the shape and size desired.

The formulations of this invention preferably contain from about 5% to about 70% of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. A preferred form for oral use are capsules, which include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water-propylene glycol solutions. For parenteral injection, liquid preparations can be formulated in solution in aqueous polyethylene glycol solution, isotonic saline, 5% aqueous glucose, and the like.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with a viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Waxes, polymers, and the like can be utilized to prepare sustained-release dosage forms. Also, osmotic pumps can be employed to deliver the active compound uniformally over a prolonged period.

The pharmaceutical preparations of the invention are preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The therapeutically effective dose of a compound of Formula I will generally be from about 1 mg to about 100 mg/kg of body weight per day. Typical adult doses will be about 50 to about 800 mg per day. The quantity of active component in a unit dose preparation may be varied or adjusted from about 0.1 mg to about 500 mg, preferably about 0.5 mg to 100 mg according to the particular application and the potency of the active component. The composition can, if desired, also contain other compatible therapeutic agents. A subject in need of treatment with a compound of Formula I will be administered a dosage of about 1 to about 500 mg per day, either singly or in multiple doses over a 24-hour period.

The compounds of this invention have been evaluated in standard assays which are utilized to determine inhibition of tyrosine kinase. One such assay was conducted as follows: Purification of Epidermal Growth Factor Receptor Tyrosine Kinase Human EGF receptor tyrosine kinase was isolated from A431 epidermoid carcinoma cells by the following methods. Cells were grown in roller bottles in 50% Delbuco's Modified Eagle and 50% HAM F-12 nutrient media (Gibco) containing 10% fetal calf serum Approximately $10^9$ cells were lysed in two volumes of buffer containing 20 mM 2-(4N-[2-hydroxyethyl]-piperazin-1-yl)ethanesulfonic acid, pH 7.4, 5 mM ethylene glycol bis(2-aminoethyl ether) N,N,N',N'-tetraacetic acid, 1% Triton X-100, 10% glycerol, 0.1 mM sodium orthovanadate, 5 mM sodium fluoride, 4 mM pyrophosphate, 4 mM benzamide, 1 mM dithiothreitol, 80 $\mu$g/mL aprotinin, 40 $\mu$g/mL leupeptin, and 1 mM phenylmethylsulfonyl fluoride. After centrifugation at 25,000× g for 10 minutes, the supernatant was equilibrated for 2 hours at 4° C. with 10 mL of wheat germ agglutinin sepharose that was previously equilibrated with 50 mM Hepes, 10% glycerol, 0.1% Triton X-100 and 150 mM NaCl, pH 7.5, (equilibration buffer). Contaminating proteins were washed from the resin with 1 M NaCl in equilibration buffer, and the enzyme was eluted with 0.5 M N-acetyl-1-D-glucosamine in equilibration buffer.

Determination of $IC_{50}$ Values

Enzyme assays for $IC_{50}$ determinations were performed in a total volume of 0.1 mL, containing 25 mM Hepes, pH 7.4, 5 mM $MgCl_2$, 2 mM $MnCl_2$, 50 $\mu$M sodium vanadate, 5–10 ng of EGF receptor tyrosine kinase, 200 $\mu$M of a substrate peptide, e.g., (Ac-Lys-His-Lys-Lys-Leu-Ala-Glu-Gly-Ser-Ala-Tyr$^{472}$-Glu-Glu-Val-NH$_2$), (Wahl M. I., et al., *J. Biol. Chem.*, 265:3944–3948 (1990)), 10 $\mu$M ATP containing 1 $\mu$Ci of [$^{32}$P]ATP, and incubated for 10 minutes at room temperature. The reaction was terminated by the addition of 2 mL of 75 mM phosphoric acid and passed through a 2.5-cm phosphocellulose filter disc to bind the peptide. The filter was washed five times with 75 mM phosphoric acid and placed in a vial along with 5 mL of scintillation fluid (Ready gel Beckman).

PDGF and FGF Receptor Tyrosine Kinase Assays

Full length cDNAs for the mouse PDGF-$\beta$ and human FGF-1 (flg) receptor tyrosine kinases were obtained from J. Escobedo and prepared as described in *J. Biol. Chem.*, 262:1482–1487 (1991), and PCR primers were designed to amplify a fragment of DNA that codes for the intracellular tyrosine kinase domain. The fragment was melded into a baculovirus vector, cotransfected with AcMNPV DNA, and the recombinant virus isolated. SF9 insect cells were infected with the virus to overexpress the protein, and the cell lysate was used for the assay. The assay was performed in 96-well plates (100 $\mu$L/incubation/well), and conditions were optimized to measure the incorporation of $^{32}$p from $\gamma^{32}$P-ATP into a glutamate-tyrosine co-polymer substrate. Briefly, to each well was added 82.5 $\mu$L of incubation buffer containing 25 mM Hepes (pH 7.0), 150 mM NaCl, 0.1% Triton X-100, 0.2 mM PMSF, 0.2 mM $Na_3VO_4$, 10 mM $MnCl_2$, and 750 $\mu$g/mL of Poly (4:1) glutamate-tyrosine followed by 2.5 $\mu$L of inhibitor and 5 $\mu$L of enzyme lysate (7.5 $\mu$g/$\mu$L FGF-TK or 6.0 $\mu$g/$\mu$L PDGF-TK) to initiate the reaction. Following a 10 minute incubation at 25° C., 10 $\mu$L of $\gamma^{32}$P-ATP (0.4 $\mu$Ci plus 50 $\mu$M ATP) was added to each well and samples were incubated for an additional 10 minutes at 25° C. The reaction was terminated by the addition of 100 $\mu$L of 30% trichloroacetic acid (TCA) containing 20 mM sodium pyrophosphate and precipitation of material onto glass fiber filter mats (Wallac). Filters were washed three times with 15% TCA containing 100 mM sodium pyrophosphate and the radioactivity retained on the filters counted in a Wallac 1250 Betaplate reader. Nonspecific activity was defined as radioactivity retained on the filters following incubation of samples with buffer alone (no enzyme). Specific enzymatic activity was defined as total activity (enzyme plus buffer) minus nonspecific activity. The concentration of a compound that inhibited specific activity by 50% ($IC_{50}$) was determined based on the inhibition curve.

V-src and C-src Kinase Assays

V-src or C-src kinase is purified from baculovirus infected insect cell lysates using an antipeptide monoclonal antibody directed against the N-terminal 2–17 amino acids. The antibody, covalently linked to 0.65-$\mu$m latex beads, is added to a suspension of insect cell lysis buffer comprised of 150 mM NaCl, 50 mM Tris pH 7.5, 1 mM DTT, 1% NP-40, 2 mM EGTA, 1 mM sodium vanadate, 1 mM PMSF, 1 $\mu$g/mL each of leupeptin, pepstatin, and aprotinin. Insect cell lysate containing either the c-src or v-src protein is incubated with these beads for 3–4 hours at 4° C. with rotation. At the end of the lysate incubation, the beads are rinsed 3 times in lysis buffer, resuspended in lysis buffer containing 10% glycerol, and frozen. These latex beads are thawed, rinsed three times in assay buffer which is comprised of 40 mM tris pH 7.5, 5 mM $MgCl_2$, and suspended in the same buffer. In a Millipore 96-well plate with a 0.65 $\mu$m polyvinylidine membrane bottom are added the reaction components: 10-$\mu$L v-src or c-src beads, 10 $\mu$L of 2.5 mg/mL poly GluTyr substrate, 5 $\mu$M ATP containing 0.2 $\mu$Ci labeled $^{32}$P-ATP, 5 $\mu$L DMSO containing inhibitors or as a solvent control, and buffer to make the final volume 125 $\mu$L. The reaction is started at room temperature by addition of the ATP and quenched 10 minutes later by the addition of 125 $\mu$L of 30% TCA, 0.1 M sodium pyrophosphate for 5 minutes on ice. The plate is then filtered and the wells washed with two 250-$\mu$L aliquots of 15% TCA, 0.1 M pyrophosphate. The filters are punched, counted in a liquid scintillation counter, and the data examined for inhibitory activity in comparison to a known inhibitor such as erbstatin. The method is described more fully in *J. Med. Chem.*, 37:598–609 (1994).

Cell Culture

Rat aorta smooth muscle cells (RASMC) were isolated from the thoracic aorta of rats and explanted according to the method of Ross, *J. Cell. Biol.*, 30:172–186 (1971). Cells were grown in Dulbecco's modified Eagle's medium (DMEM, Gibco) containing 10% fetal calf serum (FBS, Hyclone, Logan, Utah), 1% glutamine (Gibco) and 1% penicillin/streptomycin (Gibco). Cells were identified as smooth muscle cells by their "hill and valley" growth pattern and by fluorescent staining with a monoclonal antibody specific for SMC $\mu$-actin (Sigma). RASMC were used between passages 5 and 20 for all experiments. Test compounds were prepared in dimethylsulfoxide (DMSO) in order to achieve consistency in the vehicle and to ensure compound solubility. Appropriate DMSO controls were simultaneously evaluated with the test compounds.

[$^3$H]-Thymidine Incorporation Assay

RASMC were plated into a 24-well plate (30,000 cells/well) in DMEM with 10% FBS. After 4 days, cells reached confluence and were made quiescent by incubation in DMEM/F12 medium (Gibco) containing 0.2% FBS for another 2 days. DNA synthesis was induced by incubating cells for 22 hours with either PDGF-BB, bFGF, or FBS, plus test compound in 0.5 mL/well serum-substituted medium (DMEM/F12+1% CPSR-2 from Sigma). After 18 hours, 0.25 $\mu$Ci/well [$^3$H]-thymidine was added. Four hours later, the incubation was stopped by removing the radioactive media, washing the cells twice with 1 mL cold phosphate-buffered saline, and then washing 2 times with cold 5% trichloroacetic acid. The acid-insoluble fraction was lysed in 0.75 mL 0.25 N NaOH and the radioactivity determined by liquid scintillation counting. $IC_{50}$ values were determined graphically.

PDGF Receptor Autophosphorylation

RASMC were grown to confluency in 100 mm dishes. Growth medium was removed and replaced with serum-free medium and cells were incubated at 37° C. for an additional 24 hours. Test compounds were then added directly to the medium and cells incubated for an additional 2 hours. After 2 hours, PDGF-BB was added at a final concentration of 30 ng/mL for 5 minutes at 37° C. to stimulated autophosphorylation of the PDGF receptor. Following growth factor treatment, the medium was removed, and cells were washed with cold phosphate-buffered saline and immediately lysed with 1 mL of lysis buffer (50 mM HEPES[pH 7.5], 150 mM NaCl, 10% glycerol, 1% Triton X-100, 1 mM EDTA, 1 mMEGTA, 50 mM NaF, 1 mM sodium orthovanadate, 30 mM p-nitrophenyl phosphate, 10 mM sodium pyrophosphate, 1 mM phenylmethyl sulfonyl fluoride, 10 μg/mL aprotinin, and 10 μg/mL leupeptin). Lysates were centrifuged at 10,000× g for 10 minutes. Supernatants were incubated with 10 μL of rabbit anti-human PDGF type AB receptor antibody (1:1000) for 2 hours. Following the incubation, protein-A-sepharose beads were added for 2 hours with continuous mixing, and immune complexes bound to the beads washed 4 times with 1 mL lysis wash buffer. Immune complexes were solubilized in 30 μL of Laemmli sample buffer and electrophoresed in 4–20% SDS polyacrylamide gels. Following electrophoresis, separated proteins were transferred to nitrocellulose and immunoblotted with anti-phosphotyrosine antiserum. Following incubation with [$^{125}$I]-protein-A, the levels of tyrosine phosphorylated proteins were detected by phosphorimage analysis and protein bands quantitated via densitometry. IC$_{50}$ values were generated from the densitometric data.

The following Tables I and II present biological data for representative compounds of the invention when analyzed in the foregoing assays.

TABLE I

Inhibition of Protein Tyrosine Kinases
(μM IC$_{50}$ or (% Inhibition) at 50 μM)

| Example | PDGF | FGF | EGF | V-src | C-src |
|---|---|---|---|---|---|
| 1 | 21.2 | 2.99 | | (−2.4%) | 0.21 |
| 2 | 10.2 | 1.60 | (52.3%) | (27.4%) | 19.5 |
| 3 | 1.25 | 0.140 | 1.17 | (46.8%) | 0.22 |
| 4 | (31.9%) | (21.5%) | (36.65%) | (3.1%) | (33.6%) |
| 5 | 0.466 | 1.40 | 0.928 | (23.3%) | 0.407 |
| 6 | 0.34 | 0.397 | 0.457 | (39.8%) | 0.11 |
| 7 | (33.5%) | 17.9 | (25.15%) | (7.6%) | 2.3 |
| 9 | 25.1 | 10.56 | | | 18.3 |
| 13 | (18.2%) | 30.3 | | (21.2%) | (15.9%) |
| 16 | 10.72 | 9.21 | 7.08 | (10.3%) | 1.38 |
| 17 | 27.0 | 4.50 | 7.22 | (5.3%) | 2.76 |
| 18 | 21.3 | 1.19 | 18.2 | (21.4%) | 0.514 |
| 19 | (47.7%) | 16.93 | (26.1%) | (5.2%) | (52.8%) |
| 20 | 46.1 | 2.38 | | (51.7%) | 0.748 |
| 21 | 0.66 | 0.0824 | 6.97 | (49.4%) | 0.073 |
| 22 | 1.3 | 0.128 | (90.4%) | (46.9%) | 0.077 |
| 23 | 4.51 | 0.291 | (104.8%) | (10.2%) | 0.613 |
| 24 | 11.38 | 7.29 | (58.3%) | (15.6%) | 0.214 |
| 25 | 6.04 | 11.82 | (57.55%) | (0.0%) | 0.207 |
| 26 | 1.08 | 0.116 | | | 0.0395 |
| 28 | 0.676 | 0.075 | | | 0.117 |
| 30 | 1.78 | 0.264 | | | (46.8%) |
| 32 | 0.415 | 0.0739 | | | 5.0 |
| 34 | 0.349 | 0.0552 | | | 0.011 |
| 35 | 2.08 | (97.9%) | | | |
| 36 | 22.88 | 0.523 | | | 0.184 |
| 37 | 0.263 | 0.0401 | | | (106.5%) |
| 38 | 0.360 | 0.047 | | | 0.019 |
| 39 | 1.98 | 0.125 | | | 0.021 |
| 40 | 0.697 | 0.0574 | | | |

TABLE I-continued

Inhibition of Protein Tyrosine Kinases
(μM IC$_{50}$ or (% Inhibition) at 50 μM)

| Example | PDGF | FGF | EGF | V-src | C-src |
|---|---|---|---|---|---|
| 41 | 0.793 | 0.139 | | | 0.086 |
| 42 | 0.624 | 0.108 | | | 0.032 |
| 43 | 0.405 | 0.091 | | | 0.011 |
| 44 | 1.55 | 0.196 | | | 0.023 |
| 45 | 1.85 | 0.198 | | | 0.04 |
| 47 | 6.17 | 0.637 | | | 0.161 |
| 48 | 5.32 | 0.613 | | | 0.26 |
| 49 | 0.420 | 0.0535 | | | 0.024 |
| 50 | 2.60 | 0.305 | | | |
| 51 | 0.573 | 0.084 | | | 0.10 |
| 52 | 0.468 | 0.051 | | | 0.032 |
| 53 | 7.08 | 0.693 | | | 0.153 |
| 54 | 0.231 | 0.0954 | | | |
| 58 | 19.0 | 3.46 | | | (109.8%) |
| 59 | 0.838 | 0.072 | | | 0.085 |
| 60 | 35.9 | 13.0 | | | 1.57 |
| 61 | 45.6 | 7.85 | | | 0.764 |
| 63 | 7.01 | 0.543 | | | 1.78 |
| 64 | (13.0%) | (23.8%) | | | (0.0%) |
| 65 | (29.6%) | 17.0 | | | (95.0%) |
| 66 | 5.19 | 1.28 | | | 3.42 |
| 67 | 12.05 | 1.39 | | | 1.56 |
| 69 | 15.55 | 1.96 | | | 4.66 |
| 70 | 31.35 | 2.59 | | | 0.929 |
| 78 | 32.9 | 4.01 | | | 3.99 |
| 79 | 17.78 | 8.09 | (60.93%) | | |
| 80 | (22.9%) | 10.2 | | | |
| 81 | | | | (−20.3%) | (67.5%) |
| 82 | 4.67 | 3.71 | | | (77.6%) |
| 83 | 42.5 | 1.98 | | (−9.8%) | (53.6%) |
| 84 | 2.26 | 0.162 | | | 3.82 |
| 85 | 7.63 | 0.129 | | | 4.46 |
| 86 | 2.96 | 0.114 | | | 1.41 |
| 87 | 1.88 | 0.118 | | | (92.7%) |
| 88 | 0.711 | 0.148 | (34.4%) | | 0.213 |
| 89 | 0.857 | 0.111 | | | 0.036 |
| 90 | 8.01 | 11.46 | 22.75 | (16.8%) | 1.63 |
| 92 | (33.1%) | 2.01 | | (−10.1%) | (44.5%) |
| 93 | 6.05 | 0.343 | | | 4.17 |
| 94 | (11.5%) | 17.6 | | | |
| 95 | 41.6 | 0.605 | | | (0.0%) |
| 96 | 27.4 | 3.84 | | | |
| 97 | 1.73 | 0.34 | | | (28.9%) |
| 98 | (34.3%) | 1.80 | | | (0.5%) |
| 99 | (15.5%) | 0.708 | | | (17.1%) |
| 100 | (22.3%) | (27.1%) | | (6.0%) | (46.6%) |
| 101 | 4.48 | 11.22 | | | 19.3 |
| 102 | (44.4%) | 3.11 | | (−8.2%) | (0.8%) |
| 103 | 19.6 | 0.300 | | | 36.4 |
| 104 | 36.7 | 5.32 | | | |
| 105 | 0.618 | 0.181 | | | 0.214 |
| 106 | 4.8 | 0.361 | | | 0.236 |
| 107 | (20.5%) | (37.2%) | | (1.4%) | (37.0%) |
| 108 | 13.7 | 4.48 | | | 5.66 |
| 109 | (23.6%) | (10.3%) | | | |
| 110 | 11.5 | 12.8 | | | (27.5%) |
| 111 | 23.3 | (47.7%) | | (−26.4%) | (15.7%) |
| 112 | 1.26 | 0.128 | | | 0.077 |
| 113 | 1.09 | 0.077 | | | 0.078 |
| 114 | 23.9 | 19.2 | | | |
| 115 | 2.63 | 1.24 | | | 0.024 |
| 116 | 0.804 | 0.335 | | | 0.098 |
| 117 | 2.79 | 0.135 | | | (100%) |
| 118 | 1.92 | 0.126 | | | |
| 119 | 62.4 | 7.71 | | | |
| 120 | 3.84 | 3.27 | | | 42.7 |
| 121 | (21.8%) | 0.142 | | | |
| 122 | 1.46 | 0.171 | | | |
| 123 | 0.26 | 0.045 | | | 0.029 |
| 124 | 0.253 | 0.059 | | | 0.026 |

TABLE II

Cellular Assays (IC$_{50}$ = μM)

| Example | Inhibition of PDGF Stimulated Receptor Auto Phosphorylation (IC$_{50}$ = μM) | Inhibition of Growth Factor Stimulated Uptake of [$^3$H]-thymidine (IC$_{50}$ = μM) |
|---|---|---|
| 3 | 0.97 | 2.7 (PDGF), 0.9 (FGF) |
| 124 | 0.245 | 0.55 (PDGF), 0.93 (FGF) |
| 51 | 0.365 | |
| 123 | 0.296 | <0.30 (PDGF), 0.32 (FGF) |
| 52 | 0.241 | 0.45 (PDGF), 0.40 (FGF) |
| 69 | 6.46 | |
| 113 | 1.1 | |
| 89 | 1.63 | |
| 59 | 1.19 | |
| 67 | 9.42 | |
| 115 | 5.13 | |
| 66 | 5.29 | |
| 116 | 0.91 | |
| 28 | 1.38 | |
| 114 | 15.86 | |
| 112 | 1.08 | |
| 22 | 3.73 | |
| 21 | 1.8 | |
| 6 | 0.35 | |
| 90 | | >10 (PDGF), 20.0 (FGF) |

The invention compounds are especially useful for treating restenosis following balloon angioplasty of occluded arteries. Restenosis occurs in about 40% of individuals undergoing angioplasty of calcified arteries and is a major problem associated with this form of treatment of patients suffering from such cardiac condition. The invention compounds demonstrate good activity when evaluated in standard tests such as described below.

Balloon Angioplasty of Rat Carotid Arteries

Male Sprague-Dawley rats (350–450 g) are divided into two treatment groups: one group of rats (n=10) are treated with drug (100 mg/kg PO, BID) and the second group received vehicle (2 mL/kg PO, BID (n=10)). All animals were pretreated for 2 days prior to surgery and continued to receive daily drug treatment postinjury until sacrificed.

Balloon injury in rat carotid arteries were performed according to the following protocol Rats were anesthetized with Telazol (0.1 mL/100 g IM), and the carotid artery exposed via an anterior mid-line incision on the neck. The carotid artery was isolated at the bifurcation of the internal and external carotid arteries. A 2F embolectomy catheter was inserted in the external carotid artery and advanced down the common carotid to the level of the aortic arch. The balloon was inflated and the catheter is dragged back to the point of entry and then deflated. This procedure is repeated two more times. The embolectomy catheter was then removed and the external carotid artery was ligated leaving flow intact through the internal carotid artery. Surgical incisions were closed, and the animal was allowed to recover from anesthesia before being returned to its home cage.

At various time points postinjury animals were euthanized with CO$_2$ inhalation, and the carotid artery was perfusion fixed and processed for histologic examination. Morphologic determination of lesion size was made by measuring the area of the carotid artery intima expressed as a ratio of the media in individual animals. Up to 16 sections were prepared from each animal to give a uniform representation of lesion size down the length of the carotid artery. The cross-sectional areas of the blood vessels were quantified using an image analysis program from Princeton Gamma Tech (Princeton, N.J.).

The following examples illustrate methods for preparing intermediate and final products of the invention. They are not intended to limit the scope of the invention. Mixtures of solvents are volume/volume.

EXAMPLE 1

2,7-Diamino-6-(2,6-dichlorophenyl)-pyrido[2,3-d]-pyrimidine (Prepared by the method of U.S. Pat. No. 3,534,039). To a solution of sodium 2-ethoxyethoxide prepared from 0.14 g of sodium and 60 mL of 2-ethoxyethanol was added 2.07 g of 2,4-diamino-5-pyrimidinecarboxaldehyde and 2.79 g of 2,6-dichlorophenylacetonitrile. The mixture is heated at reflux for 4 hours, cooled, and the insoluble product washed with diethylether to give 2,7-diamino-6-(2,6-dichlorophenyl)-pyrido[2,3-d]pyrimidine, mp 325–332° C. (MS).

EXAMPLE 2

1-tert-Butyl-3-[7-(3-tert-butylureido)-6-(2,6-dichlorophenyl)-pyrido[2,3-d]pyrimidin-2-yl]urea To a slurry of 3.0 g of 2,7-diamino-6-(2,6-dichlorophenyl)-pyrido[2,3-d]pyrimidine from above in 45 mL of DMF is added 0.48 g sodium hydride (50% in mineral oil) portionwise. The mixture is stirred for 1 hour, 1.0 g of tert-butylisocyanate added, and the reaction mixture stirred at ambient temperature for 16 hours. The reaction mixture is filtered to remove a small amount of insoluble material and the filtrate diluted with 500 mL of water. The insoluble product is collected by filtration, washed with water, then ether, and dried in air on the filter. The product is purified by silica gel chromatography eluting with a gradient of 0–1% methanol in chloroform to afford, after crystallization from ethanol, 0.7 g of 1-tert-butyl-3-[7-(3-tert-butylureido)-6-(dichlorophenyl)-pyrido[2,3-d]pyrimidin-2-yl]urea, mp 200° C. dec.

Analysis calculated for $C_{23}H_{22}C_{12}N_7O_2 \cdot 0.1 H_2O$:

Theory: C, 54.57; H, 5.42; N, 19.37; H$_2$O, 0.36.

Found: C, 54.05; H, 5.43; N, 19.08; H$_2$O, 0.37.

EXAMPLE 3

1-[2-Amino-6-(2,6-dichlorophenyl)-pyrido[2,3-d]-pyrimidin-7-yl]-3-tert-butylurea Continued elution from Example 2 above afforded 1.5 g of 1-[2-amino-6-(2,6-dichlorophenyl)-pyrido-[2,3-d] pyrimidin-7-yl]-3-tert-butylurea after crystallization from ethanol, mp 335° C.

Analysis calculated for $C_{18}H_{18}C_{12}N_6O \cdot 0.5 H_2O$:

Theory: C, 52.18; H, 4.62; N, 20.28; H$_2$O, 2.17.

Found: C, 51.90; H, 4.56; N, 20.01; H$_2$O, 2.39.

EXAMPLE 4

1-tert-Butyl-3-[7-(3-tert-butylureido)-6-o-tolyl-pyrido[2,3-d]pyrimidin-2-yl]urea A suspension of 0.5 g of 2,7-diamino-6-o-tolyl-pyrido[2,3-d]pyrimidine, prepared as described above in Example 1, in 10 mL of dimethylformamide is reacted with 0.16 g of 60% sodium hydride and stirred at ambient temperature for 1.5 hours. To the suspension is added 0.49 mL of t-butylisocyanate and the mixture stirred overnight at ambient temperature. The reaction mixture is filtered to remove insoluble salts and the filtrate evaporated under reduced pressure. The residue is diluted with water, the insoluble crude product collected by filtration and dried in vacuo. Crystallization from a hexane:ethyl acetate:dichloromethane mixture (3:2:5 v/v/v) afforded the title compound, mp 209–212° C. dec.

Analysis calculated for $C_{24}H_{31}N_7O_2 \cdot 0.3\ H_2O$:

Theory: C, 63.36; H, 7.00; N, 21.55.

Found: C, 63.37; H, 6.92; N, 21.16.

EXAMPLE 5

1-[2-Amino-6-o-tolyl-pyrido[2,3-d]pyrimidin-7-yl]-3-tert-butylurea

Prepared as described above in Example 2 starting from 2,7-diamino-6-o-tolyl-pyrido[2,3-d]pyrimidine to afford the title compound 1-[2-amino-6-o-tolyl-pyrido[2,3-d] pyrimidin-7-yl]-3-tert-butylurea, mp 285–290° C. dec; MS (CI).

EXAMPLE 6

1-[2-Amino-6-(2,6-dimethylphenyl)-pyrido[2,3-d]-pyrimidin-7-yl]-3-tert-butylurea Prepared as described above in Example 2 starting from 2,7-diamino-6-(2,6-dimethylphenyl)-pyrido[2,3-d]-pyrimidine to give the title compound 1-[2-amino-6-(2,6-dimethylphenyl)-pyrido[2,3-d]pyrimidin-7-yl]-3-tert-butylurea, mp 203–205° C. dec; CIMS (1% ammonia in methane) 365 (M+1, 50), 366 (M+2, 10), 84 (100).

EXAMPLE 7

N-[2-Acetylamino-6-(2,6-dichlorophenyl)-pyrido[2,3-d]-pyrimidin-7-yl]-acetamide

A mixture of 10 g of 2,7-diamino-6-(2,6-dichlorophenyl)-pyrido[2,3-d]pyrimidine prepared as described in Example 1 in 100 mL of acetic anhydride was refluxed for 2 hours. The reaction mixture was allowed to cool to room temperature and the excess acetic anhydride removed under vacuum. The residue was dissolved in ethanol, charcoaled, filtered, and cooled overnight at 0° C. The insoluble crude product was collected by filtration, washed with diethylether and dried in vacuo. The crude product was crystallized from boiling ethyl acetate using charcoal to give 2.7 g of an impure product, which was further purified by slurring in hot ethyl acetate and collecting the insoluble pure product (1.2 g), mp 223–225° C.

Analysis calculated for $C_{17}H_{13}Cl_2N_5O_2$:

Theory: C, 52.32; H, 3.36; N, 17.95.

Found: C, 51.92; H, 3.43; N, 17.78.

EXAMPLE 8

2-Amino-6-phenyl-pyrido[2,3-d]pyrimidin-7-ol

To a solution of 2 L of concentrated HCl and 1 L of water is added 300 g of the disulfate salt of 2,7-diamino-6-phenylpyrido[2,3-d]pyrimidine and the resulting mixture refluxed with stirring overnight The reaction mixture is cooled in an ice bath, filtered, and the insoluble product washed with water, followed by ethanol to give 149 g of the title compound 2-amino-6-phenyl-pyrido[2,3-d]pyrimidin-7-ol, mp 390–395° C. (darkens slowly above 350° C.).

EXAMPLE 9

$N^7$-Butyl-6-phenyl-pyrido[2,3-d]pyrimidine-2,7-diamine

To a mixture of 23.8 g of 2-amino-6-phenyl-pyrido-[2,3-d]pyrimidin-7-ol prepared above in Example 8, 250 mL of dichloromethane, and 77.5 mL of dimethylformamide was added dropwise with cooling 36 mL of thionyl chloride keeping the temperature below 15° C. Following complete addition, the suspension was heated to reflux with stirring for 5 hours. The solvents were removed in vacuo maintaining the temperature below 60° C. The resulting solid was added with cooling to 250 mL of n-butylamine and the suspension refluxed for 6 hours with stirring. The reaction mixture was allowed to cool to room temperature, filtered, and the volatile components of the filtrate removed on a rotary evaporator in vacuo. The viscous oil was partitioned between diethyl ether and water, the layers were separated, and the ethereal layer was washed with water. The organic layer was dried over anhydrous magnesium sulfate, filtered, and evaporated. The residue was partitioned between diethyl ether and dilute 1N HCl. The aqueous layer was washed three times with diethylether and made alkaline to pH 12 by addition of sodium hydroxide. The solid product was collected by filtration and dried in vacuo to afford 6.5 g of the title compound $N^7$-butyl-6-phenyl-pyrido[2,3-d]pyrimidine-2,7-diamine, mp 174–181° C. dec.

Analysis calculated for $C_{17}H_{19}N_5$:

Theory: C, 69.60; H, 6.53; N, 23.87.

Found: C, 69.53; H, 6.63; N, 24.37.

EXAMPLE 10

2-Amino-6-(4-methoxyphenyl)-pyrido[2,3-d]pyrimidin-7-ol

The title compound was prepared as described above in Example 8 starting from 2,7-diamino-6-(4-methoxyphenyl)-pyrido[2,3-d]pyrimidine (U.S. Pat. No. 3,534,039), mp 380–385° C. dec.

Analysis calculated for $C_{14}H_{12}N_4O_2 \cdot 0.75\ H_2O$:

Theory: C, 59.90; H, 4.42; N, 19.88.

Found: C, 60.10; H, 4.32; N, 19.64.

EXAMPLE 11

N'-(7-Chloro-6-(4-methoxyphenyl)-pyrido[2,3-d]-pyrimidin-2-yl)-N,N-dimethyl-formamidine To a mixture of 67.0 g of 2-amino-6-(4-methoxyphenyl)-pyrido[2,3-d]pyrimidin-7-ol from Example 10, 1 L of dichloromethane, and 155 mL of dimethylformamide was added dropwise with cooling 72 mL of thionyl chloride keeping the temperature below 15° C. The suspension was heated to reflux with stirring for 6 hours. The reaction mixture was filtered and the filtrate evaporated in vacuo maintaining the temperature below 60° C. The resulting residue was dissolved in ice water and aqueous sodium hydroxide added with ice. The product was taken up in chloroform, washed with water, dried over anhydrous potassium carbonate, and evaporated. The residue was slurried with acetonitrile and the insoluble product collected by filtration to afford 31 g of the title compound N'-(7-chloro-6-(4-methoxyphenyl)-pyrido[2,3-d]pyrimidin-2-yl)-N,N-dimethyl-formamidine. The product was used in the next step without further purification.

EXAMPLE 12

2-Amino-7-chloro-6-(4-methoxyphenyl)-pyrido[2,3-d]-pyrimidine

A mixture of 10 g of N'-(7-chloro-6-(4-methoxyphenyl)-pyrido[2,3-d]pyrimidin-2-yl)-N,N-dimethyl-formamidine from Example 11 and 500 mL of 95% ethanol was refluxed for 3 hours. The solution was concentrated in vacuo and the precipitate collected by filtration. Crystallization from ethanol afforded 2.7 g of the title compound 2-amino-7-chloro-6-(4-methoxyphenyl)-pyrido[2,3-d]pyrimidine, mp 275–280° C. dec.

Analysis calculated for $C_{14}H_{11}N_4ClO$:
Theory: C, 58.64; H, 3.87; N, 19.54.
Found: C, 58.70; H, 3.94; N, 19.51.

EXAMPLE 13

6-(4-Methoxyphenyl)-$N^7$-methyl-pyrido[2,3-d]-pyrimidine-2,7-diamine

A mixture of 3.4 g of 2-amino-7-chloro-6-(4-methoxyphenyl)-pyrido[2,3-d]pyrimidine from Example 12, 40 mL of anhydrous methylamine, and 10 mL of methanol were heated in a bomb on a steam bath for 4 hours. After cooling, the suspension was washed out of the bomb with 50 mL of methanol/water (50:50) and the solvents were evaporated in vacuo. The solid residue was slurried with 50 mL of water, filtered, and crystallized from ethanol to afford 2.2 g of the title compound 6-(4-methoxyphenyl)-$N^7$-methyl-pyrido[2,3-d]-pyrimidine-2,7-diamine, mp 270–275° C. dec.

Analysis calculated for $C_{15}H_{15}N_5O$:
Theory: C, 64.03; H, 5.37; N, 24.90.
Found: C, 63.82; H, 5.17; N, 24.94.

EXAMPLE 14

2,4-Diamino-5-cyanopyridine

A suspension of 21.3 g of 6-bromo-2,4-diamino-5-cyanopyridine (*JACS*, 80:2838–2840 (1958)) and 1 g of 20% palladium on charcoal in 250 mL of tetrahydrofuran was shaken in a Parr apparatus under an atmosphere hydrogen. After 2 hours, the reaction was stopped and 10 g of potassium acetate and 50 mL of methanol added. The reaction was recharged with hydrogen and shaken for 18 hours. The solvents were removed under reduced pressure and the residue crystallized from isopropyl alcohol to afford the title compound 2,4-diamino-5-cyanopyridine, mp 201–202° C.

Analysis calculated for $C_6H_6N_4$:
Theory: C, 53.73; H, 4.51; N, 41.78.
Found: C, 53.69; H, 4.18; N, 41.40.

EXAMPLE 15

2,4-Diaminonicotinaldehyde

A suspension of 13.4 g of 2,4-diamino-5-cyanopyridine from Example 14, 2 g of Raney nickel catalyst, 40 mL of 97–100% formic acid, and 80 mL of water were shaken in a Parr apparatus under an atmosphere of nitrogen until the requisite amount of hydrogen was consumed. The solvents were removed under reduced pressure and the residue treated with 17 mL of concentrate HCl. The resulting pink solid was slurried in a small amount of water, filtered, washed with isopropyl alcohol, followed by diethylether, and dried. Crystallization from ethanol afforded 6.5 g of the title compound 2,4-diaminonicotinaldehyde.

Analysis calculated for $C_6H_8N_3ClO$:
Theory: C, 41.52; H, 4.65; N, 24.21.
Found: C, 41.47; H, 4.63; N, 24.05.

EXAMPLE 16

3-o-Tolyl-[1, 6]naphthyridine-2,7-diamine

To a solution of 0.55 g of sodium dissolved in 50 mL of 2-ethoxyethanol was added 2.3 g of 2-methylphenylacetonitrile and 3.0 g of 2,4-diaminonicotinaldehyde from Example 15. The reaction mixture was heated under reflux for 6 hours. The insoluble salts were removed by filtration and washed with 2-ethoxyethanol. The filtrate was treated with charcoal, filtered, and evaporated to dryness. The residue was purified by chromatography over florosil, eluting with a gradient of 0–8% methanol in chloroform to afford 0.7 g of the title compound 3-o-tolyl-[1,6]naphthyridine-2,7-diamine, mp 200–201.5° C. dec.

Analysis calculated for $C_{15}H_{14}N_4$:
Theory: C, 72.03; H, 5.63; N, 22.38.
Found: C, 71.79; H, 5.45; N, 22.18.

EXAMPLE 17

3-(2-Chlorophenyl)-[1,6]naphthyridine-2,7-diamine 3-(2-Chlorophenyl)-[1,6]naphthyridine-2,7-diamine was prepared as described above in Example 16 substituting 2-chlorophenylacetonitrile for 2-methylphenylacetonitrile, mp 175° C. (MS).

EXAMPLE 18

3-(2,6-Dichlorophenyl)-[1,6]-naphthyridine-2,7-diamine 3-(2,6-Dichlorophenyl)-[1,6]-naphthyridine-2,7-diamine was prepared as described above in Example 16 substituting 2,6-dichlorophenylacetonitrile for 2-methylphenylacetonitrile, mp 235–237° C. dec.

Analysis calculated for $C_{14}H_{10}N_4Cl_2$:
Theory: C, 55.10; H, 3.30; N, 18.36; Cl, 23.24.
Found: C, 54.87; H, 3.21; N, 18.45; Cl, 23.04.

EXAMPLE 19

$N^2,N^7$-Dimethyl-6-phenyl-pyrido[2,3-d]pyrimidine-2,7-diamine

A mixture of 45 g of the disulfamate salt of 6-phenyl-pyrido[2,3-d]pyrimidine-2,7-diamine (U.S. Pat. No. 3,534,039) and 500 g of methylamine were heated at 205–210° C. in a bomb for 10 hours. The bomb was washed with methanol and combined with the reaction mixture. The mixture was heated to a boil, filtered, and diluted with 200 mL of water. The filtrate was removed in vacuo and the residue slurried in ice-water. The insoluble material was filtered and washed with cold water. The solid was dissolved in chloroform, filtered to remove impurities, and washed several times with water. The organic layer was dried (potassium carbonate) and evaporated. The product was crystallized from isopropyl alcohol to afford 15 g of the title compound $N^2,N^7$-dimethyl-6-phenyl-pyrido-[2,3-d]pyrimidine-2,7-diamine, mp 204–205° C.

Analysis calculated for $C_{15}H_{15}N_5$:
Theory: C, 67.90; H, 5.70; N, 26.90.
Found: C, 67.89; H, 5.62; N, 26.66.

EXAMPLE 20

7-Amino-6-(2,6-dichlorophenyl)-2-(3-diethylamino-propylamino)-pyrido[2,3-d]pyrimidine A mixture of 2,7-diamino-6-(2,6-dichlorophenyl)-pyrido[2,3-d]pyrimidine (3.0 g) from Example 1, sulfamic acid (2 g) and 3-(diethylamino)propylamine (30 mL) was heated to reflux with stirring for 18 hours. The reaction mixture was allowed to cool to room temperature and poured into ice-water (500 mL). The insoluble product was filtered, washed with water, slurried in warm diisopropyl ether, and filtered to give a white solid. Crystallization from ethyl acetate afforded 1.5 g of 7-amino-6-(2,6-dichlorophenyl-2-(3-diethylamino-propylamino)-pyrido[2,3-d]pyrimidine, mp 220–230° C.

EXAMPLE 21

1-tert-Butyl-3-[6-(2,6-dichlorophenyl)-2-(3-diethyl-amino-propylamino)-pyrido[2,3-d]pyrimidin-7-yl]-urea To a solution of 7-amino-6-(2,6-dichlorophenyl)-2-(3-diethylamino-propylamino)-pyrido[2,3-d]pyrimidine (0.48 g) from Example 20 in DMF (5 mL) was added 60% sodium hydride suspension (46 mg), and the mixture was stirred for 1 hour at room temperature. To the reaction mixture was added t-butyl isocyanate (0.113 g), and the mixture was stirred for 18 hours. The reaction mixture was diluted with water and the insoluble material was collected by filtration. The solid was suspended in water (20 mL) and acidified with 1.0N HCl to form a solution. Activated charcoal was added to the solution, and the suspension filtered through celite, washing with water. The filtrate was made basic with 1.0 N NaOH, and the insoluble product was collected by filtration and washed with water. A 180-mg sample of the product was further purified by reverse phase preparative HPLC on a C18 reverse phase column, eluting with a solvent gradient starting from 86% of 0.1% trifluoroacetic acid in water/14% acetonitrile to 14% of 0.1% trifluoroacetic acid in water/86% acetonitrile over a 22-minute time period to afford 165 mg of 1-tert-butyl-3-[6-(2,6-dichlorophenyl)-2-(3-diethylamino-propylamino)-pyrido[2,3-d]pyrimidin-7-yl]-urea, mp dec >80° C.

Analysis calculated for $C_{25}H_{33}N_7O_1Cl_2.0.22$ $CF_3CO_2H$:
C, 56.21; H, 6.16; N, 18.04.
Found: C, 56.13; H, 6.02; N, 18.14.

EXAMPLE 22

1-[2-Amino-6-(2,6-dichlorophenyl)-pyrido[2,3-d]-pyrimidin-7-yl]-3-ethylurea 2,7-Diamino-6-(2,6-dichlorophenyl)-pyrido[2,3-d]-pyrimidine was reacted with ethyl isocyanate according to the general procedure of Example 2. The crude product was purified by radial chromatography eluting with a gradient of 70% ethyl acetate/30% chloroform to 100% chloroform to give the title compound, 1-[2-amino-6-(2,6-dichlorophenyl)-pyrido[2,3-d]pyrimidin-7-yl]-3-ethylurea, mp 185–187° C.

Analysis calculated for $C_{16}H_{14}N_6O_1Cl_2.0.15$ EtOAc:
C, 51.07; H, 3.92; N, 21.52.
Found: C, 50.74; H, 3.75; N, 21.50.

EXAMPLE 23

1-[2-Amino-6-(2,6-dichlorophenyl)-pyrido[2,3-d]-pyrimidin-7-yl]-3-(3-morpholin-4-yl-propyl)-thiourea 2,7-Diamino-6-(2,6-dimethylphenyl)-pyrido[2,3-d]-pyrimidine was reacted with 3-morpholinopropyl isothiocyanate according to the general procedure of Example 21. The crude product was purified by radial chromatography eluting with a gradient of 2–8% methanol in methylene chloride to give 1-[2-amino-6-(2,6-dichlorophenyl)-pyrido[2,3-d] pyrimidin-7-yl]-3-(3-morpholin-4-yl-propyl)-thiourea, mp 178–181° C. dec;

Analysis calculated for $C_{21}H_{23}N_7O_1Cl_2$:
C, 51.22; H, 4.71; N, 19.91.
Found: C, 50.95; H, 4.63; N, 19.74.

EXAMPLE 24

2-[2-Amino-6-(2,6-dichlorophenyl)-pyrido[2,3-d]-pyrimidin-7-yl]-amino-4,5-dihydro-oxazole To a suspension of 2,7-diamino-6-(2,6-dichlorophenyl)-pyrido[2,3-d]pyrimidine (5.0 g) from Example 1 in DMF (50 mL) was added 0.65 g of NaH (60%) in portions. The mixture was stirred for 1 hour at ambient temperature, then 2-chloroethyl isocyanate (1.72 g) was added, and the mixture was stirred for an additional 18 hours at ambient temperature. The reaction mixture was diluted with 100 mL of water and filtered to provide an insoluble crude product. The crude product was purified by flash chromatography eluting with a gradient of 2–3% methanol in methylene chloride to afford 1.0 g of a white solid. The solid was further purified by recrystallization from chloroform-ethyl acetate to give the title compound 2-[2-amino-6-(2,6-dichlorophenyl)-pyrido[2,3-d]-pyrimidine-7-yl]amino-4,5-dihydro-oxazole. Further analysis of the reaction mixture also showed the presence of 1-[2-amino-6-(2,6-dichlorophenyl)-pyrido[2,3-d]pyrimidin-7-yl]-imidazolidin-2-one, MS(FAB).

Analysis calculated for $C_{16}H_{13}N_6O_1Cl_2.0.12$ $CHCl_3.0.04$:
C, 51.22; H, 4.71; N, 19.91.
Found: C, 50.95; H, 4.63; N, 19.74.

EXAMPLE 25

1-Butyl-3-[7-(3-butyl-ureido)-6-(2,6-dichlorophenyl)-pyrido[2,3-d]pyrimidin-2-yl]-urea A mixture of 0.5 g 2,7-Diamino-6-(2,6-dichlorophenyl)-pyrido[2,3-d]pyrimidine from Example 1 and 15 mL of n-butyl isocyanate is refluxed for 2 hours. The reaction mixture is allowed to cool to room temperature and the insoluble material filtered. The solid is recrystallized several times from ethanol to give the title compound; mp 200–202° C.

Analysis calculated for $C_{23}H_{27}C_{12}N_7O_2.0.35$ $H_2O$:
C, 54.09; H, 5.47; N, 19.20.
Found: C, 54.09; H, 5.27; N, 19.14.

EXAMPLE 26

1-[2-Amino-6-(2,6-dichlorophenyl)-pyrido[2,3-d]-pyrimidin-7-yl]-3-propyl-urea

The title compound was prepared as described in Example 2 by reacting 1.0 g of 2,7-diamino-6-(2,6-dichlorophenyl)-pyrido[2,3-d]pyrimidine from Example 1 and 0.339 g of n-propyl isocyanate. The product was purified by radial chromatography eluting with a gradient of 10–100% ethyl acetate/Hexane. MS(CI).

Analysis calculated for $C_{17}H_{16}Cl_2N_6O_1.0.43$ $H_2O$:
C, 51.17; H, 4.26; N, 21.06.
Found: C, 51.15; H, 3.90; N, 20.80.

EXAMPLE 27

7-Amino-6-(2,6-dichlorophenyl)-2-(3-dimethylamino-propylamino)-pyrido[2,3-d] pyrimidine The title compound was prepared as in Example 20 by reacting 3.0 g of 2,7-diamino-6-(2,6-dichlorophenyl)-pyrido

[2,3-d]pyrimidine from Example 1 and 60 mL of 3-(dimethylamino)propylamine to give the title compound.

EXAMPLE 28

1-tert-Butyl-3-[6-(2,6-dichlorophenyl)-2-(3-dimethylamino-propylamino)-pyrido[2,3-d]pyrimidin-7-yl]-urea Following the procedure of Example 21, 1.62 g of 7-amino-6-(2,6-dichlorophenyl)-2-(3-dimethylamino-propylamino)-pyrido[2,3-d]pyrimidine from Example 27 was reacted with 0.48 g of t-butyl isocyanate to give the title compound; mp gradually dec above 130° C.

Analysis calculated for $C_{23}H_{29}C_{12}N_7O_1.1.45\ H_2O$:
C, 53.48; H, 6.22; N, 18.98.
Found: C, 53.50; H, 5.84; N, 18.73.

EXAMPLE 29

7-Amino-6-(2,6-dichlorophenyl)-2-(3-dimethylamino-2,2-dimethyl-propylamino)-pyrido[2,3-d]pyrimidine The title compound was prepared as described above in Example 20 by reacting 2.0 g of 2,7-diamino-6-(2,6-dichlorophenyl)-pyrido[2,3-d]pyrimidine from Example 1 and 15 mL of N,N,2,2-tetramethyl-1,3-propanediamine.

EXAMPLE 30

1-tert-Butyl-3-[6-(2,6-dichlorophenyl)-2-(3-dimethylamino-2,2-dimethyl-propylamino)-pyrido[2,3-d]pyrimidin-7-yl]-urea Following the procedure of Example 21, 1.0 g of 7-amino-6-(2,6-dichlorophenyl)-2-(3-dimethylamino-2,2-dimethyl-propylamino)-pyrido[2,3-d]pyrimidine from Example 29 was reacted with 0.26 g of t-butyl isocyanate to give the title compound; mp 161–170° C.

Analysis calculated for $C_{25}H_{33}Cl_2N_7O_1.0.74\ H_2O$:
C, 56.46; H, 6.54; N, 18.44.
Found: C, 56.47; H, 6.24; N, 18.41.

EXAMPLE 31

7-Amino-6-(2,6-dichlorophenyl)-2-(3-(2-picoline)-propylamino)-pyrido[2,3-d]pyrimidine The title compound was prepared as described above in Example 20 starting from 2.0 g of 2,7-diamino-6-(2,6-dichlorophenyl)-pyrido[2,3-d]pyrimidine from Example 1 and 15 mL of 1-(3-aminopropyl)-2-picoline to give the title compound.

EXAMPLE 32

1-tert-Butyl-3-{6-(2,6-dichlorophenyl)-2-[3-(2-methyl-piperidin-1-yl)-propylamino]-pyrido[2,3-d]pyrimidin-7-yl}-urea According to Example 21, 1.54 g of 7-amino-6-(2,6-dichlorophenyl)-2-(3-(2-picoline)-propylamino)-pyrido[2,3-d]pyrimidine from Example 31 was reacted with 0.377 g of t-butyl isocyanate to give the title compound.

Analysis calculated for $C_{27}H_{35}Cl_2N_7O_1$:
C, 59.56; H, 6.48; N, 18.01.
Found: C, 59.71; H, 6.53; N, 17.62.

EXAMPLE 33

7-Amino-6-(2,6-dichlorophenyl)-2-(4-(4-methyl-piperazin-1-yl)-butylamino)-pyrido[2,3-d]pyrimidine Following the procedure of Example 20, 2.0 g of 2,7-diamino-6-(2,6-dichlorophenyl)-pyrido[2,3-d]-pyrimidine from Example 1 was reacted with 15 mL of 1-(4-aminobutyl)-4-methyl-piperazine to give the title compound.

EXAMPLE 34

1-tert-Butyl-3-{6-(2,6-dichlorophenyl)-2-[4-(4-methyl-piperazin-1-yl)-butylamino]-pyrido[2,3-d]pyrimidin-7-yl}-urea According to Example 21, 1.07 g of 7-amino-6-(2,6-dichlorophenyl)-2-(4-(4-methylpiperazine)-butylamino)-pyrido[2,3-d]pyrimidine from above in Example 33 was reacted with 0.253 g of t-butyl isocyanate to give the title compound.

ESMS m/z (relative intensity) 559 (M$^+$, 100)
Analysis calculated for $C_{27}H_{36}Cl_2N_8O_1.0.6\ H_2O$:
C, 56.86; H, 6.57; N, 19.65.
Found: C, 56.87; H, 6.31; N, 19.57.

EXAMPLE 35

6-(2,6-Dichlorophenyl)-$N^7$(5,6-dihydro-4H-[1,3] oxazin-2-yl)-$N^2$-[3-(4-methyl-piperazin-1-yl)-propyl]-pyrido[2,3-d]pyrimidine-2,7-diamine To a solution of 1.0 g of 6-(2,6-dichlorophenyl)-$N^2$-[3-(4-methyl-piperazin-1-yl)-propyl[2,3-d]-pyrimidine-2,7-diamine from Example 36 in 10 mL of dimethylformamide was added sodium hydride (60% in oil, 0.094 g), and the mixture was stirred for 1 hour at ambient temperature. To the reaction mixture was added 0.268 g of 3-chloropropyl isocyanate, and the mixture was stirred at ambient temperature for 18 hours. The reaction mixture was diluted with water and extracted twice with ethyl acetate. The combined organic layers were dried (MgSO$_4$), filtered, and evaporated. The crude product was purified twice by radial chromatography eluting with ethyl acetate/methanol/triethylamine (89:10:1 v/v/v) to give the title compound.

ESMS m/z (relative intensity) 529.4 (M$^+$, 100)

EXAMPLE 36

$N^2$-[3-(4-methyl-piperazin-1-yl)-propyl]-6-(2,6-dichlorophenyl)-pyrido[2,3-d]pyrimidine-2,7-diamine A mixture of 2,7-diamino-6-(2,6-dichlorophenyl)-pyrido [2,3-d]pyrimidine (3.0 g) from Example 1, sulfamic acid (1.9 g), and 1-(3-aminopropyl)-4-methylpiperazine (15 mL) was heated to approximately 150° C. for 24 hours After cooling, the residue was dissolved in water. The aqueous solution was made alkaline with a solution of saturated sodium bicarbonate and extracted with dichloromethane several times. The dichloromethane layers were combined, dried over magnesium sulfate, and concentrated in vacuo. The residue was recrystallized from ethyl acetate to give 2.0 g of 6-(2,6-dichlorophenyl)-$N^2$-[3-(4-methyl-piperazin-1-yl)-propyl]-pyrido[2,3-d]pyrimidine-2,7-diamine, CIMS (1% NH$_3$ in CH$_4$): 474=M$^+$+C$_2$H$_5$, 446=M$^+$+H (Base); mp 208–211° C.

Analysis calculated for $C_{21}H_{25}N_7Cl_2.0.25\ H_2O$.
Theory: C, 55.94; H, 5.70; N, 21.75.
Found: C, 55.85; H, 5.55; N, 21.65.

EXAMPLE 37

1-Cyclohexyl-3-{6-(2,6-dichlorophenyl)-2-[3-(4-methyl-piperazin-1-yl)-propylamino]-pyrido[2,3-d]pyrimidin-7-yl}-urea To a solution of 6-(2,6-dichlorophenyl)-$N^2$-[3-(4-methyl-piperazin-1-yl)-propyl]-pyrido[2,3-d]pyrimidine-2,7- diamine (1.0 g) from Example 36 in DMF (15 mL) was added one equivalent of 60% sodium hydride suspension (0.90 g). After stirring for approximately 1 hour at room temperature, one equivalent of cyclohexyl isocyanate (0.19 g) was added, and the reaction was monitored by thin layer chromatography. After approximately 24 hours, the solvent was removed in vacuo. The residue was dissolved in ethyl acetate, and this solution was washed several times, first with water and then a saturated solution of sodium chloride. The ethyl acetate layer was dried with magnesium sulfate and concentrated in vacuo. Chromatography of the residue on silica gel using ethyl acetate:ethanol:triethylamine (9:2:1 v/v/v) afforded 0.75 g of 1-cyclohexyl-3-{6-(2,6-dichlorophenyl)-2-[3-(4-methyl-piperazin-1-yl)-propylamino]pyrido[2,3-d]pyrimidin}-7-yl}-urea, ESMS (20/80 MeOH/CH$_3$CN+0.1% AcOH) M$^+$+H=571; mp 101–106.5° C.

Analysis calculated for C$_{28}$H$_{36}$N$_8$Cl$_2$O.0.50 H$_2$O:

Theory: C, 57.93; H, 6.42; N, 19.30; Cl, 12.21; H$_2$O, 1.55.

Found: C, 58.06; H, 6.32; N, 18.91; Cl, 12.11; H$_2$O, 1.68.

EXAMPLE 38

1-{6-(2,6-Dichlorophenyl)-2-[3-(4-methyl-piperazin-1-yl-propylamino]-pyrido[2,3-d]pyrimidin-7-yl}-3-isopropyl-urea 6-(2, 6-Dichlorophenyl)-N$^2$-[3-(4-methyl-piperazin-1-yl)-propyl]-pyrido[2,3-d]pyrimidine-2,7-diamine (1.09 g) from Example 36 was reacted with 0.19 g of isopropyl isocyanate for 8 hours according to the general procedure of Example 37 to give 0.291 g of 1-{6-(2,6-dichlorophenyl)-2-[3-(4-methyl-piperazin-1 -yl-propylamino]-pyrido[2,3-d] pyrimidin-7-yl}-3-isopropyl-urea, MS (ES+20/80 MeOH/CH$_3$CN+0.1% ACOH): M$^+$+H=531; mp 94–98° C.

Analysis calculated for C$_{25}$H$_{32}$N$_8$Cl$_2$O.0.75 H$_2$O/0.10 EtOAc:

Theory: C, 55.09; H, 6.24; N, 20.23; Cl, 12.80; H$_2$O, 2.44.

Found: C, 55.14; H, 6.19; N, 20.03; Cl, 13.17; H$_2$O, 2.14.

EXAMPLE 39

1-Benzyl-3-{6-(2,6-dichlorophenyl)-2-[3-(4-methyl-piperazin-1-yl)-propylamino]-pyrido[2,3-d]pyrimidin-7-yl}-urea 6-(2,6-Dichlorophenyl)-N$^2$-[3-(4-methyl-piperazin-1-yl)-propyl]-pyrido[2,3-d]pyrimidine-2,7-diamine (1.08 g) from Example 36 was reacted with 0.298 g of benzyl isocyanate according to the general procedure of Example 37 to give 0.822 g of 1-benzyl-3-{6-(2,6-dichlorophenyl)-2-[3-(4-methyl-piperazin-1-yl)-propylamino]-pyrido[2,3-d] pyrimidin-7-yl}-urea, ESMS (20/80 MeOH/CH$_3$CN+0.1% AcOH): M$^+$+H=579; mp 144–148.5° C.

Analysis calculated for C$_{29}$H$_{32}$N$_8$Cl$_2$O.0.10 H$_2$O.0.10 Et$_2$O:

Theory: C, 59.98; H, 5.68; N, 19.03; Cl, 12.04; H$_2$O, 0.31.

Found: C, 59.60; H, 5.63; N, 18.87; Cl, 12.25; H$_2$O, 0.49.

EXAMPLE 40

1-Allyl-3-{6-(2,6-dichlorophenyl)-2-[3-(4-methyl-piperazin-1-yl)-propylamino]-pyrido[2,3-d]pyrimidin-7-yl}-urea 6-(2,6-Dichlorophenyl)-N$^2$-[3-(4-methyl-piperazin-1-yl)-propyl]-pyrido[2,3-d]pyrimidine-2,7-diamine (1.0 g) from Example 36 was reacted with 0.186 g of allyl isocyanate according to the general procedure of Example 37. The product was purified by chromatography and crystallized from ethyl acetate to give 0.31 g of 1-allyl-3-{6-(2,6-dichlorophenyl)-2-[3-(4-methyl-piperazin-1-yl)-propylamino]-pyrido[2,3-d]pyrimidin-7-yl}-urea, ESMS (20/80 MeOH/CH$_3$CN+0.1% AcOH): M$^+$+H=529 (Base), 472, 446; mp 104–108° C.

Analysis calculated for C$_{25}$H$_{30}$N$_8$Cl$_2$O.1.00 H$_2$O:

Theory: C, 54.85; H, 5.89; N, 20.47; Cl, 12.95; H$_2$O, 3.29.

Found: C, 55.08; H, 5.68; N, 20.33; Cl, 12.65; H$_2$O, 3.60.

EXAMPLE 41

1-{6-(2,6-Dichlorophenyl)-2-[3-(4-methyl-piperazin-1-yl)-propylamino]-pyrido[2,3-d]pyrimidin-7-yl}-3-(4-methoxy-phenyl)-urea 6-(2, 6-Dichlorophenyl)-N$^2$-[3-(4-methyl-piperazin-1-yl)-propyl]-pyrido[2,3-d]pyrimidine-2,7-diamine (1.0 g) from Example 36 was reacted with 4-methoxyphenyl isocyanate (0.334 g) according to the general procedure of Example 37 to give 1.16 g of 1-{6-(2,6-dichlorophenyl)-2-[3-(4-methyl-piperazin-1-yl)-propylamino]-pyrido[2,3-d]pyrimidin-7-yl}-3-(4-methoxy-phenyl)-urea, ESMS (20/80 MeOH/CH$_3$CM+0.1% AcOH): M$^+$+H=595; mp 93.5–100.5° C.

Analysis calculated for C$_{29}$H$_{32}$N$_8$Cl$_2$O$_2$.0.40 H$_2$O.0.10 EtOAc:

Theory: C, 57.74; H, 5.54; N, 18.32; Cl, 11.59; H$_2$O, 1.18.

Found: C, 58.04; H, 5.51; N, 18.15; Cl, 11.25; H$_2$O, 1.38.

EXAMPLE 42

1-{6-(2,6-Dichlorophenyl)-2-[3-(4-methyl-piperazin-1-yl)-propylamino]-pyrido[2,3-d]pyrimidin-7-yl}-3-(3-methoxy-phenyl)-urea 6-(2,6-Dichlorophenyl)-N$^2$-[3-(4-methyl-piperazin-1-yl)-propyl]-pyrido[2, 3-d]pyrimidine-2,7-diamine (1.0 g) from Example 36 was reacted with 0.334 g of 3-methoxyphenyl isocyanate according to the general procedure of Example 37 to give 0.920 g of 1-{6-(2,6-dichlorophenyl)-2-[3-(4-methyl-piperazin-1-yl)-propylamino]-pyrido[2,3-d]pyrimidin-7-yl}-3-(3-methoxy-phenyl)-urea, ESMS (20/80 MeOH/CH$_3$CN+0.1% AcOH): M$^+$+H=595; mp 87.5–92.5° C.

Analysis calculated for C$_{29}$H$_{32}$N$_8$Cl$_2$O$_2$.0.50 H$_2$O:

Theory: C, 57.62; H, 5.50; N, 18.54; Cl, 11.73; H$_2$O, 1.49.

Found: C, 57.93; H, 5.62; N, 18.47; Cl, 11.66; H$_2$O, 1.10.

EXAMPLE 43

1-{6-(2,6-Dichlorophenyl)-2-[3-(4-methyl-piperazin-1-yl)-propylamino]-pyrido[2,3-d]pyrimidin-7-yl}-3-(2-methoxy-phenyl)-urea 6-(2,6-Dichlorophenyl)-N$^2$-[3-(4-methyl-piperazin-1-yl)-propyl]-pyrido[2,3-d]pyrimidine-2,7-diamine (1.0 g) from Example 36 was reacted with 0.334 of 2-methoxyphenyl isocyanate according to the general procedure of Example 37 to give 0.9232 g of 1-{6-(2,6-dichlorophenyl)-2-[3-(4-methyl-piperazin-1-yl)-propylamino]-pyrido[2,3-d] pyrimidin-7-yl}-3-(2-methoxy-phenyl)-urea, ESMS (20/80 MeOH/CH$_3$CN+0.1% AcOH): M$^+$+H=595; mp 152.5–154° C.

Analysis calculated for $C_{29}H_{32}N_8Cl_2O_2$:
Theory: C, 58.49; H, 5.42; N, 18.82; Cl, 11.91.
Found: C, 58.42; H, 5.56; N, 18.59; Cl, 11.82.

EXAMPLE 44

1-(4-Bromo-phenyl)-3-{6-(2,6-dichlorophenyl)-2-[3-(4-methyl-piperazin-1-yl)-propylamino]-pyrido[2,3-d]-pyrimidin-7-yl}-urea 6-(2,6-Dichlorophenyl)-$N^2$-[3-(4-methyl-piperazin-1-yl)-propyl]-pyrido[2,3-d]pyrimidine-2,7-diamine (1.0 g) from Example 36 was reacted with 0.44 g of 4-bromophenyl isocyanate according to the general procedure of Example 37 to give 0.97 g of 1-(4-Bromo-phenyl)-3-{6-(2,6-dichlorophenyl)-2-[3-(4-methylpiperazin-1-yl)-propylamino]-pyrido[2,3-d]pyrimidin-7-yl}-urea, ESMS (20/80 MeOH/$CH_3CN$+0.1% AcOH+DMSO): $M^+$+H=645; mp 171–175° C.

Analysis calculated for $C_{28}H_{29}N_8Cl_2OBr$:
Theory: C, 52.19; H, 4.54; N, 17.39; Cl, 11.00; Br, 12.40.
Found: C, 51.93; H, 4.71; N, 17.14; Cl, 10.81; Br, 12.18.

EXAMPLE 45

1-(4-Chloro-phenyl)-3-{6-(2,6-dichlorophenyl)-2-[3-(4-methyl-piperazin-1-yl)-propylamino]-pyrido[2,3-d]-pyrimidin-7-yl}-urea 6-(2,6-Dichlorophenyl)-$N^2$-[3-(4-methyl-piperazin-1-yl)-propyl]-pyrido[2,3-d]pyrimidine-2,7-diamine (1.0 g) from Example 36 was reacted with 0.344 g of 4-chlorophenyl isocyanate according to the general procedure of Example 37 to give 0.8424 g of 1-(4-Chloro-phenyl)-3-{6-(2,6-dichlorophenyl)-2-[3-(4-methyl-piperazin-1-yl)-propylamino]-pyrido[2,3-d]pyrimidin-7-yl}-urea, ESMS (20/80 MeOH/$CH_3CN$+0.1% AcOH+DMSO): $M^+$+H=601; mp 175.5–181° C.

Analysis calculated for $C_{28}H_{29}N_8Cl_3O$:
Theory: C, 56.06; H, 4.87; N, 18.68; Cl, 17.73.
Found: C, 56.11; H, 5.14; N, 18.47; Cl, 17.67.

EXAMPLE 46

1-{6-(2,6-Dichlorophenyl)-2-[3-(4-methyl-piperazin-1-yl)-propylamino]-pyrido[2,3-d]pyrimidin-7-yl}-3-p-tolyl-urea 6-(2,6-Dichlorophenyl)-$N^2$-[3-(4-methyl-piperazin-1-yl)-propyl]-pyrido[2,3-d]pyrimidine-2,7-diamine from Example 36 was reacted with 0.29 g of 4-tolyl isocyanate according to the general procedure of Example 37 to give 0.9492 g of the title compound. ESMS (20/80 MeOH/$CH_3CN$+0.1% ACOH): $M^+$+H=579;

Analysis calculated for $C_{29}H_{32}N_8Cl_2O$·0.30 $H_2O$+0.20 EtOAc:
Theory: C, 59.40; H, 5.72; N, 18.60; Cl, 11.77; $H_2O$, 0.90.
Found: C, 59.69; H, 5.61; N, 18.41; Cl, 11.50; $H_2O$, 1.31.

EXAMPLE 47

1-{6-(2,6-Dichlorophenyl)-2-[3-(4-methyl-piperazin-1-yl)-propylamino]-pyrido[2,3-d]pyrimidin-7-yl}-3-octyl-urea 6-(2, 6-Dichlorophenyl)-$N^2$-[3-(4-methyl-piperazin-1-yl)-propyl]-pyrido[2,3-d]pyrimidine-2,7-diamine (1.0 g) from Example 36 was reacted with 0.348 g of octyl isocyanate according to the general procedure of Example 21. Chromatography, eluting first with ethyl acetate:methyl alcohol:triethylamine (90:10:1) then switching to ethyl acetate:ethanol:triethylamine (9:2:1) gave 1.011 g of the title compound 1-{6-(2,6-dichlorophenyl)-2-[3-(4-methyl-piperazin-1-yl)-propylamino]-pyrido[2,3-d]-pyrimidin-7-yl}-3-octyl-urea, ESMS (20/80 MeOH/$CH_3CN$+0.1% AcOH): $M^+$+H=601; mp 54.5–57.5° C.

Analysis calculated for $C_{30}H_{42}N_8Cl_2O$·0.75 $H_2O$:
Theory: C, 58.58; H, 7.13; N, 18.22; Cl, 11.53; $H_2O$, 2.20.
Found: C, 58.51; H, 7.13; N, 18.13; Cl, 11.55; $H_2O$, 2.32.

EXAMPLE 48

1-{6-(2,6-Dichlorophenyl)-2-[3-(4-methyl-piperazin-1-yl)-propylamino]-pyrido[2,3-d]pyrimidin-7-yl}-3-(4-trifluoromethyl-phenyl)-urea 6-(2, 6-Dichlorophenyl)-$N^2$-[3-(4-methyl-piperazin-1-yl)-propyl]-pyrido[2,3-d]pyrimidine-2,7-diamine from Example 36 was reacted with trifluoro-p-tolyl isocyanate according to the general procedure of Example 37. Chromatography, eluting first with ethyl acetate:methyl alcohol:triethylamine (90:10:1) then switching to ethyl acetate:ethanol:triethylamine (9:2:1) gave 0.8650 g of the title compound 1-{6-(2,6-dichlorophenyl)-2-[3-(4-methyl-piperazin-1-yl)-propylamino]-pyrido[2,3-d]pyrimidin-7-yl}-3-(4-trifluoromethyl-phenyl)-urea, ESMS (20/80 MeOH/$CH_3CN$ +0.1% AcOH): $M^+$+H=633; mp 145.5–151° C.

Analysis calculated for $C_{29}H_{29}N_8Cl_2F_3O$·0.50 $H_2O$:
Theory: C, 54.21; H, 4.71; N, 17.44; Cl, 11.04; F, 8.87; $H_2O$, 1.40.
Found: C, 54.39; H, 4.59; N, 17.28; Cl, 11.10; F, 9.17; $H_2O$, 1.61.

EXAMPLE 49

1-{6-(2,6-Dichlorophenyl)-2-[3-(4-methyl-piperazin-1-yl)-propylamino]-pyrido[2,3-d]pyrimidin-7-yl}-3-ethyl-urea 6-(2, 6-Dichlorophenyl)-$N^2$-[3-(4-methyl-piperazin-1-yl)-propyl]-pyrido[2,3-d]pyrimidine-2,7-diamine (1.0 g) from Example 36 was reacted with 0.159 g of ethyl isocyanate according to the general procedure of Example 37 to give 0.86 g of 1-{6-(2,6-dichlorophenyl)-2-[3-(4-methyl-piperazin-1-yl)-propylamino]-pyrido-[2,3-d]pyrimidin-7-yl}-3-ethyl-urea, MS (ES+20/80 MeOH/$CH_3CN$+0.1% ACOH): $M^+$+H=517; mp 82–90° C.

Analysis calculated for $C_{24}H_{30}N_8Cl_2O$·1.00 $H_2O$:
Theory: C, 53.83; H, 6.02; N, 20.93; Cl, 13.24; $H_2O$, 3.26.
Found: C, 53.94; H, 6.07; N, 20.53; Cl, 13.14; $H_2O$, 3.28.

EXAMPLE 50

1-{6-(2,6-Dichlorophenyl)-2-[3-(4-methyl-piperazin-1-yl)-propylamino]-pyrido[2,3-d]pyrimidin-7-yl}-3-naphthalen-1-yl-urea 6-(2,6-Dichlorophenyl)-$N^2$-[3-(4-methyl-piperazin-1-yl)-propyl]-pyrido[2,3-d]pyrimidine-2,7-diamine (1.0 g) from Example 36 was reacted with 0.378 g of 1-naphthyl isocyanate according to the general procedure of Example 37. Chromatography, eluting first with ethyl acetate:methyl alcohol:triethylamine (90:10:1) then switching to ethyl acetate:ethanol:triethylamine (9:2:1) gave 0.97 g of the title compound 1-{6-(2,6-dichlorophenyl)-2-[3-(4-methyl-piperazin-1-yl)-propylamino]-pyrido[2,3-d]-pyrimidin-7-yl}-3-naphthalen-1-yl-urea, ESMS (20/80 MeOH/CH$_3$CN+ 0.1% AcOH): M$^+$+H=615 (Base), 446; mp 186.5–189° C.

Analysis calculated for C$_{32}$H$_{32}$N$_8$Cl$_2$O.0.10 H$_2$O:

Theory: C, 62.26; H, 5.26; N, 18.15; Cl, 11.49; H$_2$O, 0.29.

Found: C, 62.25; H, 5.26; N, 18.38; Cl, 11.39; H$_2$O, 0.51.

EXAMPLE 51

1-{6-(2,6-Dichlorophenyl)-2-[3-(4-methyl-piperazin-1-yl)-propylamino]-pyrido[2,3-d]pyrimidin-7-yl}-3-phenyl-urea 6-(2,6-Dichlorophenyl)-N$^2$-[3-(4-methyl-piperazin-1-yl)-propyl]-pyrido[2,3-d]pyrimidine-2,7-diamine (13.0 g) from Example 36 in DMF (160 mL) was reacted with 60% sodium hydride suspension (1.16 g) and phenyl isocyanate (3.47 g) according to the general procedure of Example 37. Recrystallization of the chromatographed product from ethyl acetate gave 10.78 g of the title compound 1-{6-(2,6-dichlorophenyl)-2-[3-(4-methyl-piperazin-1-yl)-propylamino]-pyrido[2,3-d]-pyrimidin-7-yl}-3-phenyl-urea, ESMS (20/80 MeOH/CH$_3$CN+0.1% AcOH): M$^+$+H= 565;

Analysis calculated for C$_{28}$H$_{30}$N$_8$Cl$_2$O.0.30 H$_2$O.0.20 EtOAc:

Theory: C, 58.78; H, 5.51; N, 19.04; Cl, 12.05; H$_2$O, 0.92.

Found: C, 58.72; H, 5.55; N, 18.84; Cl, 11.98; H$_2$O, 1.01.

EXAMPLE 52

1-tert-Butyl-3-{6-(2,6-dichlorophenyl)-2-[3-(4-methyl-piperazin-1-yl)-propylamino]-pyrido[2,3-d]pyrimidin-7-yl}-urea 6-(2, 6-Dichlorophenyl)-N$^2$-[3-(4-methyl-piperazin-1-yl)-propyl]-pyrido[2,3-d]pyrimidine-2,7-diamine (1.0 g) from Example 36 was reacted with 0.22 g of tert-butyl isocyanate for 1.5 hours according to the general procedure of Example 21 to give 0.85 g of the title compound 1-tert-Butyl-3-{6-(2,6-dichlorophenyl)-2-[3-(4-methyl-piperazin-1-yl)-propylamino]-pyrido[2,3-d]pyrimidin-7-yl}-urea, CIMS (1% NH$_3$ in CH$_4$): 545=M$^+$+H, 544=M$^+$, 446, 84 (Base); mp dec. 97.5° C. melts 106–109° C.

Analysis calculated for C$_{26}$H$_{344}$N$_8$Cl$_2$O:

Theory: C, 57.25; H, 6.28; N, 20.25.

Found: C, 56.91; H, 6.31; N, 20.30.

EXAMPLE 53

6-(2, 6-Dichlorophenyl)-N$^2$-(4-diethylamino-butyl)-pyrido[2,3-d]pyrimidine-2,7-diamine A mixture of 2,7-diamino-6-(2,6-dichlorophenyl)-pyrido [2,3-d]pyrimidine (40 g) from Example 1, sulfamic acid (25.4 g) and diethylaminobutylamine (205 mL) was heated to approximately 150° C. for 28 hours. The reaction temperature was lowered to 50° C., and excess diethylaminobutylamine was removed in vacuo. After cooling to 25° C., the residue was suspended in water. The aqueous solution was made alkaline with a solution of saturated sodium bicarbonate and extracted with dichloromethane several times. The dichloromethane layers were combined, washed several times, first with a saturated solution of sodium bicarbonate then a saturated solution of sodium chloride, dried over magnesium sulfate and concentrated in vacuo. The residue was washed repeatedly with diethyl ether and then crystallized from ethyl acetate. The recrystallized product was further purified by column chromatography, eluting first with ethyl acetate:methyl alcohol:triethylamine (85:14:1) followed by ethyl acetate:ethyl alcohol:triethylamine (9:2:1) to afford 36.2 g of the title compound 6-(2,6-dichlorophenyl)-N$^2$-(4-diethylamino-butyl)-pyrido[2,3-d] pyrimidine-2,7-diamine, CIMS (1% N$_3$ in CH$_4$): 461=M$^+$+ C$_2$H$_5$, 433=M$^+$+H (Base), 417, 403, 360.

Analysis calculated for C$_{21}$H$_{26}$N$_6$Cl$_2$:

Theory: C, 58.20; H, 6.05; N, 19.39; Cl, 16.36.

Found: C, 58.11; H, 6.21; N, 19.09; Cl, 16.55.

EXAMPLE 54

1-[6-(2,6-Dichlorophenyl)-2-(4-diethylamino-butylamino)-pyrido[2,3-d]pyrimidin-7-yl]-3-phenyl-urea To a solution of 6-(2,6-dichlorophenyl)-N$^2$-(4-diethylamino-butyl)-pyrido[2,3-d]pyrimidine-2,7-diamine (1.0 g) from Example 53 in DMF (15 mL) was added one equivalent of 60% sodium hydride suspension (0.93 g). After stirring for approximately 1 hour at room temperature, one equivalent of phenyl isocyanate (0.275 g) was added, and the reaction was monitored by thin layer chromatography. After approximately 24 hours, the solvent was removed in vacuo. The residue was dissolved in ethyl acetate, and this solution was washed several times, first with water and then a saturated solution of sodium chloride. The ethyl acetate layer was dried with magnesium sulfate and concentrated in vacuo. Chromatography of the residue over silica gel using ethyl acetate:methanol:triethylamine (90:10:1) followed by ethyl acetate:ethanol:triethylamine (9:2:1) gave 0.8461 g of the title compound 1-[6-(2,6-dichlorophenyl)-2-(4-diethylamino-butylamino)-pyrido[2,3-d]pyrimidin-7-yl]-3-phenyl-urea, ESMS (20/80 MeOH/CH$_3$CN+0.1% AcOH) M$^+$+H=552 (Base), 433; mp 81–87.5° C.

Analysis calculated for C$_{28}$H$_{31}$N$_7$Cl$_2$O.0.25 H$_2$O:

Theory: C, 60.38; H, 5.70; N, 17.60; Cl, 12.73; H$_2$O, 0.81.

Found: C, 60.24; H, 5.61; N, 17.42; Cl, 12.61; H$_2$O, 0.54.

EXAMPLE 55

1-[6-(2,6-Dichlorophenyl)-2-(4-diethylamino-butylamino)-pyrido[2,3-d]pyrimidin-7-yl]-3-ethyl-urea 6-(2,6-Dichlorophenyl)-N$^2$-(4-diethylamino-butyl)-pyrido[2,3-d]pyrimidine-2,7-diamine (5.0 g) from Example 53 in DMF (75 mL) was reacted with 60% sodium hydride suspension (0.461 g) and ethyl isocyanate (0.820 g) according to the general procedure of Example 54. Chromatography with ethyl acetate:ethanol:triethylamine (9:2:1) gave 4.26 g of the title compound 1-[6-(2,6-dichlorophenyl)-2-(4-diethylamino-butylamino)-pyrido[2,3-d]pyrimidin-7-yl]-3-ethyl-urea, ESMS (20/80 MeOH/CH$_3$CN+0.1% AcOH): M$^+$+H=504 (Base), 433.

EXAMPLE 56

1-[6-(2,6-Dichlorophenyl)-2-(4-diethylamino-butylamino)-pyrido[2,3-d]pyrimidin-7-yl]-3-ethyl-urea, hydrochloride salt To a solution of 1-[6-(2,6-dichlorophenyl)-2-(4-diethylamino-butylamino)-pyrido[2,3-d]pyrimidin-7-yl]-3-ethyl-urea (3.253 g) from Example 55 in water (250 mL)

was added one equivalent of 1N hydrochloric acid (6.44 mL). The solution was stirred at room temperature until the solid was dissolved, filtered, and frozen. Lyophilization gave 3.63 g the hydrochloric acid salt of 1-[6-(2,6-dichlorophenyl)-2-(4-diethylamino-butylamino)-pyrido[2,3-d]pyrimidin-7-yl]-3-ethyl-urea, ESMS (20/80 MeOH/CH$_3$CN+1% AcOH) M$^+$+H=504; mp dec >50° C.

Analysis calculated for C$_{24}$H$_{31}$N$_7$Cl$_2$O.1.10 HCl.2.20 H$_2$O:

Theory: C, 49.34; H, 6.30; N, 16.78; Cl$_{Total}$, 18.81; Cl$_{Ionic}$, 6.67; H$_2$O, 6.78.

Found: C, 49.61; H, 6.21; N, 16.75; Cl$_{Total}$, 18.70; Cl$_{Ionic}$, 6.68; H$_2$O, 6.88.

EXAMPLE 57

1-Cyclohexyl-3-[6-(2,6-dichlorophenyl)-2-(4-diethylamino-butylamino)-pyrido[2,3-d]pyrimidin-7-yl]-urea 6-(2, 6-Dichlorophenyl)-N$^2$-(4-diethylamino-butyl)-pyrido[2,3-d]pyrimidine-2,7-diamine (1.0 g) from Example 53 in DMF (15 mL) was reacted with 60% sodium hydride suspension (0.092 g) and cyclohexyl isocyanate (0.289 g) according to the general procedure of Example 54 to give 0.927 g of the title compound, ESMS (20/80 MeOH/CH$_3$CN+0.1% AcOH): M$^+$+H=558, 433.

Analysis calculated for C$_{28}$H$_{37}$N$_7$Cl$_2$O.0.10 H$_2$O:

Theory: C, 60.02; H, 6.69; N, 17.50; Cl, 12.65; H$_2$O, 0.32.

Found: C, 59.75; H, 6.69; N, 17.41; Cl, 12.71; H$_2$O, 0.40.

EXAMPLE 58

6-(2,6-Dichlorophenyl)-N$^2$-(3-morpholin-4-yl-propyl)-pyrido[2,3-d]pyrimidine-2,7-diamine A mixture of 2,7-diamino-6-(2,6-dichlorophenyl)-pyrido[2,3-d]pyrimidine (4.00 g) from Example 1, sulfamic acid (2.53 g) and aminopropylmorpholine (30 mL) was reacted as in Example 53. In this instance, the crude residue was washed with hot ethyl acetate followed by diethyl ether to afford 3.95 g of the title compound 6-(2,6-dichlorophenyl)-N$^2$-(3-morpholin-4-yl-propyl)-pyrido[2,3-d]pyrimidine-2,7-diamine, CIMS (1% NH$_3$ in CH$_4$): 461=M$^+$+C$_2$H$_5$, 433=M$^+$+H (Base), 346, 332; mp 224–230.5° C.

Analysis calculated for C$_{20}$H$_{22}$N$_6$Cl$_2$O:

Theory: C, 55.43; H, 5.12; N, 19.39.

Found: C, 55.12; H, 5.12; N, 19.14.

EXAMPLE 59

1-tert-Butyl-3-[6-(2,6-dichlorophenyl)-2-(3-morpholin-4-yl-propylamino)-pyrido[2,3-d]pyrimidin-7-yl]-urea To a solution of 6-(2,6-dichlorophenyl)-N$^2$-(3-morpholin-4-yl-propyl)-pyrido[2,3-d]pyrimidine-2,7-diamine (1.0 g) from Example 58 in DMF (15 mL) was added one equivalent of 60% sodium hydride suspension (0.92 g). After stirring for approximately 1 hour at room temperature, one equivalent of tert-butyl isocyanate (0.230 g) was added, and the reaction was monitored by thin layer chromatography. After approximately 4 hours, the solvent was removed in vacuo. The residue was partitioned between ethyl acetate and water. The aqueous layer was washed several times with ethyl acetate. The ethyl acetate layers were combined, dried with magnesium sulfate, and concentrated in vacuo. Chromatography of the residue on silica gel using ethyl acetate followed by ethyl acetate:ethanol:triethylamine (18:2:1) gave 0.98 g of the title compound 1-tert-butyl-3-[6-(2,6-dichlorophenyl)-2-(3-morpholin-4-yl-propylamino)-pyrido [2,3-d]pyrimidin-7-yl]-urea, CIMS (1% NH$_3$ in CH$_4$): 532=M$^+$+H, 531=M$^+$, 433, 84 (Base); mp 236–240° C.

Analysis calculated for C$_{25}$H$_{31}$N$_7$Cl$_2$O$_2$.0.25 EtOAc:

Theory: C, 56.32; H, 6.00; N, 17.68.

Found: C, 56.48; H, 6.06; N, 17.63.

EXAMPLE 60

6-(2,6-Dibromo-phenyl)-pyrido[2,3-d]pyrimidine-2,7-diamine

To a solution of 0.23 g 60% sodium hydride suspension in 11.0 mL of 2-ethoxyethanol was added 4.18 g of 2,6-dibromophenylacetonitrile and 2.00 g of 2,4-diaminopyrimidine-5-carboxaldehyde. The reaction was refluxed for 4 hours, cooled, and poured into ice water. The residue was washed well with acetonitrile then diethyl ether to give 3.62 g of 6-(2,6-dibromophenyl)-pyrido[2,3-d]pyrimidine-2,7-diamine, CIMS (1% NH$_3$ in CH$_4$): 422=M$^+$+C$_2$H$_5$, 396 (Base), 394=M$^+$+H, 393=M$^+$; mp 284–289° C.

Analysis calculated for C$_{13}$H$_9$N$_5$Br$_2$:

Theory: C, 39.52; H, 2.30; N, 17.73.

Found: C, 39.20; H, 2.27; N, 17.77.

EXAMPLE 61

6-(2,6-Dibromo-phenyl)-N$^2$-[3-diethylamino-propyl)-pyrido[2,3-d]pyrimidine-2,7-diamine A mixture of 6-(2,6-dibromo-phenyl)-pyrido[2,3-d]pyrimidine-2,7-diamine (1.0 g) from Example 60, sulfamic acid (0.49 g), and diethylaminopropylamine (8.0 mL) was reacted for 5 hours and worked up as in Example 53 to afford 0.79 g of the title compound 6-(2,6-dibromo-phenyl)-N$^2$-[3-diethylamino-propyl)-pyrido[2,3-d]pyrimidine-2,7-diamine, CIMS (1% NH$_3$ in CH$_4$): 507=M$^+$+H, 506=M$^+$, 112 (Base); mp 226–230° C.

Analysis calculated for C$_{20}$H$_{24}$N$_6$Br$_2$:

Theory: C, 47.26; H, 4.76; N, 16.53.

Found: C, 47.61; H, 4.69; N, 16.40.

EXAMPLE 62

1-tert-Butyl-3-[6-(2,6-dibromo-phenyl)-2-(3-diethylamino-propylamino)-pyrido[2,3-d]pyrimidin-7-yl]-urea 6-(2,6-Dibromo-phenyl)-N$^2$-[3-diethylamino-propyl)-pyrido[2,3-d]pyrimidine-2,7-diamine (0.34 g) from Example 61 was reacted with 0.066 g of tert-butyl isocyanate according to the general procedure of Example 54. The crude residue was purified by thin layer chromatography with ethyl acetate:ethanol:triethylamine (9:2:1) followed by preparative HPLC chromatography using a Vydac 218 TP 1022 reverse phase column with a gradient elution of 0.1% trifluoroacetic acid/water and 0.1% trifluoroacetic acid/acetonitrile to give 0.214 g of the title compound, ESMS (20/80 MEOH/CH$_3$CN+0.1% AcOH): 606=M$^+$+H; mp dec. >45° C.

Analysis calculated for C$_{25}$H$_{33}$N$_7$Br$_2$O.2.50 TFA.H$_2$O:

Theory: C, 39.58; H, 4.15; N, 10.77.

Found: C, 39.54; H, 3.82; N, 10.49.

EXAMPLE 63

6-(2,6-Difluoro-phenyl)-pyrido[2,3-d]pyrimidine-2,7-diamine 6-(2,6-Difluoro-phenyl)-pyrido[2,3-d]pyrimidine-2,7-diamine was prepared as described above in Example 60 using 4.65 g of 2,6-difluorophenylacetonitrile, CIMS (1% NH$_3$ in CH$_4$): 414=M$^+$+C$_3$H$_5$, 302=M$^+$+C$_2$H$_5$, 274=M$^+$+H (Base), 273=M$^+$, 254=M$^+$–F; mp >300° C.

Analysis calculated for C$_{13}$H$_9$N$_5$F$_2$:
Theory: C, 57.14; H, 3.32; N, 25.63.
Found: C, 57.30; H, 3.52; N, 25.62.

EXAMPLE 64

6-(2,6-Dimethoxy-phenyl)-pyrido[2, 3-d] pyrimidine-2,7-diamine 6-(2,6-Dimethoxy-phenyl)-pyrido[2,3-d]pyrimidine-2,7-diamine was prepared as described above in Example 60 substituting 2,6-dimethoxybenzylacetonitrile for 2,6-dibromophenylacetonitrile, reacting for 3 hours and crystallizing the product from ethyl alcohol, CIMS (1% NH$_3$ in CH$_4$): 326=M$^+$+C$_2$H$_5$, 298=M$^+$+H (Base), 297=M$^+$, 266= M$^+$–OMe; mp >300° C.

Analysis calculated for C$_{15}$H$_{15}$N$_5$O$_2$.0.50 H$_2$O:
Theory: C, 58.82; H, 5.26; N, 22.86.
Found: C, 58.81; H, 5.04; N, 22.54.

EXAMPLE 65

6-(2, 6-Dichlorophenyl)-N$^2$-(2-diethylamino-ethyl)-pyrido[2,3-d]pyrimidine-2,7-diamine A mixture of 2,7-diamino-6-(2,6-dichlorophenyl)-pyrido [2,3-d]pyrimidine (4.0 g) from Example 1, sulfamic acid (2.53 g), and diethylaminoethylamine (40 mL) was heated to approximately 150° C. for 20 hours. The excess diethylaminoethylamine was removed in vacuo. The resulting oil was dissolved in diethyl ether, diluted with hexane, and then filtered. The resulting solid was dissolved in dichloromethane which was washed several times with water, dried with magnesium sulfate, and concentrated in vacuo. The residue was crystallized from ethyl acetate to give the title compound 6-(2, 6-dichlorophenyl)-N$^2$-(2-diethylaminoethyl)-pyrido[2,3-d]pyrimidine-2,7-diamine, CIMS (1% NH$_3$ in CH$_4$): 433=M$^+$+C$_2$H$_5$, 405=M$^+$+H, 389= M$^+$–Et, 360; mp 216–219.5° C.

Analysis calculated for C$_{19}$H$_{22}$N$_6$Cl$_2$:
Theory: C, 56.30; H, 5.47; N, 20.73.
Found: C, 56.31; H, 5.39; N, 20.46.

EXAMPLE 66

1-tert-Butyl-3-[6-(2,6-dichlorophenyl)-2-(2-diethylamino-ethylamino)-pyrido[2,3-d]pyrimidin-7-yl]-urea 6-(2,6-Dichlorophenyl)-N$^2$-(2-diethylamino-ethyl)-pyrido[2,3-d]pyrimidine-2,7-diamine (1.0 g) from Example 65 in DMF (10 mL) was reacted with 60% sodium hydride suspension (0.099 g) and tert-butyl isocyanate (0.244 g) for 1 hour according to the general procedure of Example 54. Chromatography with ethyl acetate:ethanol:triethylamine (18:2:1) gave 0.76 g of the title compound 1-tert-butyl-3-[6-(2,6-dichlorophenyl)-2-(2-diethylamino-ethylamino)-pyrido[2,3-d]pyrimidin-7-yl]-urea, CIMS (1% NH$_3$ in CH$_4$): 504=M$^+$+H, 84 (Base); mp 94.5–96.5° C.

Analysis calculated for C$_{24}$H$_{31}$N$_7$Cl$_2$O:
Theory: C, 57.14; H, 6.19; N, 19.44.
Found: C, 56.94; H, 6.18; N, 19.22.

EXAMPLE 67

1-[6-(2,6-Dichlorophenyl)-2-(2-diethylamino-ethylamino)-pyrido[2,3-d]pyrimidin-7-yl]-3-ethyl-urea 6-(2,6-Dichlorophenyl)-N$^2$-(2-diethylamino-ethyl)-pyrido[2,3-d]pyrimidine-2,7-diamine (1.0 g) from Example 65 in DMF (10 mL) was reacted with 60% sodium hydride suspension (0.099 g) and ethyl isocyanate (0.175 g) according to the general procedure of Example 54 to give 0.86 g of the title compound 1-[6-(2,6-dichlorophenyl)-2-(2-diethylamino-ethylamino)-pyrido[2,3-d]pyrimidin-7-yl]-3-ethyl-urea, CIMS (1% NH$_3$ in CH$_4$): 476=M$^+$+H, 86 (Base); mp 86.5–89.5° C.

Analysis calculated for C$_{22}$H$_{23}$N$_7$Cl$_2$O:
Theory: C, 55.47; H, 5.71; N, 20.58.
Found: C, 55.18; H, 5.74; N, 20.20.

EXAMPLE 68

6-(2,6-Dichlorophenyl)-N2 -(3-dimethylamino-propyl)-N$^2$-methyl-pyrido[2,3-d]pyrimidine-2,7-diamine A mixture of 2,7-diamino-6-(2,6-dichlorophenyl)-pyrido [2,3-d]pyrimidine (4.0 g) from Example 1, sulfamic acid (2.53 g) and N,N,N'-trimethyl-1,3-propanediamine (20 mL) was heated in a bomb first at 165° C. for 16 hours then at 225° C. for 16 hours After cooling, the reaction mixture was concentrated in vacuo. The residue was partitioned between dilute sodium bicarbonate and dichloromethane. The aqueous solution was extracted with dichloromethane several times. The dichloromethane layers were combined, filtered, and concentrated in vacuo. The residue was chromatographed with ethyl acetate:ethanol:triethylamine (9:3:1) to give the title compound 6-(2, 6-dichlorophenyl)-N$^2$-(3-dimethylamino-propyl)-N$^2$-methyl-pyrido[2,3-d] pyrimidine-2,7-diamine.

EXAMPLE 69

1-tert-Butyl-3-{6-(2,6-dichlorophenyl)-2-[(3-dimethylamino-propyl)-methyl-amino]-pyrido[2,3-d] pyrimidin-7-yl}-urea 6-(2,6-Dichlorophenyl)-N$^2$-(3-dimethylamino-propyl)-N$^2$-methyl-pyrido[2,3-d]pyrimidine-2,7-diamine (0.38 g) from Example 68 in DMF (7.0 mL) was reacted with 60% sodium hydride suspension (0.022 g) and tert-butyl isocyanate (0.093 g) according to the general procedure of Example 54 to give 0.25 g of the title compound 1-tert-butyl-3-{6-(2,6-dichlorophenyl)-2-[(3-dimethylamino-propyl)-methyl-amino]-pyrido[2,3-d]-pyrimidin-7-yl}-urea, CIMS (1% NH$_3$ in CH$_4$) 504=M$^+$+H, 84 (Base); mp dec 76° C. then melts 87.5–91° C.

Analysis calculated for C$_{24}$H$_{31}$N$_7$Cl$_2$O.0.25 H$_2$O:
Theory: C, 56.64; H, 6.24; N, 19.26.
Found: C, 56.55; H, 6.07; N, 18.94.

EXAMPLE 70

2-({3-[7-Amino-6-(2,6-dichlorophenyl)-pyrido[2,3-d]-pyrimidin-2-ylamino]-propyl}-ethyl-amino)-ethanol A mixture of 2,7-diamino-6-(2,6-dichlorophenyl)-pyrido [2,3-d]pyrimidine (3.0 g) from Example 1, sulfamic acid (1.9 g) and N$^1$-ethyl-N$^1$-(2-hydroxyethyl)-propylenediamine (10.0 g) (J. Med. Chem., 11(3):583–591, (1968)) was reacted for 18 hours according to the general procedure of Example 36. In this instance, the residue was chromatographed using ethyl acetate:ethanol:triethylamine (9:3:1) to give 2.71 g of the title compound 2-({3-[7-amino-6-(2,6-dichlorophenyl)-pyrido[2,3-d]pyrimidin-2-ylamino]-propyl}-ethyl-amino)-ethanol, CIMS (1% NH$_3$ in CH$_4$): 463=M$^+$+C$_2$H$_5$, 435=M$^+$+H, 346 (Base); mp 201–204° C.

Analysis calculated for $C_{20}H_{24}N_6Cl_2O$:

Theory: C, 55.18; H, 5.56; N, 19.30.

Found: C, 55.11; H, 5.53; N, 19.09.

EXAMPLE 71

4-Amino-2-phenylamino-pyrimidine-5-carbonitrile

A solution of aniline (3.31 g) in tetrahydrofuran (40.0 mL) and diisopropylethylamine (4.60 g) was added to a solution of 4-amino-2-chloropyrimidine-5-carbontrile (5.00 g) in tetrahydrofuran (50.0 mL). The reaction mixture was heated to reflux. After 3 days, additional aniline (6.02 g) and diisopropylethylamine (8.36 g) was added to the reaction. After 24 hours, the reaction mixture was concentrated in vacuo, and the residue was partitioned between ethyl acetate and water. The ethyl acetate layer was washed twice with water then filtered through a fiberglass filter to disperse the emulsion that was present. The filtrate was washed with water then saturated sodium chloride, dried with magnesium sulfate, and concentrated in vacuo. The residue was washed with diethyl ether to give 6.00 g of the title compound, CIMS (1% $NH_3$ in $CH_4$): 252=$M^++C_3H_5$, 240=$M^++C_2H_5$, 212 $M^++H$ (Base), 211=$M^+$.

Analysis calculated for $C_{11}H_9N_5$:

Theory: C, 62.55; H, 4.29; N, 33.16.

Found: C, 62.85; H, 4.47; N, 33.18.

EXAMPLE 72

4-Amino-2-phenylamino-pyrimidine-5-carboxaldehyde

4-Amino-2-phenylamino-pyrimidine-5-carbonitrile (2.00 g) obtained from Example 71 was combined with wet Raney nickel (2.00 g), 98% formic acid (60 mL) and water (40 mL) in a Parr shaker The reaction was placed under hydrogen (42 psi) and shaken for 20 minutes. The reaction was filtered, and the filtrate was concentrated in vacuo. The residue was suspended in water, made basic with saturated sodium bicarbonate, and extracted with ethyl acetate three times. The aqueous layer was filtered through a fiberglass filter to disperse the emulsion that was present. The aqueous filtrate was washed with ethyl acetate. The ethyl acetate washes were combined, filtered, washed with saturated sodium chloride, dried with magnesium sulfate and concentrated in vacuo. Chromatography down silica gel, eluting with ethyl acetate:hexane (2:1) gave 0.73 g of the title compound, CIMS (1% $NH_3$ in $CH_4$): 243=$M^++C_2H_5$, 215=$M^++H$ (Base), 214=$M^+$.

Analysis calculated for $C_{11}H_{10}N_4O$:

Theory: C, 61.67; H, 4.71; N, 26.15.

Found: C, 61.79; H, 4.71; N, 26.11.

EXAMPLE 73

6-(2, 6-Dichlorophenyl)-$N^2$-phenyl-pyrido [2, 3-d]-pyrimidine-2,7-diamine

To a solution of 0.022 g 60% sodium hydride suspension in 2.00 mL of 2-ethoxyethanol was added 0.46 g of 2,6-dichlorophenylacetonitrile and 0.50 g of 4-amino-2-phenylamino-pyrimidine-5-carboxaldehyde from Example 72. The reaction was refluxed for 4 hours, cooled, poured into water, and extracted several times with dichloromethane. The dichloromethane washes were combined, washed with saturated sodium chloride, dried with magnesium sulfate, and concentrated in vacuo. The residue was washed with diethyl ether to give 0.61 g of the title compound, CIMS (1% $NH_3$ in $CH_4$): 410=$M^++C_2H_5$, 382=$M^++H$, 381=$M^+$.

The above compound can be reacted with tert.-butyl isocyanate according to the procedure of Example 52 to give 1-tert.-butyl-3-[[6-(2,6-dichlorophenyl)-2-phenylamino]-pyrido[2,3-d]pyrimidin-7-yl]-urea.

EXAMPLE 74

4-Amino-2-methylsulfanyl-pyrimidine-5-carboxylic acid ethyl ester

To a suspension of ethyl 4-chloro-2-methylthio-5-pyrimidinecarboxylate (25 g) in ethanol (200 mL) was added 30% ammonium hydroxide (38 mL). After stirring 5 hours at room temperature, the reaction was concentrated in vacuo. The residue was suspended in water and filtered. The filter pad, washed with water then diethyl ether, gave 17.68 g of the title compound, CIMS (1% $NH_3$ in $CH_4$): 242=$M^++C_2H_5$, 214=$M^++H$ (Base), 213=$M^+$, 168=$M^+$-OEt.

Analysis calculated for $C_8H_{11}N_3SO_2$:

Theory: C, 45.06; H, 5.20; N, 19.70.

Found: C, 44.84; H, 5.14; N, 19.64.

EXAMPLE 75

4-Amino-2-methylsulfanyl-pyrimidin-5-yl)-methanol

Into a suspension of lithium aluminum hydride (1.45 g) in tetrahydrofuran (50 mL) was added dropwise a solution of 4-amino-2-methylsulfanyl-pyrimidin-5-yl)-methanol (5.00 g) from Example 74 in tetrahydrofuran (120 mL). After stirring 1 hour at room temperature, the reaction was quenched with water (1.5 mL), 15% sodium hydroxide (1.5 mL), and finally water again (4.5 mL). The reaction was filtered, and the filter pad was washed with tetrahydrofuran. Concentration of the filtrate in vacuo gave 3.83 g of the title compound, CIMS (1% $NH_3$ in $CH_4$): 200=$M^++C_2H_5$, 172=$M^++H$ (Base), 171=$M^+$, 154=$M^+$-OH.

EXAMPLE 76

4-Amino-2-methylsulfanyl-pyrimidine-5-carboxaldehyde

Into a solution of crude 4-amino-2-methylsulfanyl-pyrimidin-5-yl)-methanol (1.5 g) from Example 76 in chloroform (150 mL) was added manganese dioxide (5.67 g) portionwise over 3 minutes. After 6 hours at room temperature, the reaction was filtered through Celite. The filter pad was washed with chloroform then ethyl acetate. The filtrates were combined and concentrated in vacuo to give 1.40 g of the title compound.

EXAMPLE 77

6-(2,6-Dichlorophenyl)-2-methylsulfanyl-pyrido-[2, 3-d]pyrimidin-7-ylamine

Into a solution of 2,6-dichlorophenylacetonitrile (0.55 g) in dimethylformamide (5 mL) was added one equivalent of 60% sodium hydride suspension (0.12 g). After 10 minutes, 4-amino-2-methylsulfanyl-pyrimidine-5-carbaldehyde (0.50 g) obtained from Example 76 was added. After stirring overnight at room temperature, the reaction was quenched with water. The aqueous solution was acidified with 1N hydrochloric acid to a pH of 7 and extracted several times with dichloromethane. The combined dichloromethane layers were washed with saturated sodium chloride, dried with magnesium sulfate, and concentrated in vacuo. Chromatography of this residue down silica gel with ethyl acetate:hexane (2:1) gave 0.32 g of the title compound, CIMS (1% NH$_3$ in CH$_4$): 365=M$^+$+C$_2$H$_5$, 337=M$^+$+H (Base), 336=M$^+$.

EXAMPLE 78

N'-[6-(2,6-Dichlorophenyl)-2-{3-(diethylamino) propylamino}pyrido[2,3-d]pyrimidin-7-yl]-N,N-dimethylformamidine To a suspension of 210 mg (1 mmol) of 7-amino-6-(2,6-dichlorophenyl)-2-[3-(diethylamino)propylamino]-pyrido[2,3-d]pyrimidine from Example 20 in 0.8 mL of DMF was added 0.8 mL of DMF dimethyl acetal. The mixture was stirred at room temperature for 5.5 hours, then concentrated in vacuo. The residual oil was distributed between dichloromethane and water. The organic phase was dried over magnesium sulfate, then concentrated to a glass that was crystallized from acetonitrile to give 160 mg (68%) of N'-[6-(2,6-dichlorophenyl)-2-{3-(diethylamino) propylamino}-pyrido[2,3-d]pyrimidin-7-yl]-N,N-dimethylformamidine, mp 100–104° C. CIMS (1% ammonia in methane): m/z (relative intensity) 476 (MH$^+$+2, 60), 474 (MH$^+$, 94), 361 (100).

Analysis calculated for C$_{23}$H$_{29}$Cl$_2$N$_7$.0.4 H$_2$O:
C, 57.36; H, 6.24; N, 20.36.
Found: C, 57.28; H, 6.05; N, 20.07.

EXAMPLE 79

N'-[7-(3-tert-Butylureido)-6-(2,6-dichlorophenyl)-pyrido[2,3-d]pyrimidin-2-yl]-N,N-dimethylformamidine 1-[2-Amino-6-(2,6-dichlorophenyl)-pyrido[2,3-d]-pyrimidin-7-yl]-3-tert-butylurea from Example 3 was reacted with DMF dimethyl acetal for 13.5 hours as described in Example 78. Workup as described above, followed by purification on flash silica gel chromatography eluting sequentially with 100:0, 3:1, 1:1, and 0:100 dichloromethane:ethyl acetate gave a solid that was triturated in 2-propanol to afford the title compound N'-[7-(3-tert-butylureido)-6-(2,6-dichlorophenyl)-pyrido[2,3-d] pyrimidin-2-yl]-N,N-dimethylformamidine, mp 190–193° C. CIMS (1% ammonia in methane): m/z (relative intensity) 462 (MH$^+$+2, 0.78), 460 (MH$^+$, 0.93).

Analysis calculated for C$_{21}$H$_{23}$Cl$_2$N$_7$O.0.2 C$_3$H$_8$O.0.2 C$_3$H$_7$NO:
C, 54.75; H, 5.38 N, 20.71.
Found: C, 54.73; H, 5.31; N, 20.65.

EXAMPLE 80

N'-[6-(2,6-Dichlorophenyl)-7-[(dimethylamino) methylene-amino]-pyrido[2,3-d]pyrimidin-2-yl]-N,N-dimethylformamidine 2,7-Diamino-6-(2,6-dichlorophenyl)-pyrido[2,3-d]-pyrimidine from Example 1 was reacted with DMF dimethyl acetal for 23 hours as described in Example 78. Workup as described above followed by purification on flash silica gel chromatography eluting sequentially with 100:0, 9:1, 4:1, and 7:3 ethyl acetate:methanol gave an oil that was crystallized from ethyl acetate to afford N'-[6-(2,6-dichlorophenyl)-7-[(dimethylamino)-methyleneamino]-pyrido[2,3-d]pyrimidin-2-yl]-N,N-dimethylformamidine, mp 269–272° C. CIMS (1% ammonia in methane): m/z (relative intensity) 418 (MH$^+$+2, 60), 416 (MH$^+$, 100).

Analysis calculated for C$_{19}$H$_{19}$Cl$_2$N$_7$.0.3 H$_2$O:
C, 54.11; H, 4.68; N, 23.25.
Found: C, 54.21; H, 4.58; N, 22.89.

EXAMPLE 81

6-Phenyl-pyrido[2,3-d]pyrimidine-2,7-diamine

Following the procedure of Example 1, phenylacetonitrile was reacted with 2,4-diamino-5-pyrimidine-carboxaldehyde to give the title compound; mp 317–318° C.

EXAMPLE 82

1-(2-Amino-6-phenyl-pyrido[2,3-d]pyrimidin-7-yl)-3-tert-butyl-urea

Following the procedure of Example 2, 0.246 g of 6-phenyl-pyrido[2,3-d]pyrimidine-2,7-diamine from Example 81 was reacted with 0.128 mL of tert-butyl isocyanate. The product is purified by medium pressure chromatography using silica gel and eluting with a gradient of 1:1 CHCl$_3$:EtOAc to EtOAc to afford the title compound; mp >250° C., CIMS (1% ammonia in methane): m/z (relative intensity) 337 (MH$^+$+1, 64), 338 (MH$^+$+2, 11), 236 (100).

EXAMPLE 83

6-(2,3-Dichlorophenyl)-pyrido[2,3-d]pyrimidine-2,7-diamine

Following the procedure of Example 1, 2,3-dichlorophenylacetonitrile was reacted with 2,4-diamino-5-pyrimidinecarboxaldehyde to give the title compound; mp 366–369° C. (dec).

EXAMPLE 84

1-[2-Amino-6-(2,3-dichlorophenyl)-pyrido[2,3-d]-pyrimidin-7-yl]-3-tert-butyl-urea Following the general procedure of Example 2, 0.502 g of 6-(2,3-dichlorophenyl)-pyrido[2,3-d]-pyrimidine-2,7-diamine from Example 83 was reacted with 0.206 mL of tert-butyl isocyanate. The product is purified by silica gel chromatography eluting with a gradient of CHCl$_3$:EtOAc (98:2) to CHCl$_3$:EtOAc (1:2) to afford the title compound; mp 356–358° C.

Analysis calculated for C$_{18}$H$_{18}$Cl$_2$N$_6$O.0.05 H$_2$O:
Theory: C, 53.34; H, 4.48; N, 20.74.
Found: C, 53.44; H, 4.47; N, 20.29.

EXAMPLE 85

6-(2,3,6-Trichloro-phenyl)-pyrido[2,3-d]pyrimidine-2,7-diamine

The title compound was prepared according to Example 1, starting from 1.0 g of (2,3,6-trichloro)-phenyl-acetonitrile and 0.6 g of 2,4-diamino-5-pyrimidine-carboxaldehyde; mp 320–322° C.

Analysis calculated for C$_{13}$H$_8$Cl$_3$N$_5$:
Theory: C, 45.84; H, 2.37; N, 20.56.
Found: C, 46.22; H, 2.57; N, 20.54.

EXAMPLE 86

1-[2-Amino-6-(2,3,6-trichloro-phenyl)-pyrido[2,3-d]-pyrimidin-7-yl]-3-tert-butyl-urea The procedure of Example 2 was followed to react 0.30 g of 6-(2,3,6-trichloro-phenyl)-pyrido[2,3-d]-pyrimidine-2, 7-diamine from Example 85 with tert-butyl isocyanate (0.108 mL). The product is purified by medium pressure chromatography (MPLC) using silica gel and eluting with 1:1 CHCl$_3$:EtOAc to afford the title compound; mp 329–330° C., CIMS (1% ammonia in methane): m/z (relative intensity) 439 (MH$^+$−1, 3), 441 (MH$^+$+1, 3), 84 (100).

EXAMPLE 87

1-[2-Amino-6-(2,6-difluoro-phenyl)-pyrido[2,3-d]-pyrimidin-7-yl]-3-tert-butyl-urea The title compound was prepared from 0.25 g of 6-(2,6-difluoro-phenyl)-pyrido[2,3-d]pyrimidine-2,7-diamine from Example 63 and 0.112 mL of tert-butyl isocyanate according to Example 2. The product was purified by MPLC eluting with a gradient of CHCl$_3$:EtOAc (1:1) to EtOAc to afford the pure product; mp >300° C., CIMS (1% ammonia in methane): m/z (relative intensity) 373 (MH$^+$+1, 60), 374 (MH$^+$+2, 10), 274 (100)

EXAMPLE 88

1-[2-Amino-6-(2,6-dibromo-phenyl)-pyrido[2,3-d]-pyrimidin-7-yl]-3-tert-butyl-urea The title compound was prepared from 0.25 g of 6-(2,6-dibromo-phenyl)-pyrido[2,3-d]pyrimidine-2,7-diamine from Example 60 and 0.077 mL of tert-butyl isocyanate according to Example 2. The product was purified by MPLC eluting with a gradient of CHCl$_3$:EtOAc (1:1) to EtOAc to afford the pure product; mp >300° C. (dec).

Analysis calculated for C$_{18}$H$_{18}$Br$_2$N$_6$O$_1$.0.35 H$_2$O:
C, 43.20; H, 3.77; N, 16.79; Br, 31.93.
Found: C, 43.53; H, 3.64; N, 16.41; Br, 31.79.

EXAMPLE 89

1-[2-Amino-6-(2,6-dichlorophenyl)-pyrido[2,3-d]-pyrimidin-7-yl]-3-isopropyl-urea The title compound was prepared from 0.5 g of 6-(2,6-dichlorophenyl)-pyrido[2,3-d]pyrimidine-2,7-diamine from Example 1 and 0.172 mL of isopropyl isocyanate according to Example 2. The product was purified by MPLC eluting with a gradient of CHCl$_3$:EtOAc (1:1) to afford the pure product; mp 184–188° C., CIMS (1% ammonia in methane) m/z (relative intensity) 391 (MH$^+$, 16), 393 (MH$^+$+2, 11), 306 (100).

EXAMPLE 90

6-o-Tolyl-pyrido[2,3-d]pyrimidine-2,7-diamine

The title compound was prepared according to Example 1, starting from 2-methylbenzyl cyanide and 2,4-diamino-5-pyrimidine-carboxaldehyde; mp 300–302° C.

Analysis calculated for C$_{14}$H$_{13}$N$_5$:
Theory: C, 66.92; H, 5.21; N, 27.87.
Found: C, 66.4; H, 5.2; N, 27.9.

EXAMPLE 91

1-(2-Amino-6-o-tolyl-pyrido[2,3-d]pyrimidin-7-yl)-3-tert-butyl-urea

The title compound was prepared from 6-o-tolyl-pyrido[2,3-d]pyrimidine-2,7-diamine from Example 90 and tert-butyl isocyanate according to Example 2. The product was purified by MPLC eluting with CHCl$_3$:EtOAc (1:1) to afford the pure product; mp 195–197° C., CIMS (1% ammonia in methane): m/z (relative intensity) 351 (MH$^+$+1, 55), 352 (MH$^+$+2, 12), 84 (100).

EXAMPLE 92

6-(2,3-Dimethyl-phenyl)-pyrido[2,3-d]pyrimidine-2,7-diamine

The title compound was prepared according to Example 1, starting from 2,3-dimethylphenylacetonitrile and 2,4-diamino-5-pyrimidine-carboxaldehyde; mp 330–333° C.

EXAMPLE 93

1-[2-Amino-6-(2,3-dimethyl-phenyl)-pyrido[2,3-d]-pyrimidin-7-yl]-3-tert-butyl-urea The title compound was prepared from 0.5007 g of 6-(2,3-dimethyl-phenyl)-pyrido[2,3-d]pyrimidine-2,7-diamine from Example 92 and 0.23 mL tert-butyl isocyanate according to Example 2. The product was purified by MPLC eluting with a gradient of CHCl$_3$:EtOAc (2:1) to CHCl$_3$:EtOAc (1:1); mp 326–330° C., MS(CI)

Analysis calculated for C$_{20}$H$_{24}$N$_6$O$_1$.0.81 H$_2$O:
C, 63.38; H, 6.81; N, 22.17.
Found: C, 63.54; H, 6.47; N, 21.77.

EXAMPLE 94

6-(3,5-Dimethyl-phenyl)-pyrido[2,3-d]pyrimidine-2,7-diamine

The title compound was prepared according to Example 1, starting from 2.0 g of 3,5-dimethylphenyl-acetonitrile and 1.81 g of 2,4-diamino-5-pyrimidine-carboxaldehyde; mp 298–302° C., MS(CI).

Analysis calculated for C$_{15}$H$_{15}$N$_5$:
Theory: C, 67.91; H, 5.70; N, 26.40.
Found: C, 67.87; H, 5.75; N, 26.38.

EXAMPLE 95

1-[2-Amino-6-(3,5-dimethyl-phenyl)-pyrido[2,3-d]-pyrimidin-7-yl]-3-tert-butyl-urea The title compound was prepared from 0.3 g of 6-(3,5-dimethyl-phenyl)-pyrido[2,3-d]pyrimidine-2,7-diamine from Example 94 and 0.14 mL of tert-butyl isocyanate according to Example 2. The product is purified by MPLC eluting with 1:1 CHCl$_3$:EtOAc; mp 180–182° C., CIMS (1% ammonia in methane): m/z (relative intensity) 365 (MH$^+$+1, 16), 366 (MH$^+$+2, 3), 84 (100).

EXAMPLE 96

6-(2,4,6-Trimethyl-phenyl)-pyrido[2,3-d]pyrimidine-2,7-diamine

The title compound was prepared according to Example 1, starting from 0.915 g of 2,4,6-trimethyl-benzyl cyanide and 0.76 g of 2,4-diamino-5-pyrimidine-carboxaldehyde; mp 276–282° C.; CIMS (1% ammonia in methane): m/z (relative intensity) 279 (MH$^+$, 54), 280 (MH$^+$+1, 100)

EXAMPLE 97

1-[2-Amino-6-(2,4,6-trimethyl-phenyl)-pyrido[2,3-d]-pyrimidin-7-yl]-3-tert-butyl-urea The title compound was prepared from 0.25 g of 6-(2,4,6-trimethyl-phenyl)-pyrido[2,3-d]pyrimidine-2,7-diamine from Example 96 and 0.109 mL of tert-butyl isocyanate according to Example 2. The product was purified by medium pressure liquid chromatography eluting with 1:1 CHCl$_3$:EtOAc; mp 281–297° C.; CIMS (1% ammonia in methane): m/z (relative intensity) 379 (MH$^+$+1, 100), 380 (MH$^+$+2, 23).

EXAMPLE 98

6-(2,3,5,6-Tetramethyl-phenyl)-pyrido[2,3-d]pyrimidine-2,7-diamine

The title compound was prepared according to Example 1, starting from 1.999 g of 2,3,5,6-trimethyl-benzyl cyanide and 1.52 g of 2,4-diamino-5-pyrimidine-carboxaldehyde; mp 327–331° C.; CIMS (1% ammonia in methane): m/z (relative intensity) 293 (MH$^+$, 65), 294 (MH$^+$+1, 100).

EXAMPLE 99

1-[2-Amino-6-(2,3,5,6-tetramethyl-phenyl)-pyrido-[2,3-d]pyrimidin-7-yl]-3-tert-butyl-urea The title compound was prepared from 0.3 g of 6-(2,3,5,6-tetramethyl-phenyl)-pyrido[2,3-d]pyrimidine-2,7-diamine from Example 98 and 0.125 mL of tert-butyl isocyanate according to Example 2. The product was purified by medium pressure liquid chromatography eluting with 1:1 CHCl$_3$:EtOAc; mp >300° C.; CIMS (1% ammonia in methane): m/z (relative intensity) 393 (MH$^+$, 55), 394 (MH$^+$+1, 13), 84 (100).

EXAMPLE 100

6-(2-Methoxy-phenyl)-pyrido[2,3-d]pyrimidine-2,7-diamine

The title compound was prepared according to Example 1, starting from 2-methoxybenzyl cyanide and 2,4-diamino-5-pyrimidine-carboxaldehyde; mp 304–306° C. (dec).

Analysis calculated for C$_{14}$H$_{13}$N$_5$O$_1$:
Theory: C, 62.91; H, 4.90; N, 26.20.
Found: C, 63.16; H, 5.13; N, 26.42.

EXAMPLE 101

1-[$^2$-Amino-6-(2-methoxy-phenyl)-pyrido[2,3-d]pyrimidin-7-yl]-3-tert-butyl-urea The title compound was prepared from 0.203 g of 6-(2-methoxy-phenyl)-pyrido[2,3-d]pyrimidine-2,7-diamine from Example 100 and 0.093 mL of tert-butyl isocyanate according to Example 2. The product was purified by medium pressure liquid chromatography eluting with 1:1 CHCl$_3$:EtOAc; mp 300–301° C.; CIMS (1% ammonia in methane): m/z (relative intensity) 367 (MH$^+$+1, 67), 368 (MH$^+$+2, 14), 236 (100).

EXAMPLE 102

6-(3-Methoxy-phenyl)-pyrido[2,3-d]pyrimidine-2,7-diamine

The title compound was prepared according to Example 1, starting from 3-methoxybenzyl cyanide and 2,4-diamino-5-pyrimidine-carboxaldehyde; mp 284–286° C.

Analysis calculated for C$_{14}$H$_{13}$N$_5$O$_1$:
Theory: C, 62.9; H, 4.9; N, 26.2.
Found: C, 62.8; H, 5.0; N, 26.3.

EXAMPLE 103

1-[2-Amino-6-(3-methoxy-phenyl)-pyrido[2,3-d]pyrimidin-7-yl]-3-tert-butyl-urea

The title compound was prepared from 0.50 g of 6-(3-methoxy-phenyl)-pyrido[2,3-d]pyrimidine-2,7-diamine from Example 102 and 0.23 mL tert-butyl isocyanate according to Example 2. The product was purified by medium pressure liquid chromatography eluting with a gradient of CHCl$_3$:EtOAc (2:1) to CHCl$_3$:EtOAc (1:1) to EtOAc; mp 275–280° C.; MS(CI).

Analysis calculated for C$_{19}$H$_{22}$N$_6$O$_2$.0.45 H$_2$O:
C, 60.93; H, 6.16; N, 22.44.
Found: C, 61.22; H, 5.89; N, 22.09.

EXAMPLE 104

6-(2-Bromo-6-chloro-phenyl)-pyrido[2,3-d]pyrimidine-2,7-diamine

Prepared as described in Example 1, starting from 1.0 g of 2-bromo-6-chlorophenylacetonitrile and 0.57 g of 2,4-diamino-5-pyrimidine-carboxaldehyde, mp 264–280° C.; MS(CI).

Analysis calculated for C$_{13}$H$_9$Cl$_1$Br$_1$N$_5$:
Theory: C, 44.53; H, 2.59; N, 19.97.
Found: C, 44.48; H, 2.87; N, 20.10.

EXAMPLE 105

1-[2-Amino-6-(2-bromo-6-chloro-phenyl)-pyrido[2,3-d]-pyrimidin-7-yl]-3-tert-butyl-urea The title compound was prepared using 0.30 g of 6-(2-bromo-6-chloro-phenyl)-pyrido[2,3-d]pyrimidine-2,7-diamine from Example 104 and 0.105 mL of tert-butyl isocyanate according to Example 2. The product was purified by MPLC eluting with 1:1 CHCl$_3$:EtOAc; mp 314° C. (dec); MS(CI).

Analysis calculated for C$_{18}$H$_{18}$Br$_1$Cl$_1$N$_6$O$_1$.0.43 CHCl$_3$.0.27 C$_4$H$_8$O$_2$:
C, 44.65; H, 3.95; N, 16.01; Br, 15.22; Cl, 15.47.
Found: C, 44.39; H, 3.96; N, 15.82; Br, 14.83; Cl, 15.39.

EXAMPLE 106

Propane-1-sulfonic acid [2-amino-6-(2,6-dichlorophenyl)-pyrido[2,3-d]pyrimidin-7-yl]-amide To a slurry of 1.00 g of 2,7-diamino-6-(2,6-dichlorophenyl)-pyrido[2,3-d]pyrimidine from Example 1 in 15 mL of DMF was added 0.15 g sodium hydride (60% in mineral oil) portionwise and the mixture stirred for 1 hour. Propanesulfonyl chloride (0.39 mL) is added dropwise, and the reaction mixture stirred at ambient temperature for 16 hours. The reaction mixture is filtered to remove a small amount of insoluble material and the filtrate evaporated in vacuo. The product is purified by medium pressure liquid chromatography (MPLC) using silica gel and eluting with a gradient of CHCl$_3$:EtOAc (2:1) to CHCl$_3$:EtOAc (1:1) to afford the title compound.

Analysis calculated for C$_{16}$H$_{15}$Cl$_2$N$_5$O$_2$S$_1$.0.25 CHCl$_3$:
C, 44.14; H. 3.48; N, 15.84; S, 7.25.
Found: C, 43.92; H, 3.38; N, 15.54; S, 7.04.

EXAMPLE 107

6-Pyridin-3-yl-pyrido[2,3-d]pyrimidine-2,7-diamine

The procedure of Example 1 was followed to react 3-pyridylacetonitrile and 2,4-diamino-5-pyrimidine-carboxaldehyde to afford the title compound; mp 317–319° C. (dec).

Analysis calculated for $C_{12}H_{10}N_6$:
Theory: C, 60.50; H, 4.23; N, 35.27.
Found: C, 60.5; H, 4.3; N, 35.6.

EXAMPLE 108

1-(2-Amino-6-pyridin-3-yl-pyrido[2,3-d]pyrimidin-7-yl)-3-tert-butyl-urea

By following the procedure of Example 2, 0.30 g of 2,7-diamino-6-(3-pyridyl)-pyrido[2,3-d]pyrido[2,3-d]-pyrimidine from Example 107 was reacted with 0.16 mL of tert-butyl isocyanate. The product was purified by medium pressure chromatography using silica gel and eluting with 90:10:1 EtOAc:MeOH:TEA to afford the title compound; mp >300° C.; CIMS (1% ammonia in methane): m/z (relative intensity) 338 (MH$^+$+1, 8), 339 (MH$^+$+2, 1), 84 (100).

EXAMPLE 109

6-Pyridin-4-yl-pyrido[2,3-d]pyrimidine-2,7-diamine

To cooled (0° C.) 2-ethoxyethanol (13 mL) was added portionwise 0.30 g of sodium hydride (60% in mineral oil), and the suspension was stirred for 10 minutes. To this suspension was added 1.06 g of 4-pyridylacetonitrile hydrochloride, and the mixture was stirred at room temperature for 30 minutes. The neutralized solution of 4-pyridylacetonitrile in 2-ethoxyethanol was added to a reaction mixture containing sodium 2-ethoxyethoxide (prepared from 0.11 g of sodium hydride and 4.76 mL of 2-ethoxyethanol) and 0.9 g of 2,4-diamino-5-pyrimidinecarboxaldehyde. The resulting mixture was heated at reflux for 2 hours, cooled, and the insoluble product washed with diethylether and ethyl acetate to afford the title compound; mp >340° C.; MS (CI).

Analysis calculated for $C_{12}H_{10}N_6 \cdot 0.05 H_2O$:
C, 60.27; H, 4.26; N, 35.14.
Found: C, 60.35; H, 4.31; N, 34.75.

EXAMPLE 110

1-(2-Amino-6-pyridin-4-yl-pyrido[2,3-d]pyrimidin-7-yl)-3-tert-butyl-urea

Following the procedure of Example 2, 0.30 g of 2,7-diamino-6-(4-pyridyl)-pyrido[2,3-d]pyrimidine from Example 109 was reacted with 0.154 mL of tert-butyl isocyanate. The product was purified by medium pressure chromatography using silica gel and eluting with 90:10:1 EtOAc:MeOH:TEA, to afford the title compound, mp >350° C.; CIMS (1% ammonia in methane): m/z (relative intensity) 338 (MH$^+$+1, 6), 339 (MH$^+$+2, 1), 84 (100).

EXAMPLE 111

6-Pyridin-2-yl-pyrido[2,3-d]pyrimidine-2,7-diamine

The procedure of Example 1 was followed to react 0.84 mL of 2-pyridylacetonitrile and 1.0 g of 2,4-diamino-5-pyrimidinecarboxaldehyde to afford the title compound, mp 312–321° C.

Analysis calculated for $C_{12}H_{10}N_6 \cdot 0.07 H_2O$:
C, 60.18; H, 4.27; N, 35.09.
Found: C, 60.46; H, 4.34; N, 34.70.

EXAMPLE 112

1-[6-(2,6-Dichlorophenyl)-2-(3-diethylamino-propylamino)-pyrido[2,3-d]pyrimidin-7-yl]-3-ethyl-urea By following the general procedure of Example 21, 0.85 g of 7-amino-6-(2,6-dichlorophenyl)-2-(3-diethylamino-propylamino)-pyrido[2,3-d]pyrimidine from Example 20 was reacted with 0.176 mL of ethyl isocyanate. The product was purified by reverse phase preparative HPLC on a C18 reverse phase column, eluting with a solvent gradient starting from 90% of 0.1% trifluoroacetic acid in water/10% of 0.1% trifluoroacetic acid in acetonitrile to 60% of 0.1% trifluoroacetic acid in water/40% of 0.1% trifluoroacetic acid in acetonitrile, mp 92–108° C.

Analysis calculated for $C_{23}H_{29}Cl_2N_7O_1 \cdot 0.25 H_2O$:
C, 55.82; H, 6.01; N, 19.81.
Found: C, 55.84; H, 6.02; N, 19.68.

EXAMPLE 113

1-[6-(2,6-Dichlorophenyl)-2-(3-diethylamino-propylamino)-pyrido[2,3-d]pyrimidin-7-yl]-3-isopropyl-urea The procedure of Example 21 was followed to react 0.30 g of 7-amino-6-(2,6-dichlorophenyl)-2-(3-diethylamino-propylamino)-pyrido[2,3-d]pyrimidine from Example 20 and 0.077 mL of isopropyl isocyanate. The product was purified by medium pressure chromatography on silica gel eluting with 90:10:1 EtOAc:MeOH:TEA to afford the title compound, mp 88–100° C.; CIMS (1% ammonia in methane): m/z (relative intensity) 504 (MH$^+$, 3), 506 (MH$^+$+2, 2), 86 (100)

EXAMPLE 114

$N^2$-(3-Diethylamino-propyl)-6-(2,6-dimethyl-phenyl)-pyrido[2,3-d]pyrimidine-2,7-diamine The procedure of Example 20 was followed to react 3.0 g of 2,7-Diamino-6-(2,6-dimethylphenyl)pyrido-[2,3-d] pyrimidine from Example 6 and 30 mL of 1-amino-3-(N, N-diethylamino)propane to give the title compound, mp 216–219° C.

Analysis calculated for $C_{22}H_{30}N_6 \cdot 0.15 H_2O$:
C, 69.31; H, 8.01; N, 22.04.
Found: C, 69.29; H, 7.89; N, 22.04.

EXAMPLE 115

1-[2-(3-Dimethylamino-propylamino)-6-(2,6-dimethyl-phenyl)-pyrido[2,3-d]pyrimidin-7-yl]-3-ethyl-urea Prepared as described in Example 21, starting from 7-amino-6-(2,6-dimethylphenyl)-2-(3-diethylamino-propylamino)-pyrido[2,3-d]pyrimidine from Example 114 and ethyl isocyanate. The product was purified by reverse phase preparative HPLC on a C18 reverse phase column, eluting with a solvent gradient starting from 100% of 0.1% trifluoroacetic acid in water/0% of 0.1% trifluoroacetic acid in acetonitrile to 70% of 0.1% trifluoroacetic acid in water/ 30% of 0.1% trifluoroacetic acid in acetonitrile, mp 64–70° C.

Analysis calculated for $C_{25}H_{35}N_7O_1 \cdot 0.35 H_2O$:
C, 65.86; H, 7.89; N, 21.51.
Found: C, 65.78; H, 7.63; N. 21.39.

EXAMPLE 116

1-tert-Butyl-3-[2-(3-diethylamino-propylamino)-6-(2,6-dimethyl-phenyl)-pyrido[2,3-d]pyrimidin-7-yl]-urea Prepared as described in Example 21, starting from 0.50 g of 7-amino-6-(2,6-dimethylphenyl)-2-(3-diethylaminopropylamino)-pyrido[2,3-d]pyrimidine from Example 114 and 0.17 mL of tert-butyl isocyanate. The product was purified by reverse phase preparative HPLC on a C18 reverse phase column, eluting with a solvent gradient starting from 95% of 0.1% trifluoroacetic acid in water/5% of 0.1% trifluoroacetic acid in acetonitrile to 65% of 0.1% trifluoroacetic acid in water/35% of 0.1% trifluoroacetic acid in acetonitrile, mp 86–91° C.

Analysis calculated for $C_{27}H_{39}N_7O_1$:

Theory: C, 67.89; H, 8.23; N, 20.53.

Found: C, 67.70; H, 8.24; N, 20.43.

EXAMPLE 117

1-Adamantan-1-yl-3-{6-(2,6-dichlorophenyl)-2-[3-(4-methyl-piperazin-1-yl)-propylamino]-pyrido[2,3-d]-pyrimidin-7-yl}-urea Prepared as described above in Example 37 starting from 0.5 g of $N^2$-[3-(4-methyl-piperazin-1-yl)-propyl]-6-(2,6-dichlorophenyl)-pyrido[2,3-d]pyrimidine-2,7-diamine from Example 36 and 0.218 g of 1-adamantyl isocyanate. The product was purified by medium pressure chromatography using silica gel and eluting with 90:10:1 EtOAc:MeOH:TEA, to afford the title compound, mp >200° C. (dec); ESMS (20/80 MeOH/$CH_3CN$+0.1% AcOH): m/z (relative intensity) 623.4 ($MH^+$, 100), 625.5 ($MH^+$+2, 48).

Analysis calculated for $C_{32}H_{40}Cl_2N_8O_1 \cdot 0.52\ H_2O$:

C, 60.72; H, 6.54; N, 17.70.

Found: C, 61.06; H, 6.58; N, 17.30.

EXAMPLE 118

1-tert-Butyl-3-{6-(2,6-dichlorophenyl)-2-[3-(4-methyl-piperazin-1-yl)-propylamino]-pyrido[2,3-d]pyrimidin-7-yl}-thiourea Prepared as described above in Example 37 starting from 0.5 g of $N^2$-[3-(4-methyl-piperazin-1-yl)-propyl]-6-(2,6-dichlorophenyl)-pyrido[2,3-d]pyrimidine-2,7-diamine from Example 36 and 0.142 g of tert-butyl isothiocyanate. The product was purified by medium pressure chromatography using silica gel and eluting with 90:10:1 EtOAc:MeOH:TEA which gave a mixture of two products. The mixture was further purified by reverse phase preparative HPLC on a C18 reverse phase column, eluting with a solvent gradient starting from 95% of 0.1% trifluoroacetic acid in water/5% of 0.1% trifluoroacetic acid in acetonitrile to 65% of 0.1% trifluoroacetic acid in water/35% of 0.1% trifluoroacetic acid in acetonitrile, mp >200° C. (dec); MS(ES).

EXAMPLE 119

3-{6-(2,6-Dichlorophenyl)-2-[3-(4-methyl-piperazin-1-yl)-propylamino]-pyrido(2,3-d]pyrimidin-7-yl}-1,1-diethyl-urea To a solution of 0.50 g of $N^2$-[3-(4-methyl-piperazin-1-yl)-propyl]-6-(2,6-dichlorophenyl)-pyrido[2,3-d]pyrimidine-2,7-diamine from Example 36 in 5 mL DMF was added 0.10 g of 60% sodium hydride, and the mixture stirred for 1 hour at room temperature. The suspension was cooled to 0° C. and 0.15 mL of diethylcarbamyl chloride was added dropwise. After the addition was completed, the reaction mixture was allowed to warm to room temperature and stirred for 18 hours at ambient temperature. The mixture was concentrated in vacuo and the product purified by medium pressure chromatography on silica gel eluting with 90:10:1 EtOAc:MeOH:TEA to afford the title compound, mp >200° C. (dec); MS(ES).

EXAMPLE 120

$N^2$-[3-(4-Methyl-piperazin-1-yl)-propyl]-6-(2,3,5,6-tetramethyl-phenyl)-pyrido[2,3-d]pyrimidine-2,7-diamine A mixture of 1.00 g of 6-(2,3,5,6-tetramethyl-phenyl)-pyrido[2,3-d]pyrimidine-2,7-diamine from Example 98, 0.66 g of sulfamic acid, and 10 mL of 1-(3-aminopropyl)-4-methyl piperazine was heated to reflux with stirring for 34 hours. The reaction flask was fitted with a short path distillation column and the excess amine removed by distillation under high vacuum. The residue was diluted with 40 mL of dichloromethane, washed with 10 mL of water followed by a 15 mL wash with saturated sodium bicarbonate. The basic aqueous layer was extracted with dichloromethane (3×25 mL), and the combined organic layers back washed with brine (3×25 mL). The organic layer was dried over magnesium sulfate, filtered, and evaporated in vacuo. The product was purified by medium pressure chromatography using silica gel and eluting with 90:10:1 EtOAc:MeOH:TEA, to afford the titled compound, mp 218–223° C.; MS(APCI).

Analysis calculated for $C_{25}H_{35}N_7 \cdot 0.30\ C_4H_8O_2$:

C, 68.41; H, 8.19; N, 21.31.

Found: C, 68.05; H, 7.95; N, 21.70.

EXAMPLE 121

1-tert-Butyl-3-{2-[3-(4-methyl-piperazin-1-yl)-propylamino]-6-(2,3,5,6-tetramethyl-phenyl)-pyrido-[2,3-d]pyrimidin-7-yl}-urea Prepared as described in Example 37 starting from 0.41 g of $N^2$-[3-(4-methyl-piperazin-1-yl)-propyl]-6-(2,3,5,6-tetramethyl-phenyl)-pyrido[2,3-d]pyrimidine-2,7-diamine from Example 120 and 0.12 mL of tert-butyl isocyanate. The product was purified by medium pressure chromatography using silica gel and eluting with 90:10:1 EtOAc:MeOH:TEA to afford the title compound, mp 185–198° C.

Analysis calculated for $C_{30}H_{44}N_8O_1$:

Theory: C, 67.64; H, 8.33; N, 21.03.

Found: C, 67.31; H, 8.23; N, 20.87.

EXAMPLE 122

1-[6-(2,6-Dichlorophenyl)-2-(4-diethylamino-butylamino)-pyrido[2,3-d]pyrimidin-7-yl]-3-(3-morpholin-4-yl-propyl)-thiourea Prepared as described in Example 37 starting from 0.3926 g of $N^2$-[3-(4-methyl-piperazin-1-yl)-propyl]-6-(2,6-dichlorophenyl)-pyrido[2,3-d]pyrimidine-2,7-diamine from Example 53 and 0.18 g of 3-morpholinopropyl isothiocyanate. The product was purified by medium pressure chromatography on silica gel and eluting with a solvent mixture of 90:10:1 EtOAc:MeOH:TEA to afford the title compound; mp >200° C. (dec); ESMS (20/80 MeOH/$CH_3CN$+0.1% AcOH): m/z (relative intensity) 619.4 ($MH^+$, 100), 621.5 ($MH^+$2, 77).

EXAMPLE 123

1-tert-Butyl-3-[6-(2,6-dichlorophenyl)-2-(4-diethylamino-butylamino)-pyrido[2,3-d]pyrimidin-7-yl]-urea To a solution of 6-(2,6-dichlorophenyl)-$N^2$-(4-diethylamino-butyl)-pyrido[2,3-d]pyrimidine-2,7-diamine (25.0 g) from Example 53 in DMF (300 mL) was added 1 equivalent of 60% sodium hydride suspension (2.31 g). After stirring for approximately 2 hours at room temperature, one equivalent of phenyl isocyanate (5.72 g) was added and the reaction monitored by thin layer chromatography After approximately 24 hours, the solvent was removed in vacuo. The residue was dissolved in dichloromethane and this solution was washed several times, first with water and then a saturated solution of sodium chloride. The dichloromethane layer was dried with magnesium sulfate and concentrated in vacuo. Chromatography of the residue on silica gel eluting with ethyl acetate:ethanol:triethylamine (9:2:1), followed by crystallization from tert-butyl methyl ester gave 21.58 g of the title compound 1-tert-butyl-3-[6-(2,6-dichlorophenyl)-2-(4-diethylamino-butylamino)-pyrido[2,3-d]pyrimidin-7-yl]-urea, ESMS (20/80 MeOH/CH$_3$CN+0.1% AcOH): M$^+$+H=532; mp dec 157° C.

Analysis calculated for C$_{26}$H$_{35}$N$_7$Cl$_2$O.0.10 H$_2$O:
Theory: C, 58.45; H, 6.64; N, 18.35; Cl, 13.27; H$_2$O, 0.34.
Found: C, 58.51; H, 6.75; N, 18.37; Cl, 13.17; H$_2$O, 0.57.

EXAMPLE 124

1-[6-(2,6-Dichlorophenyl)-2-(4-diethylamino-butyl-amino)-pyrido[2,3-d]pyrimidin-7-yl]-3-ethyl-urea To a cooled (5° C.) solution of 6-(2,6-dichlorophenyl)-N$^2$-(4-diethylamino-butyl)-pyrido[2,3-d]pyrimidine-2,7-diamine (0.61 g) from Example 53 in THF (6 mL) was added potassium hexamethyldisilazane (0.308 g) in portions. The reaction mixture was allowed to warm to ambient temperature and stirred for 30 minutes. Then ethyl isocyanate was added, and the reaction mixture was stirred for an additional 18 hours at ambient temperature. The product was isolated by pouring the reaction mixture into approximately 200 mL of 0.25N aqueous HCl and filtering the resulting solution. The filtrate was made basic with 50% aqueous sodium hydroxide, and the aqueous layer was extracted twice with ethyl acetate. The combined organic extracts were dried (MgSO$_4$), filtered, and the filtrate concentrated under vacuum. The product was purified by radial chromatography eluting with a solvent mixture of 90:10:1 EtOAC-:MeOH:TEA to afford the title compound.

Analysis calculated for C$_{24}$H$_{31}$Cl$_2$N$_7$O$_1$.0.78 H$_2$O.
C, 55.59; H, 6.33; N, 18.91.
Found: C, 55.59; H, 5.93; N, 18.62.

EXAMPLE 125

N-[6-(2,6-Dichlorophenyl)-2-(3-diethylamino-propylamino)-pyrido[2,3-d]pyrimidin-7-yl-N"-ethyl-guanidine To a solution of 7-amino-6-(2,6-dichlorophenyl)-2-(3-diethylamino-propylamino)-pyrido[2,3-d]pyrimidine (42 mg) from Example 20 in DMF (1 mL) was added 60% sodium hydride suspension (5 mg), and the mixture was stirred at room temperature for 0.5 hour. To the reaction mixture was added N,N'-Bis(tert-butoxy-carbonyl)-N-(ethyl)-S-(ethyl)isothiourea (37 mg), and the mixture was stirred for 18 hours. The reaction mixture was diluted with dichloromethane (50 mL) and washed with water (2×15 mL). The organic layer was dried with sodium sulfate and concentrated. The resulting oil was purified on silica gel, eluting with methanol:ethyl acetate:triethylamine (8.5:1.5:0.3) to afford a mixture of 7-amino-6-(2,6-dichlorophenyl)-2-(3-diethylamino-propylamino)-pyrido[2, 3-d]pyrimidine (40 mg) and [[[6-(2,6-dichlorophenyl)-2-(3-diethylamino-propylamino)-pyrido[2,3-d]pyrimidin-7-yl]imino[[1,1-dimethylethoxy)carbonyl]amino]methyl]-ethylamino]carbamic acid-1,1-dimethylethyl ester. This mixture was dissolved in anhydrous dichloromethane (0.5 mL) containing 2.6-lutidine (8 mg). Trimethyl-silyl trifluoromethanesulfonate (6 mg) was added, and the mixture was stirred at room temperature for 30 hours. The mixture was poured into saturated aqueous sodium bicarbonate, extracted with dichloromethane, dried over sodium sulfate, and concentrated. The resulting oil was chromatographed on silica gel, eluting with methanol:ethyl acetate: triethylamine (8.5:1.5:0.3) to afford the title compound (7 mg), ESMS (1/4 MeOH/CH$_3$CN+0.1% AcOH): m/z (relative intensity) 490.5 (MH$^+$, 100), 491.5 (MH$^+$+1, 27), 492.5 (MH$^+$+2, 64).

The following examples further illustrate typical pharmaceutical formulations provided by this invention.

EXAMPLE 126

A pharmaceutical formulation in the form of hard gelatin capsules for oral administration are prepared using the following ingredients:

|  | Quantity (mg/capsule) |
| --- | --- |
| Active compound | 250 |
| Starch powder | 200 |
| Magnesium stearate | 10 |
| Total | 460 mg |

The above ingredients are mixed and filled into hard gelatin capsules in 460 mg quantities. A typical active ingredient is N-[2-formylamino-6-(3,5-dimethyl-phenyl)-pyrido[2,3-d]pyrimidin-7-yl]-n-butyamide. The composition is administered from 2 to 4 times a day for treatment of postsurgical restenosis.

EXAMPLE 127

| Formulation for Oral Suspension | |
| --- | --- |
| Ingredient | Amount |
| 3-(4,5-dibromophenyl)-[1,6]-naphthyridine-2,7-diamine | 500 mg |
| Sorbitol solution (70% N.F.) | 40 mL |
| Sodium benzoate | 150 mg |
| Saccharin | 10 mg |
| Cherry Flavor | 50 mg |
| Distilled water q.s. ad | 100 mL |

The sorbitol solution is added to 40 mL of distilled water and the naphthyridine is suspended therein. The saccharin, sodium benzoate, and flavoring are added and dissolved. The volume is adjusted to 100 mL with distilled water. Each milliliter of syrup contains 5 mg of active ingredient.

EXAMPLE 128

| Tablets each containing 60 mg of active ingredient | |
| --- | --- |
| Active ingredient | 60 mg |
| Starch | 45 mg |
| Microcrystalline cellulose | 35 mg |
| Polyvinylpyrrolidone (as 10% solution in water) | 4 mg |

61

-continued

| Tablets each containing 60 mg of active ingredient | |
|---|---|
| Sodium carboxymethyl starch | 4.5 mg |
| Magnesium stearate | 0.5 mg |
| Talc | 1.0 mg |
| Total | 150 mg |

The active ingredients, starch, and cellulose, are passed through a No. 45 mesh U.S. sieve and mixed thoroughly. The solution of polyvinylpyrrolidone is mixed with the resultant powders and then passed through a No. 14 mesh U.S. sieve. The granules are dried at 50–60° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

A typical active ingredient utilized in the above preparation is the compound of Example 21.

EXAMPLE 129

A parenteral composition suitable for administration by injection is prepared by dissolving 100 mg of 1-[2-amino-6-(2,6-dichlorophenyl)-pyrido-[2,3-d]pyrimidin-7-yl]-3-(3-morpholin-4-yl-propyl)-thiourea in 250 mL of 0.9% aqueous sodium chloride solution and adjusting the pH of the solution to about 7.0. This formulation is well suited for the treatment of breast cancer.

EXAMPLE 130

Preparation for Suppositories

A mixture of 500 mg of 1-[2-amino-6-(2,6-dichlorophenyl)-pyrido[2,3-d]pyrimidin-7-yl]-imidazolidin-2-one and 1500 mg of theobroma oil are blended to uniformity at 60° C. The mixture is cooled to 24° C. in tapered molds. Each suppository will weigh about 2 g and can be administered from 1 to 2 times each day for treatment of bacterial infections.

EXAMPLE 131

| Topical Preparation | |
|---|---|
| Ingredient | Amount (mg) |
| N$^7$-(3-methylaminopropyl)-6-(3,5-dimethoxyphenyl)-pyrido[2,3-d]pyrimidine-2,7-diamine | 20 |
| Propylene Glycol | 100 |
| White Petrolatum | 500 |
| Cetearyl Alcohol | 50 |
| Glyceryl Stearate | 100 |
| PEG 100 Stearate | 100 |
| Ceteth-20 | 50 |
| Monobasic Sodium Phosphate | 80 |
| TOTAL | 1000 |

62

What is claimed is:

1. A compound of Formula I

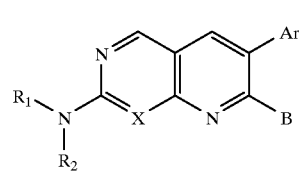

wherein

X is CH;

B is halo, hydroxy, or $NR_3R_4$;

$R_1$, $R_2$, $R_3$, and $R_4$ independently are hydrogen, $C_1$–$C_8$ alkyl, $C_2$–$C_8$ alkenyl, $C_2$–$C_8$ alkynyl, Ar', amino, $C_1$–$C_8$ alkylamino or di-$C_1$–$C_8$ alkylamino; and wherein the alkyl, alkenyl, and alkynyl groups may be substituted by $NR_5R_6$, where $R_5$ and $R_6$ are independently hydrogen, $C_1$–$C_8$ alkyl, $C_2$–$C_8$ alkenyl, $C_2$–$C_8$ alkynyl, $C_3$–$C_{10}$ cycloalkyl or

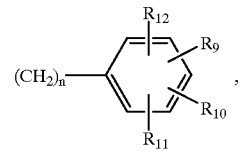

and wherein $R_9$, $R_{10}$, $R_{11}$, and $R_{12}$ independently are hydrogen, nitro, trifluoromethyl, phenyl, —C≡N, —COOR$_8$, —COR$_8$,

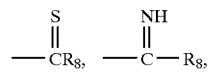

$SO_2R_8$, halo, $C_1$–$C_8$ alkyl, $C_1$–$C_8$ alkoxy, thio, —S—$C_1$–$C_8$ alkyl, hydroxy, $C_1$–$C_8$ alkanoyl, $C_1$–$C_8$ alkanoyloxy, or —NR$_5$R$_6$, or $R_9$ and $R_{10}$ taken together when adjacent can be methylenedioxy; n is 0, 1, 2, or 3; and wherein $R_5$ and $R_6$ together with the nitrogen to which they are attached can complete a ring having 3 to 6 carbon atoms and optionally containing a heteroatom selected from nitrogen, oxygen, and sulfur;

$R_1$ and $R_2$ together with the nitrogen to which they are attached, and $R_3$ and $R_4$ together with the nitrogen to which they are attached, can also be

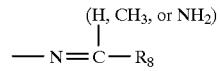

or can complete a ring having 3 to 6 carbon atoms and optionally containing 1 or 2 heteroatoms selected from nitrogen, oxygen, and sulfur, and $R_1$ and $R_3$ additionally can be an acyl analog selected from

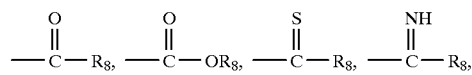

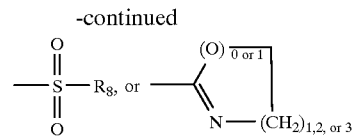

in which $R_8$ is hydrogen, $C_1$–$C_8$ alkyl, $C_2$–$C_8$ alkenyl, $C_2$–$C_8$ alkynyl, $C_3$–$C_{10}$ cycloalkyl optionally containing an oxygen, nitrogen, or sulfur atom,

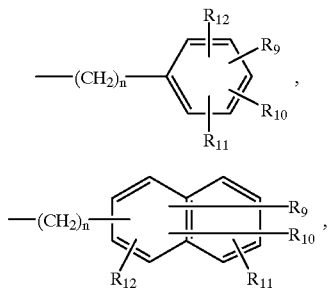

and —$NR_5R_6$, and wherein the $R^8$ alkyl, alkenyl, and alkynyl groups can be substituted by $NR_5R_6$;

Ar and Ar' are unsubstituted or substituted aromatic or heteroaromatic groups selected from phenyl, imidazolyl, pyrrolyl, pyridyl, pyrimidyl, benzimidazolyl, benzothienyl, benzofuranyl, indolyl, pyrazinyl, thiazolyl, oxazolyl, isoxazolyl, furanyl, thienyl, naphthyl, wherein the substituents are $R_9$, $R_{10}$, $R_{11}$, and $R_{12}$ as defined above;

or the pharmaceutically acceptable acid and base addition salts thereof.

2. A compound of claim 1 having the formula

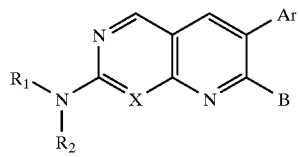

wherein

X is CH;

B is halo, hydroxy, or $NR_3R_4$;

$R_1$, $R_2$, $R_3$, and $R_4$ independently are hydrogen, $C_1$–$C_6$ alkyl, $C_2$–$C_6$ alkenyl, $C_2$–$C_6$ alkynyl, amino, $C_1$–$C_6$ alkylamino or di-$C_1$–$C_6$ alkylamino; and wherein the alkyl, alkenyl, and alkynyl groups may be substituted by $NR_5R_6$, where $R_5$ and $R_6$ are independently hydrogen, $C_1$–$C_6$ alkyl, $C_2$–$C_6$ alkenyl, $C_2$–$C_6$ alkynyl, $C_3$–$C_6$ cycloalkyl or

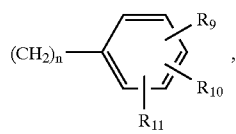

and wherein $R_9$, $R_{10}$, and $R_{11}$ independently are hydrogen, nitro, trifluoromethyl, phenyl, substituted phenyl, —C≡N, —$COOR_8$, —$COR_8$,

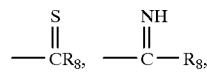

$SO_2R_8$, halo, $C_1$–$C_6$ alkyl, $C_1$–$C_6$ alkoxy, thio, —S—$C_1$–$C_6$ alkyl, hydroxy, $C_1$–$C_6$ alkanoyl, $C_1$–$C_6$ alkanoyloxy, or —$NR_5R_6$, or $R_9$ and $R_{10}$ taken together when adjacent can be methylenedioxy; n is 0, 1, 2, or 3; and wherein $R_5$ and $R_6$ together with the nitrogen to which they are attached can complete a ring having 3 to 6 carbon atoms and optionally containing a heteroatom selected from nitrogen, oxygen, and sulfur;

$R_1$ and $R_2$ together with the nitrogen to which they are attached, and $R_3$ and $R_4$ together with the nitrogen to which they are attached, can complete a ring having 3 to 6 carbon atoms and optionally containing a heteroatom selected from nitrogen, oxygen, and sulfur, and $R_1$ and $R_3$ additionally can be an acyl selected from

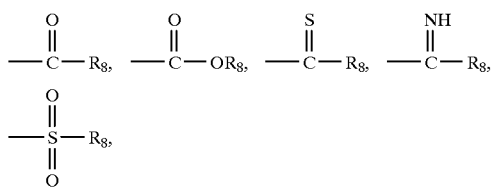

in which $R_8$ is hydrogen, $C_1$–$C_6$ alkyl, $C_2$–$C_6$ alkenyl, $C_2$–$C_6$ alkynyl, $C_3$–$C_6$ cycloalkyl,

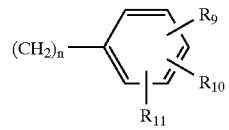

and —$NR_5R_6$, and wherein the alkyl, akenyl, and alkynyl groups can be substituted by $NR_5R_6$;

Ar is an unsubstituted or substituted aromatic or heteroaromatic group selected from phenyl, imidazolyl, pyrrolyl, pyridyl, pyrimidyl, benzimidazolyl, benzothienyl, benzofuranyl, indolyl, pyrazinyl, thiazolyl, oxazolyl, isoxazolyl, furanyl, thienyl, naphthyl, wherein the substituents are $R_9$, $R_{10}$, and $R_{11}$ as defined above;

or the pharmaceutically acceptable acid and base addition salts thereof.

3. A compound of claim 1 wherein B is halo or hydroxy.

4. A compound of claim 1 wherein B is $NR_3R_4$.

5. A compound of claim 4 wherein Ar is an optionally substituted phenyl ring of the formula

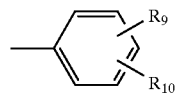

6. A compound of claim 5 wherein $R_2$ and $R_4$ are hydrogen.

7. A compound of claim 6 wherein $R_1$ and $R_3$ independently are hydrogen, $C_1$–$C_6$ alkyl,

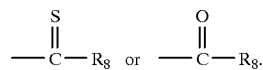

8. A compound of claim 7 wherein $R_8$ is $C_1$–$C_6$ alkyl, —$NR_5R_6$, or $C_1$–$C_6$ alkyl-$NR_5R_6$.

9. A compound of claim 8 wherein $R_5$ and $R_6$ independently are hydrogen, $C_1$–$C_6$ alkyl, or $C_1$–$C_6$ alkyl $NR_5R_6$.

10. The compound of claim 7 which is 3-o-tolyl-[1,6]naphthyridine-2,7-diamine.

11. The compound of claim 7 which is 3-(2-chlorophenyl)-[1,6]naphthyridine-2,7-diamine.

12. A pharmaceutical formulation comprising a compound of claim 1 together with a pharmaceutically acceptable carrier, diluent, or excipient therefor.

13. A formulation of claim 12 employing a compound wherein B is $NR_3R_4$.

14. A formulation of claim 12 employing a compound wherein Ar is an optionally substituted phenyl ring of the formula

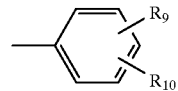

15. A formulation of claim 14 employing a compound wherein $R_2$ and $R_4$ are hydrogen, and $R_1$ and $R_3$ independently are hydrogen, $C_1$–$C_6$ alkyl,

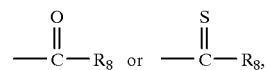

where $R_8$ is $C_1$–$C_6$ alkyl or —$NR_5R_6$.

16. A method of inhibiting cell proliferation and migration comprising administering to a host suffering therefrom a therapeutically effective amount of a compound according to claim 1 in unit dosage form.

\* \* \* \* \*